(12) United States Patent
Klee

(10) Patent No.: US 10,679,735 B2
(45) Date of Patent: *Jun. 9, 2020

(54) COMPUTER-IMPLEMENTED TOOLS FOR USE IN ELECTROPHYSIOLOGY

(71) Applicant: Maurice M. Klee, Fairfield, CT (US)

(72) Inventor: Maurice M. Klee, Fairfield, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 16/200,770

(22) Filed: Nov. 27, 2018

(65) Prior Publication Data

US 2019/0108321 A1  Apr. 11, 2019
US 2020/0097636 A9  Mar. 26, 2020

Related U.S. Application Data

(63) Continuation of application No. 15/097,379, filed on Apr. 13, 2016, now Pat. No. 10,169,545.

(60) Provisional application No. 62/150,453, filed on Apr. 21, 2015.

(51) Int. Cl.

| G06F 17/50 | (2006.01) |
|---|---|
| G06F 7/62 | (2006.01) |
| G16C 20/30 | (2019.01) |
| G16H 50/50 | (2018.01) |
| G06F 30/20 | (2020.01) |
| G06F 19/00 | (2018.01) |

(52) U.S. Cl.
CPC ............ G16C 20/30 (2019.02); G06F 19/00 (2013.01); G06F 30/20 (2020.01); G16H 50/50 (2018.01)

(58) Field of Classification Search
CPC ................................................... G16C 20/30

USPC .......................................................... 703/13
See application file for complete search history.

(56) References Cited

U.S. PATENT DOCUMENTS 8,180,617 B1 * 5/2012 Klee .................... G01N 27/00
                                                    703/13

OTHER PUBLICATIONS

Chabay et al., Matter and Interactions, vol. II: Electric and Magnetic Interactions, 4th Edition, Wiley, Hoboken, New Jersey, 2015, Chapters 14 and 18, pp. i-xvi, 546-587, 716-764, and I-I10.

Makarov et al., Low-Frequency Electromagnetic Modeling for Electrical and Biological Systems Using MATLAB, Wiley, Hoboken, New Jersey, 2016, Chapters 1-6, 8-9, and 11-12, Kindle locations 1-381, 419-521, 587-689, and 797-817, hardcover pp. i-xviii, 1-255, 289-370, 423-505, and 591-598.

* cited by examiner

*Primary Examiner* — Timothy A Mudrick

(57) ABSTRACT

Improved computer-implemented tools for use in modeling/simulating spatial charge distributions for electrophysiological systems are provided. The improvements are in three areas: (1) the use of solid angles to calculate quantities of free charge and/or bound charge in calculation cells and/or the movement of quantities of free charge across one or more faces of a calculation cell; (2) the use of flattened calculations cells having only two faces with substantial areas as seen from the free charge and/or the bound charge of the electrophysiological system; and (3) the use of at least two spatial charge distributions, specifically, at least one for bound charge and at least one for free charge, so as to include the effects of relative dielectric constants greater than 1.0 for part or all of an electrophysiological system. The three improvements can be used individually or in combinations.

17 Claims, 18 Drawing Sheets

```
┌─────────────────────────────────────────────────────┐
│ Using the calculation start condition established during │
│ simulation setup (FIG. 3), set the charge distribution at $t_0$ equal │
│ to the starting charge distribution. │
└─────────────────────────────────────────────────────┘
                          ↓
┌─────────────────────────────────────────────────────┐
│ Using the system geometry and symmetry established during │
│ simulation setup (FIG. 3), define the portion of the system over │
│ which iterations are to be performed. │
└─────────────────────────────────────────────────────┘
                          ↓
┌─────────────────────────────────────────────────────┐
│ Progress through the calculation cells of the defined portion of │
│ the system calculating values for the free charge distribution at │
│ $t_{n+1}$ based on values for the free charge distribution at $t_n$ using │
│ the electrical parameters established during simulation setup │
│ (FIG. 3), the solid angle values (FIG. 4), and, for example, │
│ Eqs. (27), (28), and (30). │
└─────────────────────────────────────────────────────┘
                          ↓
                  ◇ Output criterion satisfied? ──Y──▶ Output final or intermediate results.
                          │ N
                          ↓
                  ◇ Termination criterion satisfied? ──N──▶ Replace free charge distribution at $t_n$ with free charge distribution calculated for $t_{n+1}$.
                          │ Y
                          ↓
                        ( End )
```

FIG. 5

COMPUTER-IMPLEMENTED TOOLS FOR USE IN ELECTROPHYSIOLOGY

CROSS-REFERENCE TO RELATED APPLICATION

This application is a continuation of co-pending U.S. application Ser. No. 15/097,379 filed Apr. 13, 2016, the contents of which in its entirety is hereby incorporated by reference. This application also claims the benefit under 35 USC § 119(e) of U.S. Provisional Application No. 62/150,453 filed on Apr. 21, 2015, the contents of which in its entirety is hereby incorporated by reference.

FIELD

This disclosure relates to electrophysiology and, in particular, to computer-implemented tools for analyzing and interpreting electrophysiological data, designing electrophysiological experiments, and discovering heretofore unknown mechanisms and phenomena of electrophysiological systems.

BACKGROUND AND SUMMARY

This disclosure provides improvements to the modeling/simulation processes of U.S. Pat. Nos. 8,180,617 and 8,706,466 (hereinafter the '617/'466 patents), the contents of both of which are incorporated herein by reference in their entireties.

The improvements are directed to modeling/simulating at least a portion of an electrophysiological system and are in three areas: (1) the use of solid angles to calculate quantities of free charge and/or bound charge in calculation cells and/or the movement of quantities of free charge across one or more faces of a calculation cell (hereinafter referred to as the "solid angle process" or the "$\Omega$ process"); (2) the use of flattened calculations cells having only two faces with substantial areas as seen from the free charge and/or the bound charge of the electrophysiological system (hereinafter referred to as the "flattened calculation cell process" or the "$\delta \to 0$ process"); and (3) the use of at least two spatial charge distributions, specifically, at least one for bound charge and at least one for free charge, so as to include the effects of relative dielectric constants greater than 1.0 for part or all of the electrophysiological system (hereinafter referred to as the "bound charge/free charge process").

In each of the improvements, at least one spatial charge distribution is modeled/simulated without first determining and differentiating an electrical potential. The three improvements can be used individually or in combinations. To avoid the need to deal with singularities arising from Equations (1) and (2) of the '617/'466 patents as a calculation cell is flattened (i.e., as two faces of a calculation cell approach one another; see below and FIG. 1), it is generally preferred to use the first improvement when practicing the second improvement. When used together, the first and second improvements are referred to as the "$\Omega\delta \to 0$ processes".

As a result of the first improvement, the number of calculation cells needed to model/simulate an electrophysiological system or a portion thereof can be substantially reduced. In particular, as shown in connection with Eqs. (5) and (6) below, calculation cells do not need to be placed at locations having the following properties: (1) the locations are within the body of a conductor, dielectric, or conductor/dielectric, i.e., the locations are not at interfaces between materials having different properties; (2) the locations have material properties that are isotropic; (3) the locations have no charges at the beginning of the modeling/simulation; and (4) during the course of the modeling/simulation, the locations do not receive charges as applied charges and/or as the result of the direct action of non-conservative fields.

Calculation cells are not required at locations having these properties because there being no charges at the beginning of the modeling/simulation and no charges introduced thereafter, any calculation cell placed at the location will have zero charges for all times. Specifically, for such a calculation cell, because solid angle calculations are used, there will be no net response to quantities of charges in other calculation cells (the external-to-the-calculation-cell charges) since all charges that move into such a calculation cell through one or more of its faces as a result of such external charges will exit the calculation cell through one or more of its other faces. Consequently, such a calculation cell will never have any charge and therefore it will never have an effect on charges in other calculation cells. For these reasons, there is no need to include such "always empty" calculation cells during the modeling/simulation and in accordance with a preferred embodiment of the first improvement, such "always empty" cells are not included in the modeling/simulation.

It should be noted, however, that the presence of such "always empty" calculation cells does no harm and thus if computer storage requirements and computation times are not of concern for the electrophysiological system being analyzed, such cells can be included in the modeling/simulation if desired. For example, in Example 1 below, "always empty" calculation cells were included in the calculations in order to illustrate the ability of the solid angle process to substantially completely eliminate the low levels of internal charges seen when Equations (1) and (2) of the '617/'466 patents, rather than the solid angle process, is used to move quantities of charge between calculation cells.

Quantitatively, if the number of cells needed to perform the modeling/simulation without the first improvement is of order $n^3$, then with the improvement, the number will be of order $n^2$ for large n. Even for the relatively modest number of calculation cells used in the examples, the ability to skip "always empty" cells results in a substantial reduction in the number of cells needed for a simulation. For example, in Example 1, 8405 cubic calculation cells (41×41×5) can be reduced by 54% to 3,842 cells by skipping internal (always empty) calculation cells. Many of the remaining examples employ a conductor or dielectric or conductor/dielectric in the form of a cube having six surfaces. Each surface of the cube is divided into 41×41 square-shaped, flattened calculation cells giving a total of 10,086 cells (41×41×6). If the solid angle process had not been used and internal calculation cells needed to be included in the simulation, the number of cells required would have been 68,921 (41×41×41) cells or essentially seven times as many.

The second improvement, i.e., the flattened calculation cell process, also improves the efficiency of the computation tools of the '617/'466 patents. Rather than reducing the number of calculation cells that needs to be considered, this improvement involves reducing the number of faces of a calculation cell at which computations need to be performed. This improvement focuses on the calculation cells that are located at an interface between two media. In accordance with the preferred embodiment of the first improvement discussed above in which calculations are not performed for "always empty" cells, in certain embodiments, such interface calculation cells will be the great majority and, in many cases, all or essentially all of the calculation cells at which calculations are performed.

For ease of presentation, we will treat the case of a cubic calculation cell, the same analysis being applicable to calculation cells having other configurations. FIG. 1 shows such a cubic calculation cell designated cell A, where face ab is at the interface, face a looks out into the medium containing cell A and faces c through f look towards neighboring calculation cells at the interface and in the same medium. Whether one uses the first improvement disclosed herein, i.e., the solid angle process, or uses Equations (1) and (2) of the '617/'466 patents, for each quantity of charge in the electrophysiological system, six calculations are in general required for a cubic calculation cell, i.e., one calculation for each of faces a, ab, and c through f of the cell. Six calculations are required because each face is at a different location in space. From symmetry considerations, some reduction and/or simplification of the calculations can be achieved for the quantity of charge in the calculation cell of interest (the "target cell") and for quantities of charge in calculation cells that are immediate neighbors of the target cell, but for most of the charges in the system, a calculation, e.g., a solid angle calculation, is needed for the interaction of each quantity of charge with each of the six faces of the target cell. Such a calculation for the interaction of a single quantity of charge with a single face will be referred to herein as an "ab initio calculation" since the calculation is not based on a previous interaction calculation.

In accordance with the second improvement, in an embodiment, only a single ab initio calculation is needed for each calculation cell for each quantity of charge, e.g., a single solid angle calculation. This is so irrespective of whether the quantity of charge is in the target cell or outside that cell. Specifically, in accordance with the flattened cell process, the distance δ in FIG. 1 between faces a and ab is reduced in size, thus bringing those faces into substantially the same location (mathematically, to the same location) while at the same time reducing the areas of faces c through f (mathematically, to zero).

As a consequence of the reduction in the areas of faces c through f, quantities of charge only interact with faces a and ab and thus calculations are only needed for those faces. As to faces a and ab, only a single ab initio calculation is needed because, as δ becomes small, those faces are at substantially the same location, the only difference between the faces being their orientation with respect to the quantity of charge whose interaction with the face is to be determined, i.e., whether the quantity of charge "sees" the inward or outward side of the face. The orientations of faces a and ab determine the sign, but not the magnitude, of the interaction with the quantity of charge. Hence, only a single ab initio calculation of the interaction is needed with the sign applied to the interaction being selected based on an examination of the location of the quantity of charge relative to faces a and ab or a simple calculation based on the angle between a vector from the quantity of charge to the face and the outward normal at the face (see discussion below in connection with Eq. (1)).

In accordance with this embodiment, if one calculates the interactions of the quantities of charge in the system with one of the faces of a flattened calculation cell (the initial set of ab initio calculations) then the interactions of those quantities of charge with the other face of the flattened calculation cell can be determined from the initial set of ab initio calculations without the need for further ab initio calculations. Moreover, if that flattened calculation cell is a member of a pair of flattened calculation cells on either side of an interface between two media having different electrical properties (see FIG. 2), then the one set of ab initio calculations can be used for the faces of the other member of the pair, again without the need for further ab initio calculations.

If desired, more than one ab initio calculation can be performed for some or all flattened calculation cells. Although this will not take full advantage of the flattened calculation process, it will still reduce the number of calculations that need to be performed, e.g., from 6 to 2 for cubic calculation cells.

In addition to making the calculations more efficient, the second improvement also allows for more accurate modeling of both simple and complex geometries. With regard to simple geometries, by flattening the calculation cells, the behavior of a planar surface can be more accurately represented by the modeling/simulation because neighboring calculation cells lying in a common plane do not interact with one another. This can be seen most easily when solid angles are used to express the interaction. As seen from a quantity of charge in a plane, the face of a flattened calculation cell lying in the same plane has zero solid angle. Thus, the quantity of charge cannot cause any charge to pass through the face, i.e., the quantity of charge does not cause charges to accumulate in a target flattened calculation cell in the same plane. As a consequence, these "same plane" interactions can be automatically skipped (just like the "always empty" cells), thus providing additional efficiency to the modeling/simulating process.

With regard to complex geometries, by flattening calculation cells so that they have only two significant faces at substantially the same location, the calculation cells can be treated as pixels in a two-dimensional space rather than voxels in a three dimensional space. Considered as pixels, the calculation cells can freely take on a variety of densities, sizes, and/or shapes, e.g., square, triangular, or hexagonal shapes, and the modeling/simulation process can take advantage of sophisticated meshing techniques of the type developed in connection with the display of the surfaces of three-dimensional objects. For example, different types of calculation cells can be used for different parts of the system being simulated, e.g., smaller calculation cells can be used when modeling the opposing surfaces of thin biological membranes and larger calculation cells can be used when modeling all or parts of the surfaces that form the outer boundary of the system.

Turning to the third improvement, as discussed below in connection with Eqs. (71)-(98), in accordance with this improvement, the dielectric properties of electrophysiological systems are modeled/simulated using bound and free charge distributions which in certain embodiments are alternately determined, i.e., determined one after the other, subject to different assumptions. Specifically, the bound charge distribution is treated as responding (relaxing) much more rapidly than the free charge distribution. Based on this treatment, in proceeding from time step $t_n$ to time step $t_{n+1}$, the bound charge distribution at time step $t_{n+1}$ is calculated first. During this calculation, the free charge distribution is assumed to retain its distribution at time step $t_n$. Then, the free charge distribution is moved forward to its distribution at time step $t_{n+1}$ based on (1) the free charge distribution at time step $t_n$ and (2) the newly-calculated bound charge distribution at time step $t_{n+1}$. The process is then repeated, i.e., a new bound charge distribution for time step $t_{n+2}$ is calculated using the free charge distribution at time step $t_{n+1}$ and then a new free charge distribution for time step $t_{n+2}$ is calculated using the free charge distribution for time step $t_{n+1}$ and the bound charge distribution for time step $t_{n+2}$.

Further iterations following the same pattern are performed until the modeling/simulating is terminated based on a termination (quitting) criterion, e.g., an upper limit on the number of iterations, the attainment of steady state, the attainment of an extrapolatable behavior for the charge distributions, or such other criterion that the user may impose. It should be noted that these iterations, which are also referred to herein as time steps, are different from the iterations used to determine steady state free charge distributions and bound charge distributions using iterative techniques such as Jacobi iteration; see, for example, the discussion following Eqs. (41)-(44) and the Jacobi iterations at multiple time steps of Example 5 below.

Additional aspects and advantages of the technology disclosed herein are set forth in the detailed description that follows, and in part will be readily apparent to those skilled in the art from that description or recognized by practicing the technology as described herein. The accompanying drawings are included to provide a further understanding of the technology, and are incorporated in and constitute a part of this specification. It is to be understood that the various aspects of the technology disclosed in this specification and in the drawings can be used individually and in any and all combinations. It is also to be understood that the general description set forth above and the detailed description which follows are merely exemplary of the invention and are intended to provide an overview or framework for understanding the nature and character of the invention as defined by the claims.

BRIEF DESCRIPTION OF THE DRAWINGS

FIG. 5 is a representative flow chart for a conductor simulation in accordance with an embodiment of the disclosure.

DETAILED DESCRIPTION AND PREFERRED EMBODIMENTS

Figure 1:
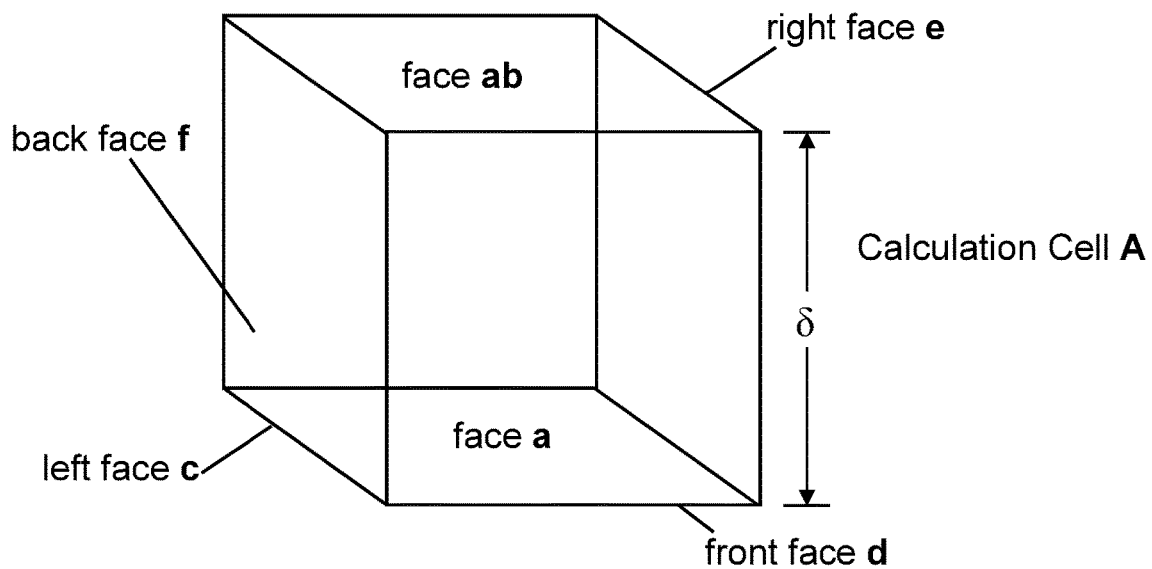
FIG. 1 is a schematic diagram of a representative calculation cell in accordance with an embodiment of the disclosure.

As discussed above, the present disclosure relates to three improvements to the modeling/simulation processes of the '617/'466 patents that are referred to herein as the solid angle process, the flattened calculation cell process, and the bound charge/free charge process. In order to simplify the notation, we will first discuss the first and second improvements assuming the relative dielectric constant is equal to 1.0 throughout the system so that there are only quantities of free charge and no quantities of bound charge, and will then turn to a discussion of the third improvement where the relative dielectric constant can be greater than 1.0 for at least one part of the system so that there can be quantities of bound charge.

I. Ω PROCESS

In accordance with an embodiment of the first improvement, quantities of free charge are moved across faces of calculation cells using an equation of the form:

$$\Delta q^f_j = -(\Delta t/4\pi\varepsilon_0)(\sigma_j)(\Sigma_i q^f_i \Omega_{j\leftarrow i}) \quad (1)$$

where:
(i) $\Delta q^f_j$ is the quantity of free charge moved across the $j^{th}$ face and into the calculation cell in a time step $\Delta t$,
(ii) $\sigma_j$ is the smaller of the calculation cell conductivities on the inside and outside of the $j^{th}$ face,
(iii) $q^f_i$ is the quantity of free charge in coulombs in the $i^{th}$ calculation cell, said quantity of charge, in an embodiment, being concentrated at the center of the calculation cell so as to simplify the calculations (it should be noted that the word "quantity" when used in conjunction with the word "charge" as in the phrase "quantity of charge" is not merely the magnitude of the charge but also includes its sign; it should also be noted that when extended to dielectrics, the summation of Eq. (1) will include both free and bound charges),
(iv) $\varepsilon_0$ is the dielectric constant of free space ($\varepsilon_0 \approx 8.85 \times 10^{-12}$ farads/meter in SI units),
(v) the summation is over all of the calculation cells that contain quantities of free charge which includes:
   (a) the calculation cell that includes the $j^{th}$ face (the self-term),
   (b) all calculation cells in the system that at the time $\Delta q^f_j$ is calculated contain a quantity of free charge, e.g., because the cell accumulated a quantity of free charge as a result of being at an interface between two materials having different conductivities and/or because the cell contains a quantity of free charge because of anisotropic conductivity, and/or because the cell contains a quantity of fixed charge, and/or because the cell received and still retains a quantity of applied free charge and/or a quantity of free charge resulting from the direct action of non-conservative fields, and
(vi) $\Omega_{j\leftarrow i}$ is the solid angle of the $j^{th}$ face as seen from the $i^{th}$ quantity of charge, the solid angle being positive when the $i^{th}$ quantity of charge sees the inward side of the $j^{th}$ face and negative when it sees the outward side where "inward" and "outward" are relative to the internal volume of the calculation cell or, equivalently, $\Omega_{j\leftarrow i}$ is positive when the angle between a vector from the $i^{th}$ quantity of charge to the center of the $j^{th}$ face makes an acute angle with an outward normal to the $j^{th}$ face and negative when that angle is obtuse where again the outward normal is relative to the internal volume of the calculation cell. (Note that the left facing arrow, i.e., ←, is used to indicate that the $i^{th}$ quantity of charge is "looking at" the $j^{th}$ face.)

Numerous techniques based on spherical trigonometry are known for determining solid angles and can be used in connection with Eq. (1). See, for example, Harding, A. M. "The Apparent Size of a Cube." *The American Mathematical Monthly*. 21, 209-219, 1914.

The total quantity of free charge $\Delta q^f_i$ moved into a calculation cell during a time step $\Delta t$ is then:

$$\Delta q^f_i = \Sigma_j \Delta q^f_j = -(\Delta t/4\pi\varepsilon_0)\Sigma_j(\sigma_j)(\Sigma_i q^f_i \Omega_{j\leftarrow i}) + I^f_i \Delta t, \quad (2)$$

where (1) the j summation is over all of the faces of the calculation cell, e.g., j goes from one to six for a cubic calculation cell, (2) as in Eq. (1), the i summation is over all of the calculation cells that contain quantities of free charge at the time $\Delta q^f_i$ is calculated, and (3) $I^f_i \Delta t$ represents a quantity of free charge imposed (added or subtracted) to the $i^{th}$ calculation cell during the time step $\Delta t$, i.e., $I^f_i \Delta t$ represents a quantity of free charge directly introduced into the $i^{th}$ calculation cell such as a quantity of applied free charge or a quantity of free charge arising from the direct action of non-conservative fields.

In the discussion below, especially in connection with the discussion of matrix notation (see, for example, Eqs. (41)-(44)), it will be convenient to distinguish between (1) quantities of imposed free charges that are subject to redistribution by conduction during the simulation, such as quantities of imposed free charge represented by $I^f_i \Delta t$, and (2) quantities of imposed free charge that are not subject to such redistribution, i.e., quantities of free charge that are spatially stationary (non-redistributable) because they are in calculation cells with zero conductivity. We will designate these latter quantities of charge as s charges to indicate that they serve as "spatially stationary sources" that do not redistribute through conduction. A non-limiting example of such s charge is the quantity of charge of the point source outside a slab in Example 1 and a cube in Examples 3-5 below. Other non-limiting examples are quantities of fixed charge, such as the fixed charges associated with charged amino acids, e.g., the charged amino acids of the proteins that form pores through biological membranes. It should be noted that s charges, as well as $I^f_i$'s, can be time invariant or can change over time.

With the introduction of the s nomenclature to represent non-redistributable free charge, in all subsequent equations of this disclosure, the superscript f will be limited to redistributable free charge. Using this convention, Eqs. (1) and (2) become:

$$\Delta q^f_j = -(\Delta t/4\pi\varepsilon_0)(\sigma_j)(\Sigma_i q^f_i \Omega_{j\leftarrow i} + \Sigma_k q^s_k \Omega_{j\leftarrow k}), \text{ and} \quad (3)$$

$$\Delta q^f_i = -(\Delta t/4\pi\varepsilon_0)\Sigma_j(\sigma_j)(\Sigma_i q^f_i \Omega_{j\leftarrow i} + \Sigma_k q^s_k \Omega_{j\leftarrow k}) + I^f_i \Delta t, \quad (4)$$

where the i and k summations are over calculation cells which are conductive and non-conductive, respectively.

As can be seen from Eq. (4), the change in the quantity of redistributable free charge in the $i^{th}$ calculation cell depends on the quantity of redistributable free charge currently in that cell. Thus, the quantity of redistributable free charge in the $i^{th}$ calculation cell feeds back on itself and in many cases, depending on the $I^f_i$ for the given calculation cell, the $I^f_i$'s for the other calculation cells of the system, and the s charges, can eventually stop changing when the movement of free charge across the faces of the $i^{th}$ calculation cell caused by the quantity of free charge in the $i^{th}$ calculation cell balances the movement of free charge into or out of the $i^{th}$ calculation cell caused by the other quantities of charge in the system. See, for example, Eqs. (33)-(44) below.

As an aside, it is of interest to note that Eqs. (1)-(4) depend on the geometry (shape) of the system through the $\Omega$ values, but not on the size (characteristic dimension) of the system. That is, for a fixed number of calculation cells at fixed relative locations, changing the size of the calculation cells and thus the system does not change the $\Delta q$'s since the $\Omega$ values remain constant with a change in scale. This can also be seen by considering electric fluxes. For example, if all distances in a system are increased by the multiplicative factor x, surface areas will increase by $x^2$ and the strengths of electric fields at those surface areas will decrease by $1/x^2$. The flux through any surface will therefore remain unchanged because the flux depends on the product of area and electric field strength.

In terms of biological function, scale invariance provides a mechanism by which biological cells having substantially the same shape can operate in substantially the same manner even if they have different sizes, e.g., small pyramidal cells can process inputs of the same strength in substantially the same manner as large pyramidal cells. All that needs to be assumed is that the receptor density on the membrane of any structure of interest, e.g., the receptor density on the membrane of a neuron's axon hillock, remains constant as the size of the biological cell scales. The probability of interaction between a membrane receptor and a charged species as a result of electrical inputs of the same strength to the biological cell, e.g., from excitatory and inhibitory synapses modeled as current sources, will then remain constant with a change in the size of the biological cell. That is, if the number of signaling molecules per unit area goes down because of the larger dimensions, but the total number of receptors goes up because of the increased area, then the probability of a signaling molecule binding with a receptor remains constant.

This can be seen by considering, as a specific example, a doubling of the size of a biological cell. The $\Delta q$'s at the cell's membrane due to electrical inputs will not change with such a doubling because of the $\Omega$ invariance. However, $\Delta q$ per unit area will decrease by a factor of four since the membrane area of the structure of interest, e.g., the axon hillock, will increase by a factor of four with the doubling in size. This would seem to make it less likely that there would be an interaction. However, if the receptor density remains constant, the increase in the membrane area by a factor of four means that the number of receptors associated with the structure of interest increases by a factor of four, thus bringing the probability of interaction back to what it was for the smaller biological cell. With the probability unchanged, the cell function will be the same thus allowing small and large biological cells having the same shape to operate in the same manner.

Another way of considering this effect is to define biologically significant "landmarks" or "landmark regions." For example, the axon hillock can be thought of as a landmark region. The total quantity of charge in a landmark region (the landmark charge) will be the same irrespective of the size of a cell if the cell viewed as an electrical medium has the same shape and conductivity and if the source charge which induces the charge distribution is constant. As noted above, the source charge can, for example, be an active synapse modeled as a current source. While the total quantity of charge in the landmark region is constant irrespective of the scale, the charge density is not constant, i.e., it is proportional to $1/x^2$ where x is the scale. However, if the number of receptors per unit area is constant, then the total number of receptors for the landmark region scales as $x^2$. The product of total receptors times charge density is then a constant, thus allowing the functioning of the cell to be independent of size. It should be noted that these same considerations regarding scaling also apply to bound charge.

Unlike free and bound charges, potential values calculated from charge distributions (see, for example, Eq. (99) below) do not scale because they depend on $1/r$ instead as $1/r^2$. Conversely, sources defined in terms of potentials, e.g., Nernst potentials, instead of applied charges or applied currents, do not scale. Example 6 below is such a non-scaling example, the source being an array of dipoles whose strengths are based on a predetermined potential such as a Nernst potential. Example 2 of the '617/'466 patents was also of this type, i.e., the source was defined in terms of a potential (a Nernst potential) instead of applied charges or applied currents. In both cases, the fields produced by the sources do not vary as $1/r^2$, the field varying as $1/r^3$ in Example 6 (see Eq. (122) below) and varying as $1/r$ in the case of Example 2 of the '617/'466 patents (see Equations (5) and (6) of the '617/'466 patents). Hence, for a fixed applied potential, the $\Delta q$'s do not remain constant as the system is scaled.

Returning to Eq. (4), the basis for "always empty" calculation cells can be seen from that equation as follows. By assumption, $\sigma_j$ is the same for all faces, i.e., the conductivity is assumed to be isotropic at the location of the "always empty" calculation cell, so that Eq. (4) can be written:

$$\Delta q^f_{AE} = -(\sigma\Delta t/4\pi\varepsilon_0)\Sigma_j(\Sigma_i q^f_i \Omega_{j\leftarrow i} + \Sigma_{k\neq AE} q^s_k \Omega_{j\leftarrow k}), \quad (5)$$

where $\sigma$ is the common conductivity at all of the faces of the AE (always empty) cell. In Eq. (5), $I^f_i \Delta t$ of Eq. (4) has been set equal to zero and the AE cell has been omitted from the second summation (the s charge summation) since by assumption there are no imposed free charges for AE cells. Interchanging the order of the summations in Eq. (5) then gives:

$$\Delta q^f_{AE} = -(\sigma\Delta t/4\pi\varepsilon_0)(\Sigma_i q^f_i \Sigma_j \Omega_{j\leftarrow i} + \Sigma_{k\neq AE} q^s_k \Sigma_j \Omega_{j\leftarrow k}). \quad (6)$$

By assumption, all of the $q^f_i$'s are initially outside of the AE cell. Consequently, for each i, $\Sigma_j \Omega_{j\leftarrow i}$ constitutes the solid angle of a closed surface (i.e., the entire calculation cell as j takes on the values for all of the faces of the cell) as seen from a point outside of the surface, i.e., the location of the $i^{th}$ quantity of free charge. The same is true for the $q^s_k$'s since they too are outside of the AE cell. As shown in, for example, Phillips, H. B., *Vector Analysis*, New York, N.Y., John Wiley, 1933, page 114, the solid angle of a closed surface as seen from a point outside of the surface is zero. Accordingly, $\Delta q^f_{AE}$ is always zero thus making the total quantity of free charge $q^f_{AE}$ in the AE cell always zero since by assumption the AE cell starts out with no free charge and does not receive imposed free charges during the simulation. It should be noted that the same considerations apply to quantities of bound charge, i.e., subject to the same assumptions, an "always empty" cell for free charges is also an "always empty" cell for bound charges.

II. $\Omega\delta \to 0$ PROCESSES

Figure 2:
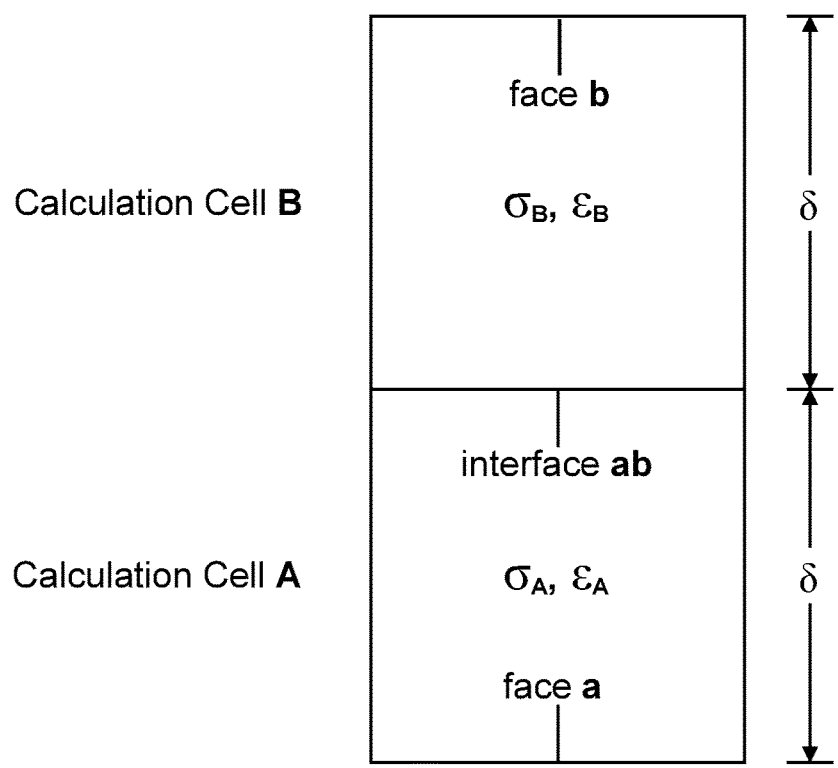
FIG. 2 is a schematic, cross-sectional diagram of two representative calculation cells which meet at an interface in accordance with an embodiment of the disclosure.

Turning to embodiments of the second improvement of the present disclosure, i.e., the flattened calculation cell process, FIG. 2 shows a cross-section through two representative calculation cells A and B on opposite sides of an interface which separates an isotropic medium having a conductivity $\sigma_A$ from an isotropic medium having a conductivity $\sigma_B$ where, this being an interface, $\sigma_A \neq \sigma_B$. As the thickness $\delta$ of these interface calculation cells is reduced in size, i.e., as the calculation cells are flattened, the only faces of cells A and B that continue to have substantial solid angles as seen from the quantities of charge in the system are the lower face a of cell A, the upper face b of cell B, and the interface face ab between the two cells. Those solid angles will be referred to as $\Omega_{a \leftarrow i}$, $\Omega_{b \leftarrow i}$, and $\Omega_{ab \leftarrow i}$, respectively, for the redistributable free charges (f charges) and as $\Omega_{a \leftarrow k}$, $\Omega_{b \leftarrow k}$, and $\Omega_{ab \leftarrow k}$ for the non-redistributable free charges (s charges). The relationships among and the values of these solid angles will be derived for the i index, it being understood that the same relationships and values apply to the k index.

For each quantity of charge in the system, the magnitudes of the solid angles at faces a, b, and ab become equal as $\delta$ is reduced in size because the locations of the faces become the same, i.e., for a quantity of charge in calculation cell i:

$$|\Omega_{a \leftarrow i}| = |\Omega_{b \leftarrow i}| = |\Omega_{ab \leftarrow i}|. \tag{7}$$

Furthermore, for quantities of charge in cells A and B, as $\delta \to 0$, the solid angles of faces a, b, and ab each approach $2\pi$:

$$|\Omega_{a \leftarrow A}| = |\Omega_{b \leftarrow A}| = |\Omega_{ab \leftarrow A}| = |\Omega_{a \leftarrow B}| = |\Omega_{b \leftarrow B}| = |\Omega_{ab \leftarrow B}| = 2\pi. \tag{8}$$

Reducing the size of $\delta$, however, does not change the signs of the solid angles which remain the same as they were prior to flattening. In particular, for any given quantity of charge, the sign of the solid angle continues to depend on whether the quantity of charge "sees" the inside or the outside of the face relative to the internal volume of the calculation cell. Consequently, taking, for example, $\Omega_{a \leftarrow i}$ as the reference solid angle, we have the following relationships for a quantity of charge external to cells A and B:

$$\Omega_{b \leftarrow i} = -\Omega_{a \leftarrow i}, \tag{9}$$

$$\Omega_{ab \leftarrow i} = -\Omega_{a \leftarrow i} \text{ when interface face } ab \text{ is part of cell } A, \text{ and} \tag{10}$$

$$\Omega_{ab \leftarrow i} = +\Omega_{a \leftarrow i} \text{ when interface face } ab \text{ is part of cell } B. \tag{11}$$

Further, for a quantity of charge in cell A and interface face ab a part of cell A, we have:

$$\Omega_{ab \leftarrow A} = \Omega_{a \leftarrow A} = \Omega_{b \leftarrow A} = +2\pi, \tag{12}$$

and for a quantity of charge in cell B and interface face ab part of cell B, we likewise have:

$$\Omega_{ab \leftarrow B} = \Omega_{b \leftarrow B} = \Omega_{a \leftarrow B} = +2\pi. \tag{13}$$

The relationships of Eqs. (9)-(13) greatly simplify the determination of spatial charge distributions at interfaces between materials having different properties. In particular, as will now be shown, for conductors having different conductivities, quantities of free charge only accumulate on the higher conductivity side of such an interface and the quantity of free charge that accumulates depends on the difference in conductivity at the interface, i.e., $\sigma_{\text{diff}} = \sigma_A - \sigma_B$, where we will assume that $\sigma_A > \sigma_B$. Before turning to that showing, we note that relationships equivalent to those of Eqs. (9)-(13) can be derived using $\Omega_{b \leftarrow i}$ or one of the $\Omega_{ab \leftarrow i}$'s as the reference solid angle instead of $\Omega_{a \leftarrow i}$, and then those equivalent relationships can be used to derive the equations that follow in terms of the alternative reference solid angle. Also, as noted above, the second improvement can be practiced without taking advantage of the relationship between the solid angles of the two faces of a flattened calculation cell, if desired. Specifically, ab initio calculations can be performed for each face if desired.

Using Eq. (4) and recalling that $\sigma_j$ in that equation is the smaller of the conductivities on the inside and outside of the $j^{th}$ face, we can write the following equations for representative interface cells A and B, where we have assumed that $\sigma_A$ and $\sigma_B$ are both greater than zero so that these cells do not contain s charge:

$$\Delta q^f_A = -(\Delta t / 4\pi\varepsilon_0)\left(\sigma_A \sum_{i \neq A} q^f_i \Omega_{a \leftarrow i} + \sigma_B \sum_{i \neq A} q^f_i \Omega_{ab \leftarrow i} + \sigma_A q^f_A \Omega_{a \leftarrow A} + \sigma_B q^f_A \Omega_{ab \leftarrow A}\right) - (\Delta t / 4\pi\varepsilon_0)\left(\sigma_A \sum_{k \neq A,B} q^s_k \Omega_{a \leftarrow k} + \sigma_B \sum_{k \neq A,B} q^s_k \Omega_{ab \leftarrow k}\right) + I^f_A \Delta t, \tag{14}$$

and $$\Delta q^f_B = -(\Delta t / 4\pi\varepsilon_0)\left(\sigma_B \sum_{i \neq B} q^f_i \Omega_{b \leftarrow i} + \sigma_B \sum_{i \neq B} q^f_i \Omega_{ab \leftarrow i} + \sigma_B q^f_B \Omega_{b \leftarrow B} + \sigma_B q^f_B \Omega_{ab \leftarrow B}\right) - (\Delta t / 4\pi\varepsilon_0)\left(\sigma_B \sum_{k \neq A,B} q^s_k \Omega_{b \leftarrow k} + \sigma_B \sum_{k \neq A,B} q^s_k \Omega_{ab \leftarrow k}\right) + I^f_B \Delta t. \tag{15}$$

Rewriting these equations in terms of $\Omega_{a \leftarrow i}$ and using the relationships of Eqs. (9)-(13) for the solid angles at faces a, b, and ab, we have:

$$\Delta q^f_A = -(\Delta t / 4\pi\varepsilon_0)\left((\sigma_A - \sigma_B) \sum_{i \neq A} q^f_i \Omega_{a \leftarrow i} + 2\pi q^f_A (\sigma_A + \sigma_B)\right) - (\Delta t / 4\pi\varepsilon_0)(\sigma_A - \sigma_B) \sum_{k \neq A,B} q^s_k \Omega_{a \leftarrow k} + I^f_A \Delta t, \tag{16}$$

and $$\Delta q^f_B = -(\Delta t / 4\pi\varepsilon_0)(4\pi q^f_B \sigma_B) + I^f_B \Delta t. \tag{17}$$

Finally, using the above definition of $\sigma_{diff}$ and defining $\sigma_{sum}$ as the sum of $\sigma_A$ and $\sigma_B$, we obtain:

$$\Delta q_A^f = -\Delta t \left[ (\sigma_{diff}/4\pi\varepsilon_0) \sum_{i \neq A} q_i^f \Omega_{a \leftarrow i} + (\sigma_{sum}/2\varepsilon_0) q_A^f \right] - \quad (18)$$

$$\Delta t \left[ (\sigma_{diff}/4\pi\varepsilon_0) \sum_{k \neq A,B} q_k^s \Omega_{a \leftarrow k} - I_A^f \right],$$

and $$\Delta q_B^f = -\Delta t \left[ (\sigma_B/\varepsilon_0) q_B^f - I_B^f \right]. \quad (19)$$

It should be noted that for the quantity of redistributable free charge in cell A, the first summation in Eq. (18) (the i summation) excludes $q_A^f$ but includes $q_B^f$ for so long as cell B has a quantity of redistributable free charge and also includes quantities of redistributable free charge (if any) in lower conductivity calculation cells other than the cell B directly across the interface from cell A (hereinafter all such lower conductivity calculation cells, including the cell B directly across the interface from cell A, will be referred to collectively as "B-type cells").

The first summation also includes quantities of redistributable free charge not located at an interface between two media, i.e., quantities of redistributable free charge located within the body (interior) of a conductor. Eq. (4) applied to three-dimensional calculation cells, e.g., cubic calculation cells, will normally be used to calculate changes in the quantities of such redistributable free interior charges during a time step $\Delta t$, although flattened calculation cells can be used if desired. Calculation cells which contain interior charges will be referred to as int calculation cells. Such int calculation cells can include quantities of non-redistributable free charge (s charge) when $\sigma_{int}=0$. In such a case, the second summation in Eq. (18) (the k summation) will include those s charges. Table 1 summarizes the f, s, b, A, B, and int nomenclature used herein, where, as will be discussed, b represents bound charge.

In view of the foregoing, in accordance with embodiments of the present disclosure, quantities of free charge can be quantities of: (1) redistributable free interface charge, (2) non-redistributable free interface charge (e.g., when $\sigma_B=0$; see below), (3) redistributable free interior charge, or (4) non-redistributable free interior charge. In terms of the f and s nomenclature, f charges include redistributable free interface charges and redistributable free interior charges and s charges include non-redistributable free interface charges and non-redistributable free interior charges. As will be discussed below in connection with the third improvement, quantities of bound charge can be: (1) bound interface charge or (2) bound interior charge, neither of which is redistributable since, unlike redistributable free charge, neither can redistribute by conduction. As also discussed below, for an isotropic dielectric, bound interior charge is associated with (directly proportional to) free interior charge (either redistributable or non-redistributable) at the same spatial location (see Eqs. (65)-(68)).

From the foregoing, it can be seen that in accordance with an aspect of the disclosure, up to six categories of charge can be used to model/simulate electrophysiological systems. Of course, in any particular simulation, not all of these possible categories need be used and, in general, only some of the categories will be needed. The six categories can be organized in various ways, a particularly helpful one being: charge is treated as having two varieties, bound and free; bound charge is treated as having two varieties, interface and interior; and free charge is treated as having two varieties, redistributable and non-redistributable, each of which is treated as having two varieties, interface and interior, where, for example, "treating" can comprise storing some or all of the varieties in separate arrays and/or files.

It should be noted that the term "interior" does not mean that the charges are within the region of interest but merely that they are within a region as opposed to at an interface between a region and another region. For example, the point source used in Examples 1 and 3-5 below is in air but outside the region of interest which is a conductive slab in Example 1, a conductive cube in Example 3, a dielectric cube in Example 4, and a conductive/dielectric cube in Example 5. This point source is a quantity of non-redistributable free interior charge with no associated bound interior charge because $\varepsilon_r=1$ at the location of the point source. It should also be noted that a calculation cell (either interface or interior) that contains redistributable free charges does not contain non-redistributable free charges and vice versa since at any given point in time a given calculation cell is either conductive or not.

Returning to Eqs. (18) and (19), the net change in the quantity of redistributable free interface charge for the combination of calculation cells A and B during a time step $\Delta t$ can be obtained by adding the two equations together. Defining $\Delta q_{tot}^f = \Delta q_A^f + \Delta q_B^f$ and grouping source-type terms, we have:

$$\Delta q_{tot}^f = -\Delta t \left[ (\sigma_{diff}/4\pi\varepsilon_0) \sum_{i \neq A} q_i^f \Omega_{a \leftarrow i} + (\sigma_{sum}/2\varepsilon_0) q_A^f + (\sigma_B/\varepsilon_0) q_B^f \right] - \quad (20)$$

$$\Delta t \left[ (\sigma_{diff}/4\pi\varepsilon_0) \sum_{k \neq A,B} q_k^s \Omega_{a \leftarrow k} - I_A^f - I_B^f \right],$$

which upon removing $q_B^f$ from the first summation and using Eq. (8) becomes:

$$\Delta q_{tot}^f = -\Delta t \left[ (\sigma_{diff}/4\pi\varepsilon_0) \sum_{i \neq A,B} q_i^f \Omega_{a \leftarrow i} + \quad (21) \right.$$

$$\left. (\sigma_{diff}/4\pi\varepsilon_0) q_B^f 2\pi + (\sigma_{sum}/2\varepsilon_0) q_A^f + (\sigma_B/\varepsilon_0) q_B^f \right] -$$

$$\Delta t \left[ (\sigma_{diff}/4\pi\varepsilon_0) \sum_{k \neq A,B} q_k^s \Omega_{a \leftarrow k} - I_A^f - I_B^f \right].$$

Since $\sigma_{diff} + 2\sigma_B = \sigma_{sum}$, Eq. (21) can be written:

$$\Delta q_{tot}^f = \quad (22)$$

$$-\Delta t \left[ (\sigma_{diff}/4\pi\varepsilon_0) \sum_{i \neq A,B} q_i^f \Omega_{a \leftarrow i} + (\sigma_{sum}/2\varepsilon_0) q_A^f + (\sigma_{sum}/2\varepsilon_0) q_B^f \right] -$$

$$\Delta t \left[ (\sigma_{diff}/4\pi\varepsilon_0) \sum_{k \neq A,B} q_k^s \Omega_{a \leftarrow k} - I_A^f - I_B^f \right].$$

Finally, defining $q_{tot}^f = q_A^f + q_B^f$, we have:

$$\Delta q_{tot}^f = -\Delta t \left[ (\sigma_{diff}/4\pi\varepsilon_0) \sum_{i \neq A,B} q_i^f \Omega_{a \leftarrow i} + (\sigma_{sum}/2\varepsilon_0) q_{tot}^f \right] \quad (23)$$

$$-\Delta t \left[ (\sigma_{diff}/4\pi\varepsilon_0) \sum_{k \neq A,B} q_k^s \Omega_{a \leftarrow k} - I_A^f - I_B^f \right].$$

Eq. (23) was derived by treating calculation cells A and B as being separated from one another by interface ab through which redistributable free charge can pass. The same equation is obtained by treating calculation cells A and B as a single calculation cell (cell AB) without an internal interface. Using Eq. (4), we can write:

$$\Delta q_{AB}^f = -(\Delta t/4\pi\varepsilon_0)\left(\sigma_A \sum_{i\neq AB} q_i^f \Omega_{a\leftarrow i} + \sigma_B \sum_{i\neq AB} q_i^f \Omega_{b\leftarrow i} + \sigma_A q_{AB}^f \Omega_{a\leftarrow AB} + \sigma_B q_{AB}^f \Omega_{b\leftarrow AB}\right)$$
$$-(\Delta t/4\pi\varepsilon_0)\left(\sigma_A \sum_{k\neq AB} q_k^s \Omega_{a\leftarrow k} + \sigma_B \sum_{k\neq AB} q_k^s \Omega_{b\leftarrow k}\right) +$$
$$I_{AB}^f \Delta t, \qquad (24)$$

which using Eqs. (9), (12), and (13) applied to cell AB becomes:

$$\Delta q_{AB}^f = -\Delta t\left[(\sigma_{diff}/4\pi\varepsilon_0)\sum_{i\neq AB} q_i^f \Omega_{a\leftarrow i} + (\sigma_{sum}/2\varepsilon_0)q_{AB}^f\right] \qquad (25)$$
$$-\Delta t\left[(\sigma_{diff}/4\pi\varepsilon_0)\sum_{k\neq AB} q_k^s \Omega_{a\leftarrow k} - I_{AB}^f\right],$$

which, except for notation, is the same as Eq. (23).

As a third option, the net change in the quantity of redistributable free interface charge for cells A and B during a time step $\Delta t$ can be obtained by starting with Eq. (4) and writing equations corresponding to Eqs. (14) and (15) but with interface ab treated as non-conducting, rather than conducting. The result for $\Delta q_{tot}^f$ is again the same as Eq. (23), but the individual $\Delta q^f$'s for cells A and B differ from those of Eqs. (18) and (19), e.g., the equation for $\Delta q_A^f$ uses only $\sigma_A$ rather than depending on $\sigma_{diff}$ and $\sigma_{sum}$ as in Eq. (18). If desired, for the case where $I_B^f = 0$ and $q_B^f(t_0) = 0$, the distribution given by Eqs. (18) and (19) can be obtained by treating the interface as non-conducting and, at the end of each time step, shifting the charges accumulated on the low conductivity side of the interface to the high conductivity side and setting the charges on the low conductivity side to zero.

As an aside, when dealing with dielectrics, although the total quantity of bound charge can be computed at an interface between two dielectric materials having different relative dielectric constants by adding together the quantities of bound charge on the two sides of the interface, because the polarization vector (and thus the displacement vector) has a curl, those two quantities of bound charge are calculated using two separate calculation cells, one on each side of the interface, rather than a single combined calculation cell as in Eq. (25) above (see, for example, the discussion of the use of two K values to represent such an interface in Eqs. (59)-(62) below).

The free charge distribution at the interface between a conductor and a non-conductor is often of interest. For this case, $\sigma_B$ is set equal to zero so that $\sigma_{diff} = \sigma_{sum} = \sigma_A$. Also, for this case, $I_B^f$, $q_B^f$, and $\Delta q_B^f$ are zero since any free charge in cell B is not redistributable, i.e., free charge in cell B (if any) is non-redistributable s charge. Eq. (18) then becomes:

$$\Delta q_{A(\sigma_B=0)}^f = -\Delta t(\sigma_A/2\varepsilon_0)\left[(1/2\pi)\sum_{i\neq A,B} q_{i(\sigma_B=0)}^f \Omega_{a\leftarrow i} + q_{A(\sigma_B=0)}^f\right] \qquad (26)$$
$$-\Delta t\left[(\sigma_A/2\varepsilon_0)(1/2\pi)\sum_{k\neq A} q_k^s \Omega_{a\leftarrow k} - I_A^f\right],$$

where cell B has been explicitly removed from the first summation and reintroduced into the second summation since cell B does not contain f charge but can now contain s charge. Eq. (26) also represents the net change in the quantity of redistributable free charge at interface ab during a time step $\Delta t$ since, as noted above, $q_B^f$ and $\Delta q_B^f$, because they are redistributable charges, are zero for the $\sigma_B=0$ case.

As discussed in the '617/'466 patents (see, for example, FIG. 1B of those patents), the ability to calculate the quantity of charge that moves across the faces of calculation cells during a time step $\Delta t$ allows one to calculate time courses for the charges in electrophysiological systems. Explicitly, from Eqs. (18) and (19), for the solid angle and flattened calculation cell improvements of the present disclosure, we have the following expressions for the quantities of redistributable free interface charge in representative interface cells A and B at time $t_{n+1}$ based on the quantities of free charge at time $t_n$ in those interface calculation cells and the quantities of free charge in the other interface and interior calculation cells used to represent the system:

$$q_A^f(t_{n+1}) = q_A^f(t_n) + \Delta q_A^f \qquad (27)$$
$$= (1 - \Delta t\sigma_{sum}/2\varepsilon_0)q_A^f(t_n) - \Delta t\sigma_{diff}/4\pi\varepsilon_0 \sum_{i\neq A} q_i^f(t_n)$$
$$\Omega_{a\leftarrow i} - \Delta t\left[\sigma_{diff}/4\pi\varepsilon_0 \sum_{k\neq A,B} q_k^s(t_n)\Omega_{a\leftarrow k} - I_A^f(t_n)\right], \text{ and}$$

$$q_B^f(t_{n+1}) = q_B^f(t_n) + \Delta q_B^f = (1 - \Delta t\sigma_B/\varepsilon_0)q_B^f(t_n) + I_B^f(t_n)\Delta t, \qquad (28)$$

where the fact that $q_i^f$, $q_k^s$, $I_A^f$, and/or $I_B^f$ are or can be time dependent has been made explicit. For $t_0$, $q_A^f(t_0)$ and $q_B^f(t_0)$ are the original quantities of free charge in cells A and B at the beginning of the simulation. Likewise, $q_i^f(t_0)$, $q_k^s(t_0)$, $I_A^f(t_0)$, and $I_B^f(t_0)$ are the $q_i^f$, $q_k^s$, $I_A^f$, and $I_B^f$ values at the beginning of the simulation.

Using Eq. (4), and the fact that the solid angle for a quantity of charge outside of a closed surface is zero and $+4\pi$ when inside (Phillips, *Vector Analysis*, supra, page 114), $\Delta q_{int}^f$ for a representative int calculation cell of an isotropic conductor can be written:

$$\Delta q_{int}^f = -(\Delta t\sigma_{int}/\varepsilon_0)q_{int}^f + I_{int}^f \Delta t, \qquad (29)$$

where $\sigma_{int}$ is the conductivity at the location of the quantity of free interior charge and $I_{int}^f$ is the applied free charge at that location (if any). The time course of redistributable free interior charge in such a representative conductive int calculation cell is then:

$$q_{int}^f(t_{n+1}) = q_{int}^f(t_n) + \Delta q_{int}^f = (1 - \Delta t\sigma_{int}/\varepsilon_0)q_{int}^f(t_n) + I_{int}^f(t_n)\Delta t, \qquad (30)$$

where the possibility that $I_{int}^f$ can be time dependent has been made explicit. As with Eqs. (27) and (28), $q_{int}^f(t_0)$ and $I_{int}^f(t_0)$ are the original qint and $I_i^f$ nt values at the beginning of the simulation. If $\sigma_{int}=0$, then the quantity of free interior charge in the int cell is non-redistributable s charge and its time course will depend on whether that s charge is constant or time varying.

By proceeding through all the A and B calculation cells representing the interface or interfaces of the system and all the int calculation cells representing free interior charges, the spatial charge distribution at $t_{n+1}$ is obtained from the spatial charge distribution at $t_n$. The process is then repeated to obtain the spatial charge distribution at $t_{n+2}$ using the spatial charge distribution at $t_{n+1}$ as the starting point, and then the distribution at $t_{n+3}$ starting with the $t_{n+2}$ distribution, and so forth. In this way, the time course of the spatial charge distribution of the system is obtained for as many time steps as desired. It should be noted that for s charges, formal calculation cells are often not needed since the charges are not redistributable and thus can be represented by simply specifying a spatial location for the charge. For example, a formal calculation cell was not used for the point source of Examples 3-5.

From Eqs. (19) and (28), we see that for $V_B^f=0$, the quantity of original free interface charge (if any) in a B cell decays by conduction from the cell with a time constant of $\varepsilon_0/\sigma_B$, and, after the decay, no free charges accumulate in the cell. Any free charge added to the calculation cell as a result of $V_B^f \neq 0$, if not replenished, decays by conduction in the same manner as original free charge. As can be seen from Eq. (30), the same type of behavior occurs for int calculation cells containing quantities of redistributable free interior charge.

The time course of the quantity of redistributable free interface charge in an A cell (Eqs. (18) and (27)) is even more complicated and depends on (1) the sum and the difference of $\sigma_A$ and $\sigma_B$, (2) the quantity of redistributable free charge in cell A, (3) the quantity of redistributable free charge added to cell A when $V_A^f \neq 0$, (4) the distribution of all the other quantities of free charge in the system, i.e., the $q_i^f(t_n)$'s and the $q_k^s(t_n)$'s, and (5) the solid angles of face a of cell A as seen from those other quantities of free charge, i.e., the solid angles $\Omega_{a \leftarrow i}$ and $\Omega_{a \leftarrow k}$.

From Eq. (23) (or Eq. (25)) and Eq. (26), the time courses for $q_{tot}^f$ and $q_{A(\sigma_B=0)}^f$ are:

$$q_{tot}^f(t_{n+1}) = q_{tot}^f(t_n) + \Delta q_{tot}^f \quad (31)$$
$$= (1 - \Delta t \sigma_{sum}/2\varepsilon_0) q_{tot}^f(t_n) - \Delta t \sigma_{diff}/4\pi\varepsilon_0 \sum_{i \neq A,B} q_i^f(t_n)$$
$$\Omega_{a \leftarrow i} - \Delta t \left[ \sigma_{diff}/4\pi\varepsilon_0 \sum_{k \neq A,B} q_k^s(t_n) \Omega_{a \leftarrow k} - V_A^f(t_n) - V_B^f(t_n) \right], \text{ and}$$

$$q_{A(\sigma_B=0)}^f(t_{n+1}) = q_{A(\sigma_B=0)}^f(t_n) + \Delta q_{A(\sigma_B=0)}^f \quad (32)$$
$$= (1 - \Delta t \sigma_A/2\varepsilon_0) q_{A(\sigma_B=0)}^f(t_n) - \Delta t \sigma_A/4\pi\varepsilon_0$$
$$\sum_{i \neq A,B} q_{i(\sigma_B=0)}^f(t_n) \Omega_{a \leftarrow i} - \Delta t \left[ \sigma_A/4\pi\varepsilon_0 \sum_{k \neq A} q_k^s(t_n) \Omega_{a \leftarrow k} - V_A^f(t_n) \right].$$

With regard to the $\sigma_B=0$ case, it should be noted that although the quantity of free charge in cell B cannot change as a result of conduction, the quantity $q_B^s$ of non-redistributable free charge in cell B, which is included in the last summation (the k summation) in Eq. (32), can change when $q_B^s$ is a function of time.

In some cases, the free charge distribution of interest is a steady state distribution (the "ss" distribution). Steady state distributions will normally be determined for systems which are not varying in time, but in some cases, ss distributions can be useful in modeling/simulating systems with time variation. For example, if the time course of applied charges and/or non-conservative fields is sufficiently slow compared to the relaxation time(s) of the media making up the electrophysiological system, a series (i.e., a time series) of non-time varying, steady state charge distributions may be sufficient to model/simulate the overall time variation of the system.

From Eqs. (18), (19), and (29), and assuming that at steady state, the $q_k^s$'s and the individual $V_A^f$'s, $V_B^f$'s, and $V_{int}^f$'s do not vary with time (or, as discussed above, vary sufficiently slowly so that they can be treated as constant for the purposes of the calculation), the steady state distribution for $\sigma_B \neq 0$ and $\sigma_{int} \neq 0$ is given by:

$$q_A^{f(ss)} = -(\sigma_{diff}/\sigma_{sum})(1/2\pi)[\Sigma_{i \neq A} q_i^{f(ss)} \Omega_{a \leftarrow i} + \underline{\Sigma_{k \neq A,B,int} q_k^{s(ss)} \Omega_{a \leftarrow k}}] + (2\varepsilon_0/\sigma_{sum}) V_A^{f(ss)}, \quad (33)$$

$$q_B^{f(ss)} = +(\varepsilon_0/\sigma_B) V_B^{f(ss)}, \text{ and} \quad (34)$$

$$q_{int}^{f(ss)} = +(\varepsilon_0/\sigma_{int}) V_{int}^{f(ss)}, \quad (35)$$

where, as in Eq. (18), the first summation in Eq. (33) includes all quantities of redistributable free interface charge in B-type cells, as well as all quantities of redistributable free interior charges in int calculation cells. In Eq. (33), we have made explicit that the second summation (the k summation) does not include int calculation cells since we are assuming that $\sigma_{int} > 0$. We have also used underlining to indicate that under the assumptions applicable to this equation, the second summation excludes all B-type and all int-type cells and not just the particular B cell and the particular int cell of Eqs. (34) and (35). The second summation has been retained because, as noted above, s charges do not require formal calculation cells, e.g., the point source of Examples 3-5 was not located in a formal calculation cell. By retaining the second summation, the effects of s charges which do not reside in formal calculation cells are included in the modeling/simulation.

Adding Eqs. (33) and (34), we have for the steady state, total quantity of free charge at the interface:

$$q_{tot}^{f(ss)} = -(\sigma_{diff}/\sigma_{sum})(1/2\pi)\left[\sum_{i \neq A} q_i^{f(ss)} \Omega_{a \leftarrow i} + \sum_{k \neq A,B,int} q_k^{s(ss)} \right.$$
$$\left. \Omega_{a \leftarrow k}\right] + (2\varepsilon_0/\sigma_{sum}) V_A^{f(ss)} + (\varepsilon_0/\sigma_B) V_B^{f(ss)}, \quad (36)$$

which upon removing $q_B^{f(ss)}$ from the first summation and using Eqs. (13) and (34) gives:

$$q_{tot}^{f(ss)} = -(\sigma_{diff}/\sigma_{sum})(1/2\pi)\left[\sum_{i \neq A,B} q_i^{f(ss)} \Omega_{a \leftarrow i} + \sum_{k \neq A,B,\underline{int}} q_k^{s(ss)} \right.$$
$$\left. \Omega_{a \leftarrow k}\right] + (2\varepsilon_0/\sigma_{sum})\left[V_A^{f(ss)} + V_B^{f(ss)}\right]. \quad (37)$$

Alternatively, Eq. (37) can be derived directly from Eq. (23). For $\sigma_B=0$, Eq. (37) becomes:

$$q_{tot(\sigma_B=0)}^{f(ss)} = q_{A(\sigma_B=0)}^{f(ss)} \quad (38)$$
$$= -(1/2\pi)\left[\sum_{i \neq A,B} q_{i(\sigma_B=0)}^{f(ss)} \Omega_{a \leftarrow i} + \sum_{k \neq A,\underline{int}} q_k^{s(ss)} \Omega_{a \leftarrow k}\right] +$$
$$(2\varepsilon_0/\sigma_A) V_A^{f(ss)},$$

where cell B has been reintroduced to the second summation (the k summation) since cell B can contain s charge when $\sigma_B=0$.

Returning to Eq. (33) and recalling, as noted above, that the first summation (the i summation) in that equation includes all quantities of redistributable free interface charge in B-type calculation cells and all quantities of redistributable free interior charges in int-type calculation cells, we can rewrite the equation to read:

$$q^f_A{}^{(ss)} = -(\sigma_{diff}/\sigma_{sum})(1/2\pi)\Sigma_{i=\underline{A,B,int}} q^{f(ss)}_i \Omega_{a \leftarrow i} + g^f_A{}^{(ss)}, \quad (39)$$

where, as in Eq. (33), the underlined subscripts B and int represent, respectively, all B-type cells and all int-type cells, and where $g^f_A{}^{(ss)}$ is a source-type constant which is given by:

$$g^f_A{}^{(ss)} = -(\sigma_{diff}/\sigma_{sum})(1/2\pi)[\Sigma_{i=\underline{B,int}} q^{f(ss)}_i \Omega_{a \leftarrow i} + \Sigma_{k=\underline{A,B,int}} q^s_k{}^{(ss)} \Omega_{a \leftarrow k}] + (2\epsilon_0/\sigma_{sum}) V^f_A{}^{(ss)}. \quad (40)$$

Note that the first summation in Eq. (40), as well as that in Eq. (44) below, is a source type term since, as can be seen from Eq. (34), at steady state, all of the $q^{f(ss)}_i$'s for the B-type cells covered by the summation depend on their $\sigma_B$ and $V_B^{(ss)}$ values which, by assumption, are constant and thus as seen from the A-type cells, these B-type cells act like constant sources. Also, again by assumption, the redistributable free interior charges of the int cells are constant because $\sigma_{int}$ and $V_{int}^{(ss)}$ are constant in Eq. (35), and thus these int-type cells also act like constant sources as seen from A-type cells.

An examination of Eqs. (39) and (40) reveals that they represent a set of simultaneous equations for the $q^{f(ss)}_i$'s at the higher conductivity sides (A sides) of each conductivity interface in the system which, in matrix notation, can be written:

$$Mq^{f(ss)} = g^{f(ss)}, \quad (41)$$

where:

$$m_{KK} = 1, \quad (42)$$

$$m_{KL} = (\sigma_{diff}/\sigma_{sum})(1/2\pi)\Omega_{K \leftarrow L}, \text{ and} \quad (43)$$

$$g^f_K{}^{(ss)} = -(\sigma_{diff}/\sigma_{sum})(1/2\pi)[\Sigma_{i=\underline{B,int}} q^{f(ss)}_i \Omega_{K \leftarrow i} + \Sigma_{k=K,\underline{B,int}} q^s_k{}^{(ss)} \Omega_{K \leftarrow k}] + (2\epsilon_0/\sigma_{sum}) V^f_K{}^{(ss)}, \quad (44)$$

where $\Omega_{K \leftarrow L}$ is the solid angle of the a face of the $K^{th}$ calculation cell as seen from the quantity of free charge of the $L^{th}$ calculation cell, $\Omega_{K \leftarrow i}$ is the solid angle of the a face of the $K^{th}$ calculation cell as seen from the quantity of redistributable free interface charge of the $i^{th}$ B-type cell or the $i^{th}$ quantity of redistributable free interior charge, $\Omega_{K \leftarrow k}$ is the solid angle of the a face of the $K^{th}$ calculation cell as seen from the $k^{th}$ quantity of non-redistributable s charge, and $\sigma_{diff}$, $\sigma_{sum}$, and $V_K^{(ss)}$ are for the $K^{th}$ calculation cell, specifically, the $K^{th}$ higher conductivity A cell and its directly associated lower conductivity B cell.

These equations are solved using computer-implemented techniques such as the Jacobi, Gauss-Seidel, and successive over relaxation (SOR) iterative techniques, other iterative techniques, non-iterative techniques, or combinations thereof. See, for example, Varga, Richard S., *Matrix Iterative Analysis*, Englewood Cliffs, N.J., Prentice-Hall, Inc., 1962. Also, programs such as MATLAB (The MathWorks, Inc., Natick, Mass.) and the free software package GNU Octave (www.gnu.org/software/octave/), contain procedures that can be used if desired. It should be noted that using Eqs. (27), (28), and (30), steady state solutions can also be obtained by moving forward in time until steady state conditions are achieved.

III. BOUND CHARGES FOR NON-CONDUCTIVE DIELECTRICS

Turning now to embodiments of the third improvement, we consider first a set of m isotropic, linear, homogeneous, dielectric materials, each material having a relative dielectric constant $\epsilon^m_r$, i.e., each material's permittivity $\epsilon^m$ equals $\epsilon^m_r \epsilon_0$ and its susceptibility $\chi^m$ equals $(\epsilon^m - \epsilon_0)/\epsilon_0$ or, in terms of $\epsilon^m_r$, $\chi^m = \epsilon^m_r - 1$. For this initial analysis of the dielectric case, we will assume that all of the materials are non-conductive. Unlike the conductive case where free charges may pass through interfaces between materials having different conductivities, bound charges, as their name implies, are bound to the material in which they are induced. In particular, for the materials being considered, bound charges (also known as polarization charges) are found within the material at its interfaces with other materials, as well as at the locations of quantities of free charge within the material, with the sum of all of the quantities of bound charge in the material being zero.

As above, for ease of presentation, in certain embodiments, we will treat the case of a cubic calculation cell, the same analysis being applicable to calculation cells having other configurations. Also, the first and second improvements, as developed above in connection with free charges, will be used in the analysis, it being understood that the third improvement can be used separately or with only one of the first and second improvements. We begin with a discussion of bound interface charge and then turn to bound interior charge.

A. Bound Interface Charge

We will assume that the calculation cell of interest is cell A of FIG. 1 and that this calculation cell is located at an interface between the dielectric medium and another medium, the interface being at face ab. In accordance with an embodiment of the disclosure, the quantity of bound interface charge induced at face ab of cell A is taken as zero while for all of the other faces of the calculation cell, i.e., face a and faces c through f in FIG. 1, the quantity of bound charge induced at the face is given by:

$$q^{b-m}_j = -(\chi^m/4\pi)(\Sigma_i q_i \Omega_{j \leftarrow i}), \quad (45)$$

where the superscript b-m indicates bound interface charge of the $m^{th}$ material, the index j indicates a face of the calculation cell other than the interface face ab, the index i covers all of the charges in the system and, as above, $\Omega_{j \leftarrow i}$ is the solid angle of the $j^{th}$ face as seen from the $i^{th}$ quantity of charge, the solid angle being positive when the $i^{th}$ quantity of charge sees the inward side of the $j^{th}$ face and negative when it sees the outward side, where inward and outward are with respect to the internal volume of the calculation cell.

In Eq. (45), the notation $q_i$ without a superscript is used to indicate both free and bound charges of all types anywhere in the system, e.g., in calculation cells belonging or not belonging to the $m^{th}$ material. The quantities of free and bound charge represented by $q_i$ thus include quantities of free and bound charge at interfaces, as well as quantities within the materials making up the system (i.e., the quantities of free and bound interior charges). For this initial dielectric case where all materials are assumed to be non-conductive, the quantities of free charge included in $q_i$ of Eq. (45) are only quantities of non-redistributable free charge ($q^s_i$ charges), i.e., the free charge components of $q_i$ are imposed charges which, after introduction, remain in place there being no conductivity by which they can redistribute. In the conductive case discussed in Section IV below, $q_i$ is extended to include quantities of redistributable free charge (interface and interior).

It should be noted that in order to induce bound charge, there needs to be at least some free charge in the system. For example, in the exemplary embodiment of Example 4 below, the applied free charge is a quantity of free charge in the form of an applied point source located in a non-polarizable, non-conductor, i.e., air in Example 4. In that example, the point source is located above a non-conductive, dielectric cube which allows the solution in accordance with the present disclosure for that example to be compared with the analytic solution for the similar configuration of a point source above a dielectric of semi-infinite extent. See Klee, M. M., "Biology's built-in Faraday cages," *Am. J. Phys.*, vol. 82, no. 6, pp. 451-459, May 2014, and, in particular, Equation (28) of that article evaluated at t=0. This article will be referred to herein as "Klee 2014" and is incorporated herein in its entirety by reference.

In addition to point source stimulation, uniform field stimulation may be of interest in some cases. Applied quantities of free charge can be used to model a uniform field by, for example, employing the geometry of a parallel plate capacitor and applying a uniform distribution of charge to each plate (positive charge on one plate and negative on the other). Such an arrangement produces a substantially uniform electric field between the plates at locations distant from the edges of the plates. Separated uniform distributions of applied free charge can also be used to model the applied free charge distribution produced by a non-conservative field. As an alternative to quantities of applied free charge, for some simulations, it may be convenient to employ an applied electric field to represent the applied source(s) imposed on an electrophysiological system. In this case, instead of using solid angles of the faces of calculation cells as seen from the applied free charges, fluxes of the applied electric field at the faces are used, i.e., integrals of the normal component of the applied electric field at the faces are used.

Example 6 below illustrates this approach for the case of dipole sources.

The foregoing considerations regarding the need for at least some free charge in the system being modeled/simulated are not limited to dielectric systems but also apply to conductive systems and conductive/dielectric systems. For purposes of this initial analysis of the dielectric case, we will assume that both the quantities of free charge (if any) within the dielectric material of interest and the quantities of free charge (if any) outside of the dielectric material of interest are fixed in both time and space, this assumption being removed when we turn to the conductive dielectric case.

Returning to Eq. (45), from this equation, the total quantity of bound interface charge induced in interface calculation cell A due to induced charges at face a and faces c through f can be written:

$$q^{b-m}_A = \Sigma_{j=a,c,d,e,f} q^{b-m}_j = -(\chi^m/4\pi)(\Sigma_{j=a,c,d,e,f} \Sigma_i q_i \Omega_{j \leftarrow i}). \quad (46)$$

This expression can be simplified by (1) separating the quantities of charge within interface calculation cell A (both bound ($q^{b-m}_A$) and free ($q^{s-m}_A$)) from those outside of that cell and (2) recalling (see discussion following Eq. (6) above) that for a quantity of charge outside a calculation cell, the sum of the solid angles for all of the faces of the cell (i.e., including interface face ab) is zero:

$$q^{b-m}_A = -(\chi^m/4\pi)\left(\sum_{j=a,c,d,e,f} q^{b-m}_A \Omega_{j \leftarrow A} + \sum_{j=a,c,d,e,f} q^{s-m}_A \Omega_{j \leftarrow A} + \sum_{j=a,c,d,e,f} \sum_{i \neq A} q_i \Omega_{j \leftarrow i}\right) \quad (47)$$

$$= -(\chi^m/4\pi)\left(\sum_{j=a,c,d,e,f} q^{b-m}_A \Omega_{j \leftarrow A} + \sum_{j=a,c,d,e,f} q^{s-m}_A \Omega_{j \leftarrow A} - \right.$$

$$\left. \sum_{i \neq A} q_i \Omega_{ab \leftarrow i}\right).$$

For $q^{b-m}_A$ and $q^{s-m}_A$ (if any) located at the center of cell A, $\Omega_{j \leftarrow A}$ is $+4\pi/6$ for each face of cell A so that Eq. (47) becomes:

$$q^{b-m}_A = -(\chi^m/4\pi)(q^{b-m}_A(20\pi/6) + q^{s-m}_A(20\pi/6) - \Sigma_{i \neq A} q_i \Omega_{ab \leftarrow i}). \quad (48)$$

Using the second improvement of this disclosure, i.e., the flattened calculation cell process, the expression for $q^{b-m}_A$ becomes even simpler since in that case, Eq. (47) becomes:

$$q^{b-m}_A = -(\chi^m/4\pi)(q^{b-m}_A \Omega_{a \leftarrow A} + q^{s-m}_A \Omega_{a \leftarrow A} - \Sigma_{i \neq A} q_i \Omega_{ab \leftarrow i}), \quad (49)$$

which by using Eqs. (10) and (12) for $\Omega_{ab \leftarrow i}$ and $\Omega_{a \leftarrow A}$, respectively, becomes:

$$q^{b-m}_A = -(\chi^m/4\pi)(2\pi q^{b-m}_A + 2\pi q^{s-m}_A + \Sigma_{i \neq A} q_i \Omega_{a \leftarrow i}), \quad (50)$$

which upon rearrangement gives:

$$q^{b-m}_A = -[\chi^m/(\chi^m+2)][q^{s-m}_A + (1/2\pi)\Sigma_{i \neq A} q_i \Omega_{a \leftarrow i}], \quad (51)$$

or in terms of $\varepsilon^m_r$:

$$q^{b-m}_A = -[(\varepsilon^m_r - 1)/(\varepsilon^m_r + 1)][q^{s-m}_A + (1/2\pi)\Sigma_{i \neq A} q_i \Omega_{a \leftarrow i}]. \quad (52)$$

Eq. (52) constitutes a set of simultaneous equations for the $q^{b-m}_i$'s of the material having the dielectric constant $\varepsilon^m_r$ as can be seen most clearly by rewriting Eq. (52) so as to separate the quantities of bound interface charge of the $m^{th}$ material from all of the other charges in the system:

$$q^{b-m}_A = -[(\varepsilon^m_r - 1)/(\varepsilon^m_r + 1)][(1/2\pi)\Sigma_{i \neq A} q^{b-m}_i \Omega_{a \leftarrow i}] + g^m_A, \quad (53)$$

where $g^m_A$ is given by:

$$g^m_A = -[(\varepsilon^m_r - 1)/(\varepsilon^m_r + 1)][q^{s-m}_A + (1/2\pi)\Sigma_{i \neq A} q^*_i \Omega_{a \leftarrow i}], \quad (54)$$

where $q^*_i$ in Eq. (54) includes quantities of s charge of interface calculation cells of the $m^{th}$ material other than cell A, quantities of s charge and associated bound charge (see Eq. (67) below) for interior calculation cells of the $m^{th}$ material, and quantities of bound and s charge (interface or interior) of materials other than the $m^{th}$ material. For interior calculation cells, $q^*_i$ can also be formulated in terms of the reduced, non-redistributable, free interior charge of Eq. (69) below.

In matrix notation, these equations can be written:

$$Bq^{b-m} = g^m, \quad (55)$$

where:

$$b_{KK} = 1, \quad (56)$$

$$b_{KL} = (\varepsilon^m_r - 1)/(\varepsilon^m_r + 1)(1/2\pi)\Omega_{K \leftarrow L}, \text{ and} \quad (57)$$

$$g^m_K = -[(\varepsilon^m_r - 1)/(\varepsilon^m_r + 1)][q^{s-m}_K + (1/2\pi)\Sigma_{i \neq K} q^*_i \Omega_{K \leftarrow i}], \quad (58)$$

where $\Omega_{K \leftarrow L}$ is the solid angle of the a face of the $K^{th}$ calculation cell of the $m^{th}$ material as seen from the quantity of bound charge of the $L^{th}$ calculation cell of the $m^{th}$ material, $q^{s-m}_K$ is the quantity of s-type free charge in the $K^{th}$ calculation cell, $\Omega_{K \leftarrow i}$ is the solid angle of the a face of the $K^{th}$ calculation cell as seen from the $i^{th}$ quantity of $q^*$ charge as defined above. Because of the need for at least some free charge in the system (see above), in Eqs. (55)-(58), at least one of the $q^{s-m}_K$'s or at least one s-type charge of $q^*$ is different from zero or the system includes at least one applied source whose effects are modeled through an applied electric field. As with Eqs. (41)-(44), Eqs. (55)-(58) are solved using computer-implemented techniques of the types discussed above.

In cases where there is more than one dielectric material (all materials still assumed to be non-conductive), the quantities of bound charge for the entire set of materials can be calculated using a process in which, for example, Eqs. (55)-(58) are solved seriatim for each material in the set with the quantities of bound charge in the other materials of the set being held constant, the process being iterated until a consistent set of quantities of bound charge for all of the materials is found. Alternatively, the equations for the individual materials can be assembled into a single matrix having, for example, the following form and solved simultaneously:

$$Bq^b = g, \quad (59)$$

where:

$$b_{KK} = 1, \quad (60)$$

$$b_{KL} = (\varepsilon_r^K - 1)/(\varepsilon_r^K + 1)(1/2\pi)\Omega_{K \leftarrow L}, \text{ and} \quad (61)$$

$$g_K = -[(\varepsilon_r^K - 1)/(\varepsilon_r^K + 1)][q^s_K + (1/2\pi)\Sigma_{i \neq K} q^*_i \Omega_{K \leftarrow i}], \quad (62)$$

where the matrix B includes all of the calculation cells of the system which contain quantities of bound interface charge, $\Omega_{K \leftarrow L}$ is the solid angle of the a face of the $K^{th}$ such calculation cell as seen from the quantity of bound interface charge of the $L^{th}$ calculation cell wherever located (i.e., not limited to the bound interface charges of a particular dielectric material), $q^s_K$ is the quantity of s free charge in the $K^{th}$ calculation cell, $\Omega_{K \leftarrow i}$ is the solid angle of the a face of the $K^{th}$ calculation cell as seen from the $i^{th}$ quantity of q* charge where q* charge includes quantities of s charge of interface calculation cells other than the $K^{th}$ calculation cell and quantities of s charge and associated bound charge (see Eq. (67) below) for interior calculation cells, and $\varepsilon_r^K$ is the relative dielectric constant of the $K^{th}$ calculation cell. In this case, two calculation cells (two K values) are used at each location of each interface of the system where two materials having relative dielectric constants >1 meet. For quantities of charge external to the two calculation cells, the solid angle magnitudes for these two calculation cells are the same, but their signs are opposite. For the interaction of a quantity of charge in one of the K cells with the other K cell, by analogy with Eqs. (12) and (13), the solid angle in each case is $+2\pi$. As with Eqs. (41)-(44) and Eqs. (55)-(58), Eqs. (59)-(62) are solved using computer-implemented techniques of the types discussed above.

B. Bound Interior Charge

For isotropic dielectrics, quantities of bound interior charges occur only at the locations of free interior charges (either redistributable or non-redistributable) and are directly proportional to the quantities of free interior charge. Specifically, for interior bound charge, instead of Eq. (46), we have:

$$q^b_{int} = -(\chi/4\pi)(\Sigma_j \Sigma_i q_i \Omega_{j \leftarrow i}), \quad (63)$$

where $\chi$ is the susceptibility at the location of the int calculation cell, the j summation includes all of the faces of the calculation cell, there being no excluded interface face as in Eq. (46), and the i summation covers all of the charges in the system. Using the fact that the solid angle for a quantity of charge outside/inside a closed surface is zero/$+4\pi$, we have:

$$q^b_{int} = -(\chi)(q^b_{int} + q^s_{int}), \quad (64)$$

where $q^s_{int}$ is the non-redistributable free interior charge in cell int. For conductive dielectrics discussed in the next section, $q^s_{int}$ in Eq. (64) becomes $q^f_{int}$ for int calculation cells that are conductive. Rearranging Eq. (64), we have:

$$q^b_{int} = -(\chi)/(1+\chi)q^s_{int}, \quad (65)$$

or when the int cell is conductive:

$$q^b_{int} = -(\chi)/(1+\chi)q^f_{int}. \quad (66)$$

In terms of $\varepsilon_r$, these equations can be written:

$$q^b_{int} = -(\varepsilon_r - 1)/(\varepsilon_r)q^s_{int}, \text{ and} \quad (67)$$

$$q^b_{int} = -(\varepsilon_r - 1)/(\varepsilon_r)q^f_{int}. \quad (68)$$

The induced bound interior charge at the locations of free interior charges can also be considered as reducing the magnitude of the free charges. Designating those reduced-magnitude charges as r charges, we have:

$$q^{s-r}_{int} = (1/\varepsilon_r)q^s_{int}, \text{ and} \quad (69)$$

$$q^{f-r}_{int} = (1/\varepsilon_r)q^f_{int}, \quad (70)$$

for non-conductive and conductive int calculation cells, respectively.

IV. BOUND CHARGE/FREE CHARGE PROCESS

In Section III, the dielectric material was assumed to be non-conductive. In accordance with embodiments of the disclosure, conductivity is introduced by alternately calculating free charge and bound charge distributions, with the free charge distribution being treated as fixed in time and space when the bound charge distribution is being calculated and vice versa. In particular, when calculating bound charges, free charges are treated as fixed source charges and when calculating free charges, bound charges are treated as fixed source charges. In this way, the equations developed in Section III for a non-conductive dielectric and the equations developed in Sections I and II for a non-dielectric conductor become directly applicable to a conductive dielectric.

Compared to redistributions of free charge, redistributions of bound charge are treated as occurring instantaneously. In particular, because electrophysiological systems are primarily composed of water molecules, they are able to keep pace with changing electric fields having frequencies as high as a gigahertz. Indeed, water's $\varepsilon_r$ of 80 only drops below 10 when the frequency rises above 100 GHz. Endogenous electrophysiological activity, on the other hand, occurs at frequencies far below the gigahertz range. For example, rise times for action potentials propagating along axons are on the order of 1 msec, corresponding to frequencies in the kilohertz range, while the kinetics of the underlying opening and closing of ion channels in an axon's membrane typically have time constants longer than ~20 μsec, corresponding to frequencies below a megahertz. Higher frequencies, extending, in some cases, into the gigahertz range, are used in some experimental studies performed on biological tissues, but except for such studies, the effects of frequency, as well as temperature and other variables, on water's dielectric constant are generally not significant, and thus the water component of biological systems can be treated as having a constant relative dielectric constant of 80.

To simplify the notation, we will derive the equations that describe the time course of the quantities of free and bound charge on the assumption that the electrophysiological system of interest is being modeled using the solid angle and flattened calculation cell processes, i.e., the equations will be derived assuming the first and second improvements are being used. Based on this derivation and the remainder of this disclosure, a skilled person will be able to derive the corresponding equations when either of the first and second improvements or both of those improvements are not employed.

Eqs. (55)-(58) or Eqs. (59)-(62) can be used as the starting point for the derivation of the equations for the conductive case, with Eqs. (59)-(62) providing a somewhat simpler notation and thus will be used. Rewriting those equations to introduce $t_n$ and $t_{n+1}$ notation, where n is the time step, we have:

$$Bq^b(t_{n+1}) = g(t_n), \quad (71)$$

where:

$$b_{KK} = 1, \quad (72)$$

$$b_{KL} = (\varepsilon_r^K - 1)/(\varepsilon_r^K + 1)(1/2\pi)\Omega_{K \leftarrow L}, \text{ and} \quad (73)$$

$$g_K(t_n) = -[(\varepsilon_r^K - 1)/(\varepsilon_r^K + 1)][q^s_K(t_n) + q^f_K(t_n) + (1/2\pi)\Sigma_{i \neq K}(q^s_i(t_n) + q^f_i(t_n))\Omega_{K \leftarrow i}], \quad (74)$$

where the notations $q^s_K(t_n)$ and $q^s_i(t_n)$ refer to quantities of non-distributable free charge and $q^f_K(t_n)$ and $q^f_i(t_n)$ refer to quantities of redistributable free charge in the $K^{th}$ and $i^{th}$ calculation cells, respectively, at time $t_n$. As noted above, at any given time, a given calculation cell can only have one of s and f charges depending on whether the cell's conductivity is zero or greater than zero. Thus, either $q^s_K(t_n)$ or $q^f_K(t_n)$ is zero and likewise for $q^s_i(t_n)$ or $q^f_i(t_n)$. However, to provide a generally applicable equation, both possibilities are included in Eq. (74), it being understood that, in use, only the appropriate possibility is employed for each calculation cell. If any of the $q^s_i(t_n)$'s or $q^f_i(t_n)$'s of Eq. (74) are for int calculation cells, then the reduced value of Eq. (69) or the reduced value of Eq. (70), respectively, is used in Eq. (74) so that Eqs. (71)-(74) take account of the bound interior charge (at $t_{n+1}$) associated with those free charges (at $t_n$) when calculating the bound interface charges (at $t_{n+1}$).

For purposes of calculating free charges at $t_{n+1}$ (see below), from Eqs. (67) and (68), the bound charges at $t_{n+1}$ in int calculation cells resulting from free charges in those cells at $t_n$ are:

$$q^b_{int}(t_{n+1}) = -(\varepsilon_r - 1)/(\varepsilon_r)q^s_{int}(t_n), \text{ or} \quad (75)$$

$$q^b_{int}(t_{n+1}) = -(\varepsilon_r - 1)/(\varepsilon_r)q^f_{int}(t_n), \quad (76)$$

depending on whether the int cell is non-conductive or conductive.

As above, Eqs. (71)-(74) can be solved using computer-implemented techniques of the type discussed above. The solution gives the quantities of bound interface charge of the system at time $t_{n+1}$. These quantities of bound interface charge along with the quantities of bound interior charge given by Eqs. (75) and (76) are then used to calculate the system's quantities of free charge at time $t_{n+1}$. Beginning with the redistributable free interface charge, for the case where calculation cells A and B are both conductive, Eqs. (27) and (28), with the effects of quantities of bound charge included, become:

$$q^f_A(t_{n+1}) = (1 - \Delta t \sigma_{sum}/2\varepsilon_0)q^f_A(t_n) - (\Delta t \sigma_{sum}/2\varepsilon_0)q^b_A(t_{n+1}) \quad (77)$$
$$-\Delta t \sigma_{diff}/4\pi\varepsilon_0 \sum_{i \neq A}(q^f_i(t_n) + q^b_i(t_{n+1}))\Omega_{a \leftarrow i}$$
$$-\Delta t \left[\sigma_{diff}/4\pi\varepsilon_0 \sum_{i \neq A,B}(q^s_k(t_n) + q^b_k(t_{n+1}))\Omega_{a \leftarrow k} - I^f_A(t_n)\right], \text{ and}$$

-continued $$q^f_B(t_{n+1}) = (1 - \Delta t \sigma_B/\varepsilon_0)q^f_B(t_n) - (\Delta t \sigma_B/\varepsilon_0)q^b_B(t_{n+1}) + I^f_B(t_n)\Delta t, \quad (78)$$

where, as in Eqs. (3) and (4), the i and k summations are over different calculation cells, i.e., conductive and non-conductive cells, respectively. For the case where $\sigma_B = 0$, we have from Eq. (32) with the effects of quantities of bound charge included:

$$q^f_{A(\sigma_B=0)}(t_{n+1}) = (1 - \Delta t \sigma_A/2\varepsilon_0)q^f_{A(\sigma_B=0)}(t_n) - (\Delta t \sigma_A/2\varepsilon_0) \quad (79)$$
$$q^b_{A(\sigma_B=0)}(t_{n+1})$$
$$-\Delta t \sigma_A/4\pi\varepsilon_0 \sum_{i \neq A,B}(q^f_{i(\sigma_B=0)}(t_n) + q^b_{i(\sigma_B=0)}(t_{n+1}))$$
$$\Omega_{a \leftarrow i} - \Delta t \left[\sigma_A/4\pi\varepsilon_0 \sum_{k \neq A}(q^s_k(t_n) + q^b_{k(\sigma_B=0)}(t_{n+1}))\Omega_{a \leftarrow k} - I^f_A(t_n)\right],$$

where again the i and k summations are over different calculation cells. In this case, the k summation includes the B cell associated with the A cell for which the calculation is being performed, i.e., the k summation picks up any quantities of s or bound charge in the associated B cell.

As discussed above in connection with Eq. (18), the i and k summations of Eqs. (77) and (79) include quantities of redistributable and non-redistributable free charge (f and s charges) in int calculation cells. For those calculation cells, the bound charges ($q^b_i$ and $q^b_k$) used in the i and j summations are those given by Eqs. (76) or (75), respectively.

For systems that include redistributable free charges in int calculation cells, from Eq. (30) with the effects of bound charge in the calculation cell included, we have:

$$q^f_{int}(t_{n+1}) = (1 - \Delta t \sigma_{int}/\varepsilon_0)q^f_{int}(t_n) - (\Delta t \sigma_{int}/\varepsilon_0)q^b_{int}(t_{n+1}) + I^f_{int}(t_n)\Delta t, \quad (80)$$

where $q^b_{int}(t_{n+1})$ is given by Eq. (76).

Eqs. (77)-(78) or Eq. (79) and Eq. (80) are evaluated at all of the conductive calculation cells of the system thus giving a full set of quantities of free charge at $t_{n+1}$ which along with the quantities of bound charge calculated using Eqs. (71)-(76) give all of the quantities of charge at $t_{n+1}$ thus completing a time step. The process, i.e., Eqs. (71)-(76) followed by Eqs. (77)-(78) or Eq. (79) and Eq. (80), is then repeated with the just-calculated $t_{n+1}$ values becoming the starting values for the next time step. For example, for $t_{n+2}$, Eqs. (71)-(74) become:

$$Bq^b(t_{n+2}) = g(t_{n+1}), \quad (81)$$

where:

$$b_{KK} = 1, \quad (82)$$

$$b_{KL} = (\varepsilon_r^K - 1)/(\varepsilon_r^K + 1)(1/2\pi)\Omega_{K \leftarrow L}, \text{ and} \quad (83)$$

$$g_K(t_{n+1}) = -[(\varepsilon_r^K - 1)/(\varepsilon_r^K + 1)][q^s_K(t_{n+1}) + q^f_K(t_{n+1}) + q^f_K(t_{n+1}) + (1/2\pi)\Sigma_{i \neq K}(q^s_i(t_{n+1}) + q^f_i(t_{n+1}))\Omega_{K \leftarrow i}], \quad (84)$$

Eqs. (75)-(76) become:

$$q^b_{int}(t_{n+2}) = -(\varepsilon_r - 1)/(\varepsilon_r)q^s_{int}(t_{n+1}), \text{ and} \quad (85)$$

$$q^b_{int}(t_{n+2}) = -(\varepsilon_r - 1)/(\varepsilon_r)q^f_{int}(t_{n+1}), \quad (86)$$

Eqs. (77)-(78) become:

$$q_A^f(t_{n+2}) = (1 - \Delta t \sigma_{sum}/2\varepsilon_0)q_A^f(t_{n+1}) - (\Delta t \sigma_{sum}/2\varepsilon_0)q_A^b(t_{n+2}) \quad (87)$$
$$- \Delta t \sigma_{diff}/4\pi\varepsilon_0 \sum_{i \neq A}(q_i^f(t_{n+1}) + q_i^b(t_{n+2}))\Omega_{a \leftarrow i}$$
$$- \Delta t \left[ \sigma_{diff}/4\pi\varepsilon_0 \sum_{i \neq A,B}(q_k^s(t_{n+1}) + q_k^b(t_{n+2}))\Omega_{a \leftarrow k} - I_A^f(t_{n+1}) \right], \text{ and}$$

$$q_B^f(t_{n+2}) = (1 - \Delta t \sigma_B/\varepsilon_0)q_B^f(t_{n+1}) - (\Delta t \sigma_B/\varepsilon_0)q_B^b(t_{n+2}) + I_B^f(t_{n+1})\Delta t, \quad (88)$$

and Eq. (80) becomes:

$$q_{int}^f(t_{n+2}) = (1 - \Delta t \sigma_{int}/\varepsilon_0)q_{int}^f(t_{n+1}) - (\Delta t \sigma_{int}/\varepsilon_0)q_{int}^b(t_{n+2}) + I_{int}^f(t_{n+1})\Delta t. \quad (89)$$

As another example, for the first time step, Eqs. (71)-(74) become:

$$Bq^b(t_1) = g(t_0), \quad (90)$$

where:

$$b_{KK} = 1, \quad (91)$$

$$b_{KL} = (\varepsilon_r^K - 1)/(\varepsilon_r^K + 1)(1/2\pi)\Omega_{K \leftarrow L}, \text{ and} \quad (92)$$

$$g_K(t_0) = -[(\varepsilon_r^K - 1)/(\varepsilon_r^K + 1)][q_K^s(t_0) + q_K^f(t_0) + (1/2\pi)\Sigma_{i \neq K}(q_i^s(t_0) + q_i^f(t_0))\Omega_{K \leftarrow i}], \quad (93)$$

Eq. (75)-(76) become:

$$q_{int}^b(t_1) = -(\varepsilon_r - 1)/(\varepsilon_r)q_{int}^s(t_0), \text{ and} \quad (94)$$

$$q_{int}^b(t_1) = -(\varepsilon_r - 1)/(\varepsilon_r)q_{int}^f(t_0), \quad (95)$$

Eqs. (77)-(78) become:

$$q_A^f(t_1) = (1 - \Delta t \sigma_{sum}/2\varepsilon_0)q_A^f(t_0) - (\Delta t \sigma_{sum}/2\varepsilon_0)q_A^b(t_1) \quad (96)$$
$$- \Delta t \sigma_{diff}/4\pi\varepsilon_0 \sum_{i \neq A}(q_i^f(t_0) + q_i^b(t_1))\Omega_{a \leftarrow i}$$
$$- \Delta t \left[ \sigma_{diff}/4\pi\varepsilon_0 \sum_{i \neq A,B}(q_k^s(t_0) + q_k^b(t_1))\Omega_{a \leftarrow k} - I_A^f(t_0) \right], \text{ and}$$

$$q_B^f(t_1) = (1 - \Delta t \sigma_B/\varepsilon_0)q_B^f(t_0) - (\Delta t \sigma_B/\varepsilon_0)q_B^b(t_1) + I_B^f(t_0)\Delta t, \quad (97)$$

and Eq. (80) becomes:

$$q_{int}^f(t_1) = (1 - \Delta t \sigma_{int}/\varepsilon_0)q_{int}^f(t_0) - (\Delta t \sigma_{int}/\varepsilon_0)q_{int}^b(t_1) + I_{int}^f(t_0)\Delta t. \quad (98)$$

It should be noted that these equations include free charges at $t_0$ but not bound charges, since bound charges only exist once there are free charges, i.e., for this formulation of the time series, bound charges are first computed at $t_1$.

In practice, the quantities of bound and free charge need not be stored for all of the time steps, but rather just two sets of quantities of bound and free charge need be stored, i.e., one for the "prior" time step and one for the "present" time step being computed. Once the "present" time step calculations are completed, the "prior" time step values can be replaced by the newly-calculated values and the process repeated. Note that Eqs. (71)-(80) involve quantities of bound charge at $t_{n+1}$, but not at $t_n$, so that only one set of quantities of bound charge needs to be stored. However, in practice, it can be helpful to store the quantities of bound charge for the prior time step for use as the starting point for the calculation of the quantities of bound charge for the present time step when using an iterative technique to calculate quantities of bound charge such as a Jacobi iteration (see, for example, Example 5 below).

Time series can be maintained for values that may be of interest for the particular system being simulated, e.g., quantities of bound and/or free charge values at a particular location of interest. The number of time steps employed will depend on the goals and/or the results of the simulation. For example, in certain embodiments, the goal of the simulation may be to determine the time course of quantities of bound and/or free charge at one or more locations of interest, e.g., in the region of the mouth of a pore in a biological membrane, and the process can be terminated when the quantities of free and/or bound charge become asymptotic and/or when the change in the quantities of free charge and/or bound charge per time step drops below a predetermined value. A variety of criteria for terminating a simulation will be evident to skilled persons from the present disclosure.

It should be noted that for some simulations, flattened calculation cells can be used in combination with non-flattened calculation cells. For example, at the locations of source charges, e.g., charges due to $V_{int}$'s, three dimensional calculation cells, e.g., cubic calculation cells, can be used so that free charge decay at those locations is determined using the same calculation process, e.g., the solid angle process, as used at interfaces. Three dimensional calculation cells can also be useful in simulating an anisotropic medium since the conductivity values and/or the relative dielectric constants of the faces of the calculation cells can be selected to account for the anisotropicity of the medium. Also, when the system being simulated includes non-conservative fields acting at an interface, three dimensional calculation cells can be used on either side of the interface.

V. FLOW CHARTS

FIGS. 3-8 set forth representative flow charts that can be used in the practice of the present disclosure. These flow charts are, of course, merely provided for purposes of illustrating embodiments of the disclosure and are not intended to limit the scope of the invention as defined by the claims in any manner.

Figure 3:
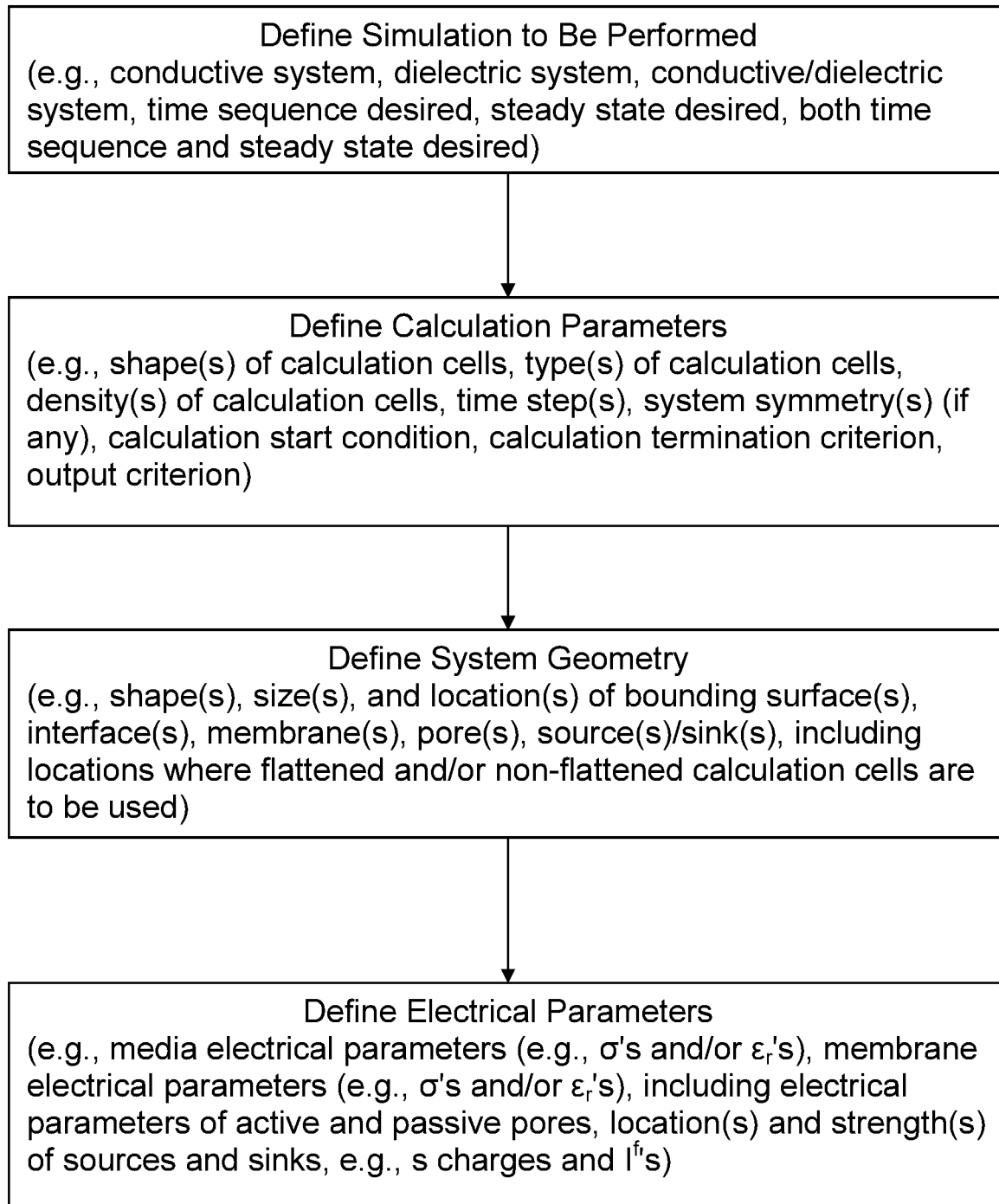
FIG. 3 is a representative flow chart for setting up a simulation in accordance with an embodiment of the disclosure.

FIG. 3 sets forth a flow chart that can be used for the initial steps (the setup steps) of a simulation. It includes defining the simulation to be performed, defining the calculation parameters, defining the system geometry, and defining the system's electrical parameters. Parameters other than those used in FIG. 3 can be used to define the simulation and the order in which the parameters are defined need not be that shown in FIG. 3.

Figure 4:
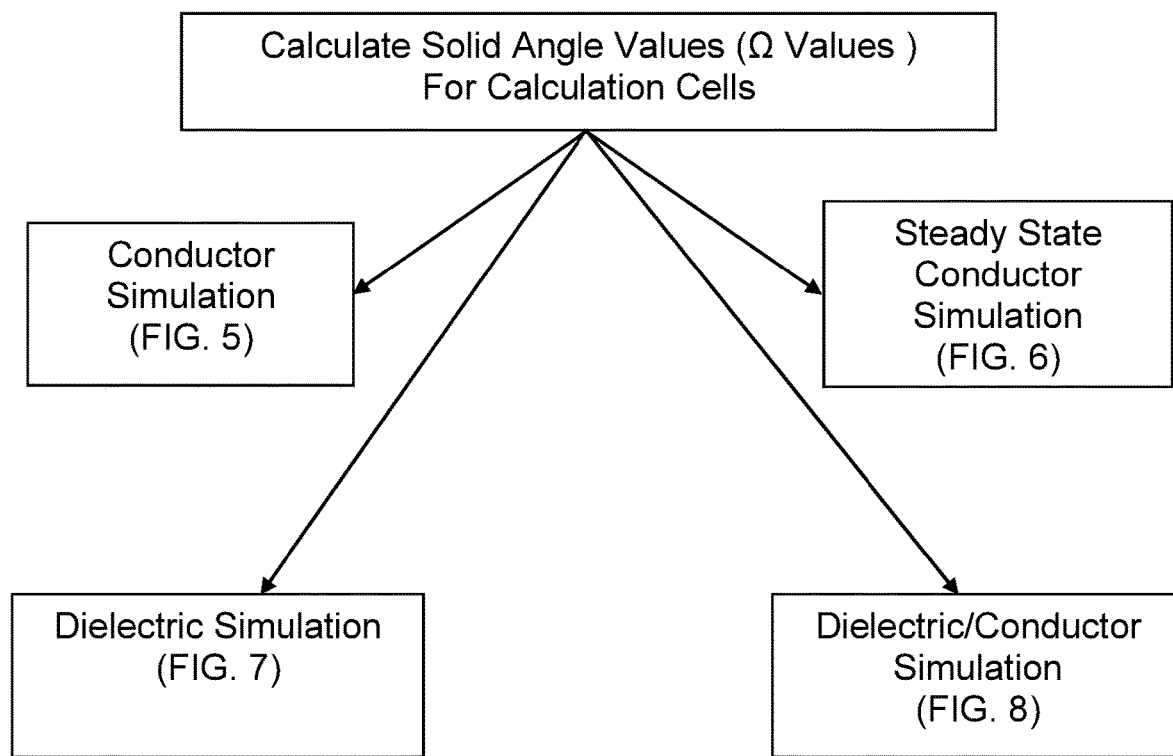
FIG. 4 is a representative flow chart in accordance with an embodiment of the disclosure in which solid angle values are calculated for subsequent use in the representative simulations of FIGS. 5-8.

FIG. 4 starts with the calculation of solid angle values using the system geometry defined in FIG. 3. These values establish the electrical coupling between the calculation cells and sources to be used in the simulation. In many cases, it will be convenient to calculate the solid angles in a stand alone program and store the results in a file that is read by a main program at the time simulations are performed. For example, if the effects of varying an electrical parameter are of interest, having the solid angles in a file can save run time as a series of simulations with different values for the parameter are performed.

Figure 6:
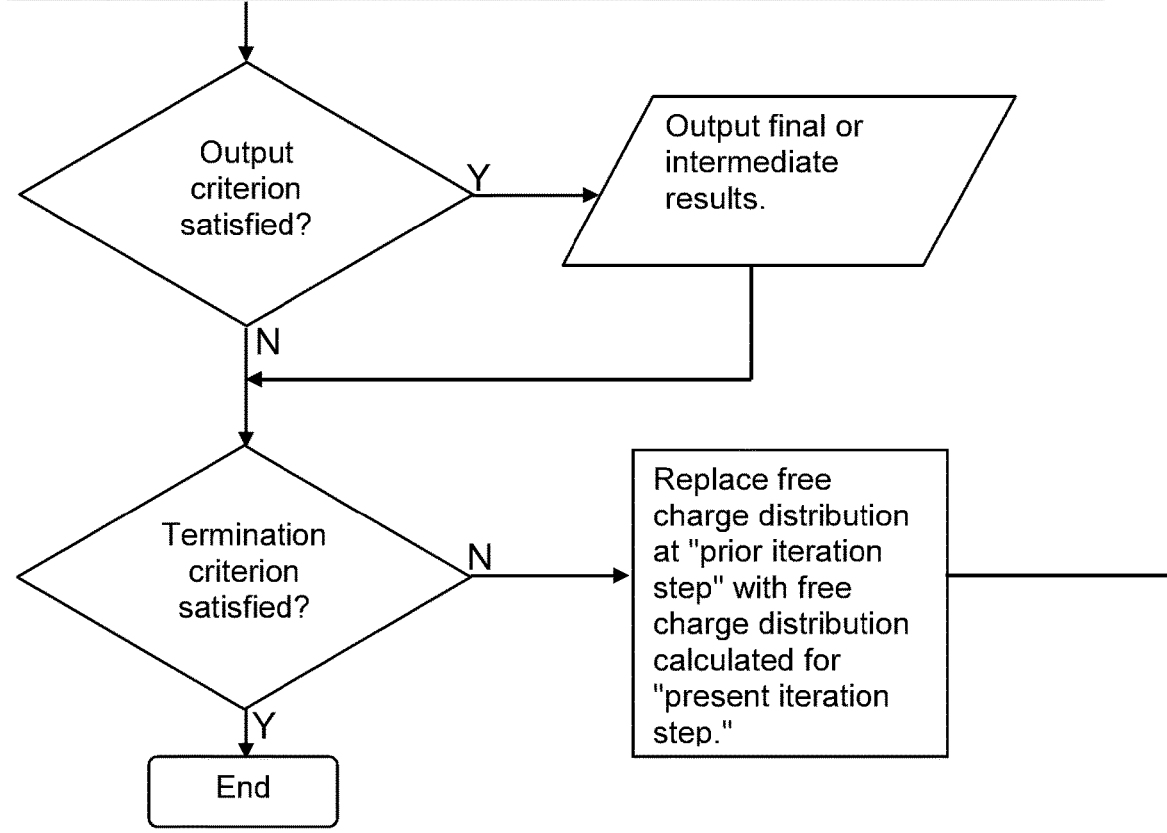
FIG. 6 is a representative flow chart for a steady state conductor simulation in accordance with an embodiment of the disclosure.
Figure 7:
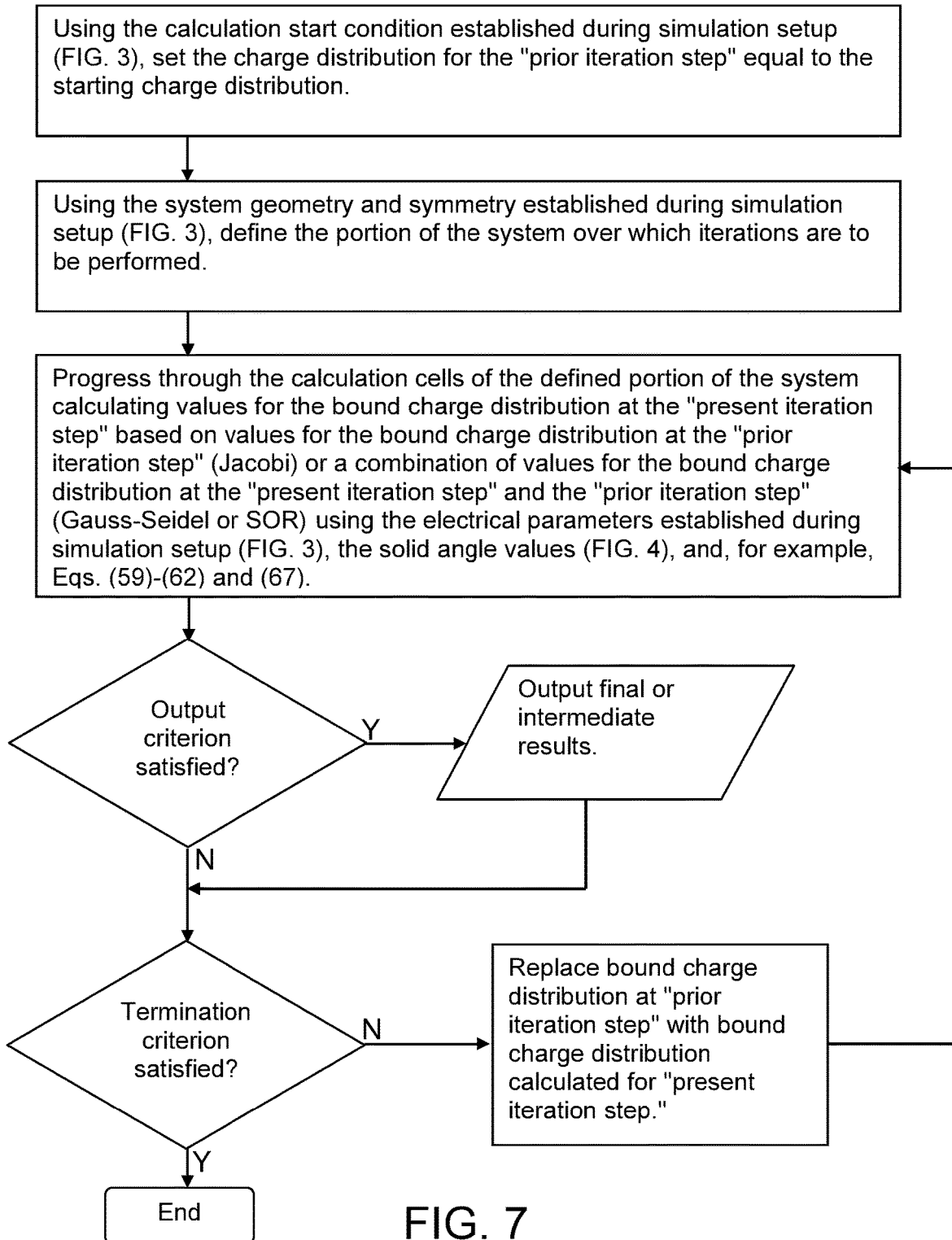
FIG. 7 is a representative flow chart for a dielectric simulation in accordance with an embodiment of the disclosure.
Figure 8:
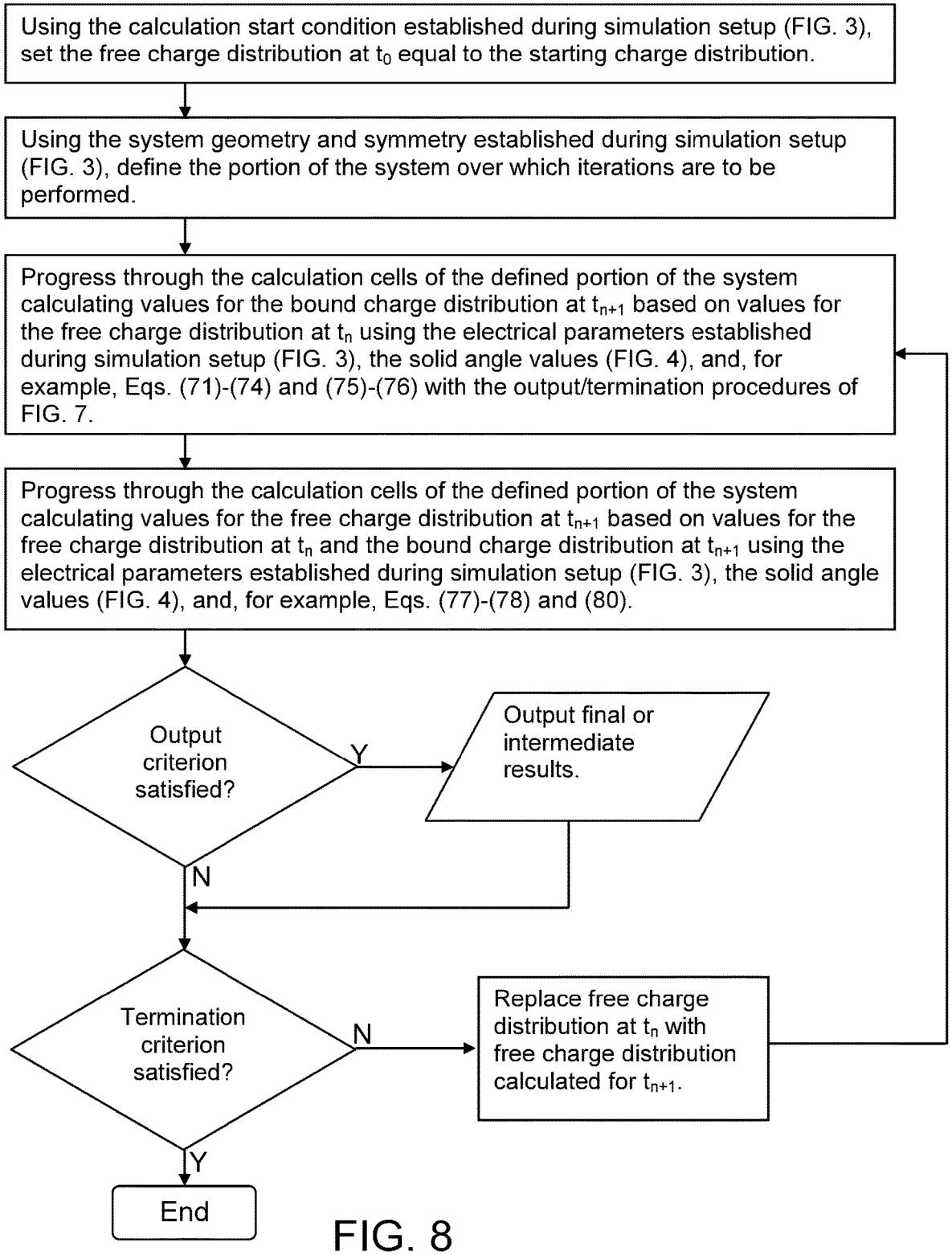
FIG. 8 is a representative flow chart for a dielectric/conductor simulation in accordance with an embodiment of the disclosure.

Once the solid angle values have been calculated, one or more simulations are performed using one or more of the representative flow charts of FIGS. 5-8. The choice of simulation to be performed will, of course, depend on the particular system being modeled and the electrophysiological phenomena of interest. In some cases, it may be desirable to perform an initial simulation taking into account both the system's conductive and dielectric properties (FIG. 8) and based on the results of that simulation switch to a simpler simulation such as a dielectric simulation (FIG. 7) or a conductor or steady state conductor simulation (FIGS. 5 and 6, respectively).

Once a charge distribution has been obtained, if desired, electrical potentials can be calculated using an equation of the form:

$$\Phi = (1/4\pi\varepsilon_0)\Sigma_i q_i/r_i \quad (99)$$

where $\Phi$ is the potential assuming the zero of potential is at infinity, the summation is over all quantities of charge in the system, i.e., all quantities of free and bound charge, and $r_i$ is the distance from the $i^{th}$ quantity of charge to the point at which the potential is being calculated. It should be noted that as in the '617/'466 patents, the improvements of this disclosure use the charge first process where charge distribution(s) are calculated first and only then (if desired) potentials are calculated from the charge distribution(s) as opposed to first determining electrical potential distribution(s) and then differentiating the potential distribution(s) to obtain charge distribution(s).

The steps set forth in the flow charts of FIGS. 3-8 or in other flow charts developed based on the present disclosure can be readily implemented using a variety of computer equipment and a variety of software programming languages, e.g., FORTRAN, which is well-suited for scientific calculations. In this regard, as is typical for scientific calculations, the charge distributions of the invention will normally be determined in at least double precision. Other programming languages that can be used in the practice of the disclosure include, without limitation, BASIC, PASCAL, C, C++, and the like. More than one programming language can be used in the practice of the disclosure if desired.

Output from the calculation process can be in electronic and/or hard copy form, and can be displayed in a variety of formats, including in tabular and graphical form. For example, graphs, including topographical graphs, can be prepared using commercially available data presentation software such as MICROSOFT's EXCEL program and/or R.

The computer-implemented tools of the disclosure can be provided to users on a non-transitory computer-readable medium with instructions stored thereon that, when executed by a processor, perform the steps of the solid angle process, the flattened calculation cell process, and/or the bound charge/free charge process. Non-limiting examples of such media include diskettes, CDs, flash drives, and the like. The processes of the disclosure can also be provided to users on-line through, for example, "cloud" computing. The processes can be performed on various computing platforms, including personal computers, workstations, mainframes, supercomputers, etc. In practice, the computer-implemented tools disclosed herein are able to model/simulate the electrical behavior of in vivo, in situ, and in vitro physiological systems, including, without limitation, nerves, muscles, tissues, organs, whole organisms, and single cell and multiple cell laboratory preparations.

VI. EXAMPLES

Without intending to limit its scope in any manner, the disclosure is further illustrated by the following examples.

Example 1

This example illustrates representative benefits associated with using the solid angle process. As discussed in the '617/'466 patents, Equations (1) and (2) of those patents result in some residual charge in the body of a conductor. The present example demonstrates that the solid angle process generates charges only in surface calculation cells of a conductor and not in the body of the conductor. Consequently, only the surface calculation cells need be included in the simulation when the solid angle process is used which significantly reduces computation time.

The problem of a point source in air above the center of a slab (rectangular parallelepiped) of a conductive material ($\sigma=0.5$ S/m; $\varepsilon_r=1.0$) was used to illustrate this effect. The slab was represented by 41×41×5 cubic calculation cells (total number of calculation cells equal to 8405). The point source was located at the center of a cubic calculation cell spaced three calculation cells above the calculation cells representing the upper surface of the slab facing the point source, i.e., when the calculation cells representing the lower surface of the slab are given the index 1, the calculation cells representing the upper surface of the slab have the index 5 and the calculation cell representing the point source has the index 9. The calculation cell containing the point source had zero conductivity, i.e., the point source was s charge. Steady state (ss) values were calculated and, in terms of calculation cells A and B of FIG. 2, $\sigma_A=0.5$ S/m and $\sigma_B=0$ at the interfaces of the slab with air. (Note that for this problem, the steady state solution is independent of the value of $\sigma_A$. The same is true for the free charge steady state solutions of the other examples.)

Figure 9:
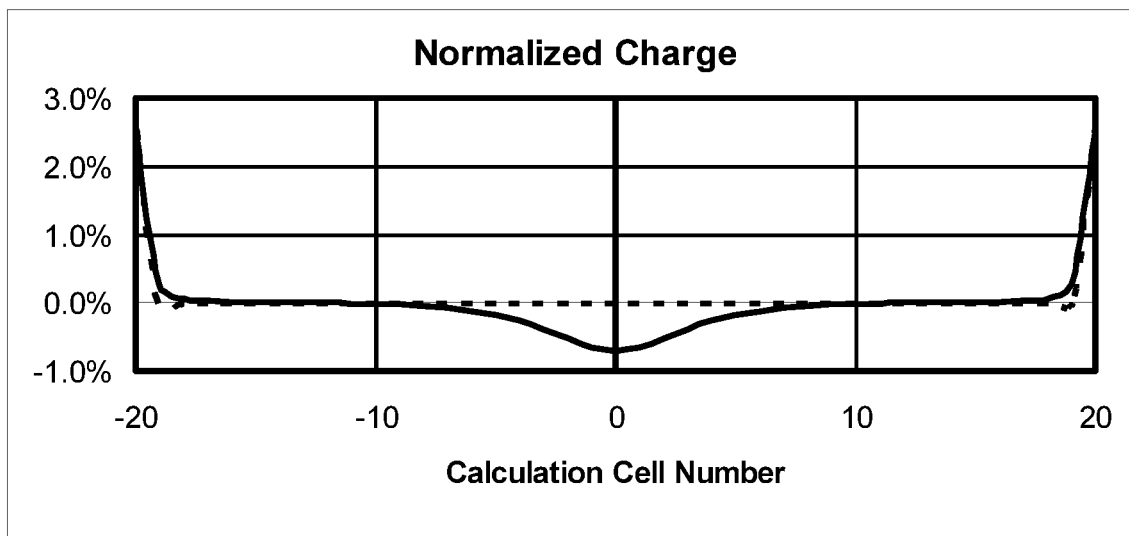
FIG. 9 is a plot of normalized, steady state, free charge in percent versus calculation cell number for an embodiment of the solid angle process ($\Omega$ process) of the present disclosure (dashed line) and the process of Equations (1) and (2) of the '617/'466 patents (solid line).

FIG. 9 shows the results of the simulations. In particular, this figure shows calculated quantities of free charge at steady state in a row of calculation cells that extends between two sides of the slab and is located at the middle of the slab, i.e., the row is located at index 3 when the lower surface of the slab has index 1 and the upper surface has index 5. In this figure, the quantity of free charge in the calculation cells has been normalized using the analytic solution for the steady state, free charge density $\Sigma^f_{analytic}{}^{(ss)}$ induced by a point source at the surface of a conductive body of semi-infinite extent. Assuming the point source is located on the z-axis of a Cartesian coordinate system whose origin is at the conductor's surface, $\Sigma^f_{analytic}{}^{(ss)}$ is given by:

$$\Sigma^f_{analytic}{}^{(ss)} = -(1/2\pi)q_0 d(x^2+y^2+d^2)^{-3/2}, \quad (100)$$

where d is the distance between the point source and the conductor's surface and $q_0$ is the point source's quantity of charge, a signed value. The maximum value of this function occurs at $x=y=0$ and is given by:

$$\Sigma^f_{max}{}^{(ss)} = -q_0/(2\pi d^2) \quad (101)$$

For the cubic calculation cells used in this example, the product of $\Sigma^f_{max}{}^{(ss)}$ times the area of a face of a calculation cell provides a convenient normalization factor for the calculated charge distributions since the product provides a measure of the maximum quantity of charge in a calculation cell. Thus, in FIG. 9, the values calculated by the simulation for the above middle row of calculation cells were divided by this product and then multiplied by 100 to give the percentage values shown in the figure.

The solid line in FIG. 9 represents the results achieved using the process of the '617/'466 patents, while the dashed line shows the results achieved using the solid angle process. Recalling that except at the edges of the slab, the charge should be zero, the improvement provided by the solid angle process (dashed line) is evident. Table 2 sets forth the values plotted in FIG. 9. The difference between the two processes is further illustrated in this table, with the largest non-edge normalized value for the process of the '617/'466 patents being $7.1092 \times 10^{-1}$, while that for the solid angle process is only $1.6176 \times 10^{-9}$, almost a billion times smaller.

The small values for internal calculations cells for the solid angle process allows those internal calculation cells to be skipped in the simulation. For the system of this example, this reduces the number of calculation cells needed to represent the conductive slab from 8,405 to 3,842, a reduction of 54%.

Although the calculations reported in this example were for a conductor, the same improvement results when the solid angle process is used for dielectrics or conductive dielectrics. It should be noted that the electric fields of this example are conservative electric fields, i.e., fields whose effects on a spatial charge distribution can be represented by a $1/r^2$ law. The solid angle process is based on the $1/r^2$ law but uses it more accurately than the process of the '617/'466 patents as shown by the above results.

Example 2

This example calculates the steady state distribution of free charge on the surface of a conductive cube and uses that distribution as a benchmark for determining the accuracy of the $\Omega\delta \to 0$ processes. This system serves as a benchmark because, as discussed below, a capacitance value for a conductive cube can be calculated from the free charge distribution and, while there is no analytic solution for the capacitance of a conductive cube, upper and lower bounds are known. Specifically, upper and lower bounds have been obtained for the normalized capacitance $C_{norm}$ of a conductive cube in a non-conductive medium, where $C_{norm}$ is given by:

$$C_{norm}=C/(4\pi\varepsilon_0 a), \quad (102)$$

where a is the edge length of the cube and C is the capacitance for that edge length. As reported by Wintle, H. J., "The capacitance of the cube and square plate by random walk methods," *J. Electrostatics*, vol. 62, pp. 51-62, 2004, $C_{norm}$ is bounded between 0.6596 and 0.6691.

Using the $\Omega\delta \to 0$ processes and square-shaped, flattened calculation cells, capacitance values were determined for a conductive cube of a fixed edge length as a function of the number (n) of calculation cells per edge of the cube, with n being varied between 3 and 71 and thus the total number of flattened calculation cells varying between 54 ($3\times3\times6$) and 30,246 ($71\times71\times6$). Larger values of n could, of course, have been used, but as will be shown below, the normalized capacitance became asymptotic well before n=71.

The total charge Q introduced into the cube was held constant for all of the simulations. Steady state solutions were obtained using Eqs. (41)-(44) with $\sigma_{\mathit{diff}}=\sigma_{sum}=\sigma_A$ and all of the $q_i^{f(ss)}$'s, $q_k^{s(ss)}$'s, and $V_K^{(ss)}$'s equal to zero. Jacobi iteration was performed and as a starting point for the iteration, the total charge Q was divided equally among all of the flattened calculation cells making up the surface of the cube. Voltages were calculated at the center of the cube using Eq. (99) and capacitance values were calculated by dividing the total charge by the calculated voltage (C=Q/Φ). The capacitance values calculated in this way were then converted to normalized capacitance values using Eq. (102).

Figure 10:
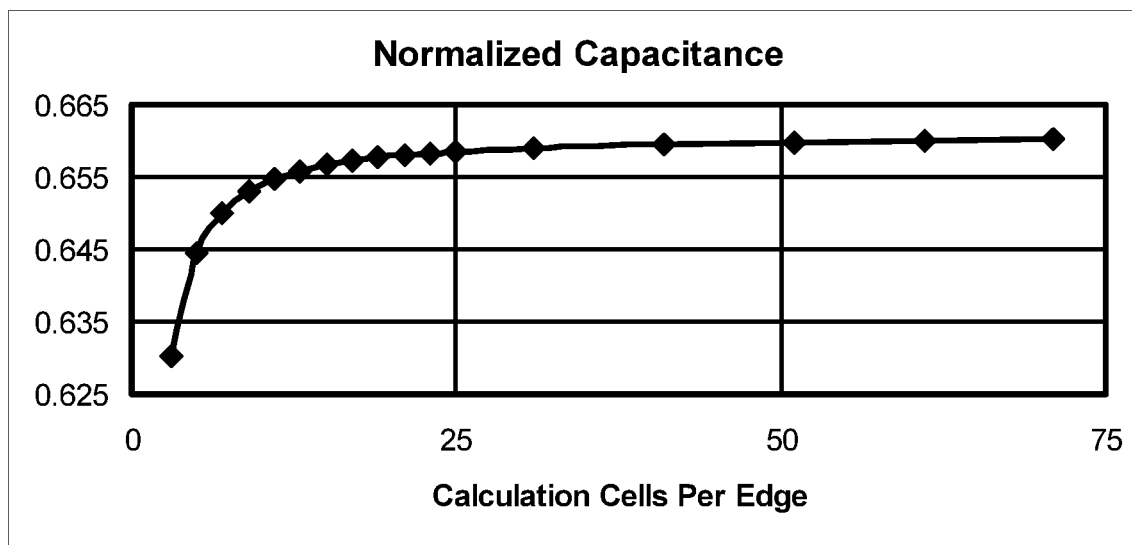
FIG. 10 is a plot of normalized capacitance versus the number of calculation cells per edge of a conductive cube. The normalized capacitance values were obtained using an embodiment of the solid angle and flattened calculation cell processes ($\Omega\delta\rightarrow 0$ processes) of the present disclosure.

The results are shown in FIG. 10. As can be seen in this figure, the normalized capacitance rises rapidly as the number of calculation cells increases, reaching a value of 0.6601 for n=71. Wintle's lower bound of 0.6596 is reached for n=41. Importantly, even with as few as 3 calculation cells per edge, the calculated $C_{norm}$ value is within 5% of the 0.6601 value for n=71 (i.e., $C_{norm}$=0.6303 for n=3) and is within 1% for 11 calculation cells (i.e., $C_{norm}$=0.6546 for n=11).

The results of these simulations show that the $\Omega\delta \to 0$ processes easily pass the conductive cube benchmark test and even very small numbers of flattened calculation cells provide at least qualitatively accurate results.

Example 3

In this example and in Examples 4 and 5, a point source outside of a cube is used to illustrate various aspects of the present disclosure. In this example, the cube is conductive ($\sigma$>0), but non-polarizable ($\varepsilon_r$=1), while in Example 4, the cube is polarizable ($\varepsilon_r$>1), but non-conductive ($\sigma$=0), and in Example 5, the material making up the cube is both conductive and polarizable ($\sigma$>0, $\varepsilon_r$>1).

The $\Omega\delta \to 0$ processes were used in each of these examples. In Example 5, the bound charge/free charge process was also used. Except where the effects of the fineness of the discretization was being examined (see FIGS. 14 and 16), each of the six surfaces of the cube was divided into 41×41 square-shaped, flattened calculation cells and the point source was placed 4 units above the center of the cube's top surface, where a unit was equal to the edge length of the cube divided by the number of calculation cells per edge, i.e., in the notation of Example 2, a unit equaled a/n. When fineness of the discretization was being examined, the number of calculation cells per edge was increased with the point source still at its location for the n=41 case.

Figure 11:
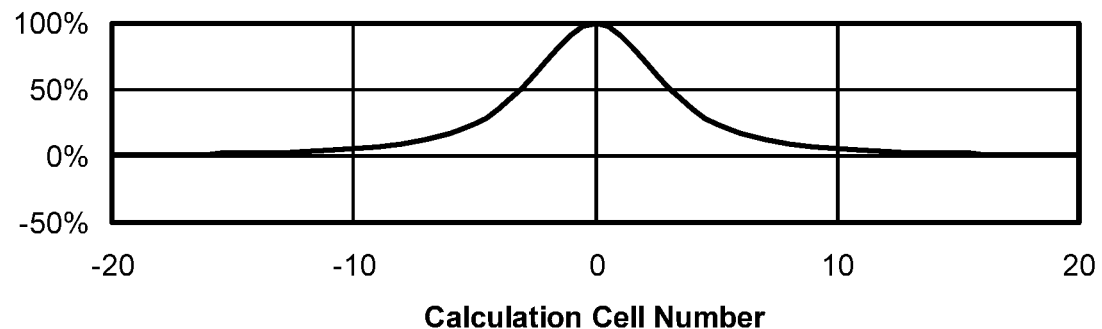
FIG. 11 is a plot of normalized, steady state, free charge in percent versus calculation cell number for the analytic solution for a point source above a semi-infinite conductive volume.

Because these examples used flattened calculation cells, rather than cubic calculation cells, normalization of charge distributions (both free and bound) was performed slightly differently than in Example 1. Specifically, the quantity of charge calculated for a flattened calculation cell was divided by the area of a face of the calculation cell to give a charge density value which was multiplied by 100 and divided by $\Sigma_{max}^{f(ss)}$ of Eq. (101) to give a percentage value (the normalized charge value). FIG. 11 shows the results of applying this normalization process to the analytical charge distribution of Eq. (100) evaluated at the locations (centers) of calculation cells along a midline of the top surface of the cube. As can be seen, the normalized free charge distribution for the analytic solution is 100% directly under the point source (the 0 calculation cell) and drops off rapidly to essentially 0% as one moves outward from that location, but never becomes negative.

Figure 12:
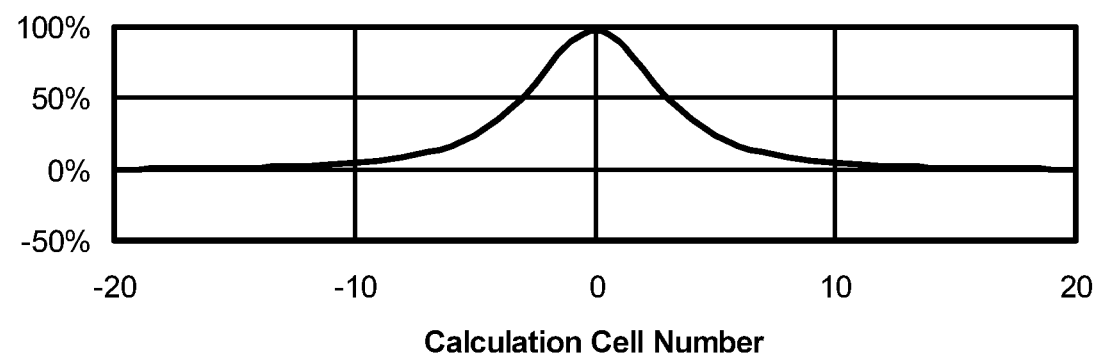
FIG. 12 is a plot of normalized, steady state, free charge in percent versus calculation cell number for a point source above a conductive cube. The charge distribution was obtained using an embodiment of the $\Omega\delta\rightarrow 0$ processes of the present disclosure.

FIG. 12 shows the results obtained using the $\Omega\delta \to 0$ processes. In particular, Eqs. (41)-(44) were used with: (1) $\sigma_{\mathit{diff}}=\sigma_{sum}=\sigma_A$, (2) the $V_K^{(ss)}$'s and the $q_i^{f(ss)}$'s equal to zero, and (3) $q_k^{s(ss)}$ equal to and located at the $q_0$ of Eqs. (100) and (101). Jacobi iteration was performed to determine the steady state, free charge distribution. As a starting point for the iterative process, the quantity of free charge in all of the flattened calculation cells making up the surface of the cube was set equal to zero. As can be seen in FIG. 12, the normalized free charge distribution calculated using the $\Omega\delta \to 0$ processes is essentially identical to the analytic solution of FIG. 11.

Figure 13:
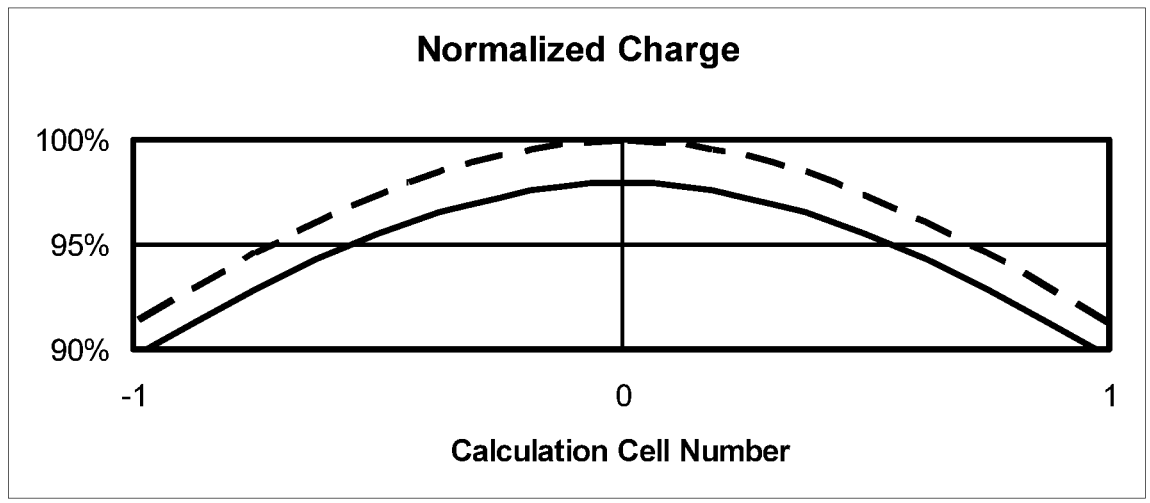
FIG. 13 is a plot comparing the steady state, free charge distribution of FIG. 11 (dashed line; analytic solution) with the steady state, free charge distribution of FIG. 12 (solid line; $\Omega\delta\rightarrow 0$ processes) around calculation cell 0.

The distributions, however, differ slightly in the following two ways. First, the analytical solution gives peak values, while the $\Omega\delta\to 0$ processes, specifically, the solid angle process, gives integrated/averaged values. This is illustrated in FIG. 13 which is an expanded view around calculation cell 0 for the analytic distribution of FIG. 11 (dashed curve) and the distribution of FIG. 12 for the $\Omega\delta\to 0$ processes (solid curve). As can be seen, the value that results from the use of solid angles (solid curve) is smaller than the peak value that results from the analytic solution (dashed curve), the absolute value of the difference in this case being ~2%.

Figure 14:
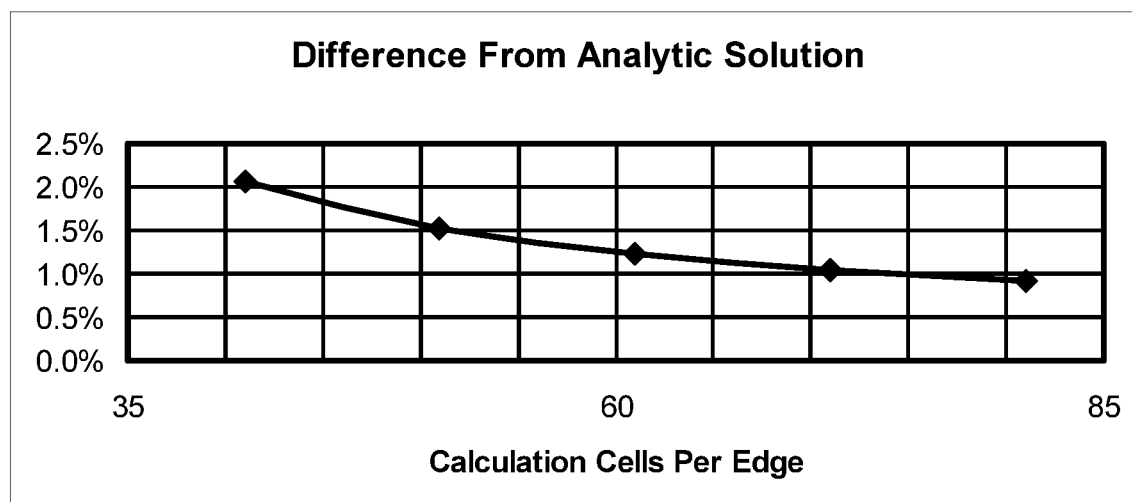
FIG. 14 is a plot illustrating how the difference between the solid line and the dashed line of FIG. 13 changes (becomes smaller and then asymptotic) as the number of calculation cells per edge used in the $\Omega\delta\rightarrow 0$ processes is increased.

As shown in FIG. 14, this difference between the two distributions becomes smaller as the discretization becomes finer. Specifically, FIG. 14 plots the absolute value of the difference between the normalized charge density for calculation cell 0 obtained using the $\Omega\delta\to 0$ processes and that of the analytic solution as a function of the number of calculation cells along the edge of the cube. The first data point corresponds to the absolute value of the difference shown in FIG. 13 where n=41 and the remaining data points show the results for n=51, 61, 71, and 81. The absolute value of the difference between the two normalized charge distributions drops below 1% for n=81. As can be seen in FIG. 14, the difference becomes asymptotic as n increases since the $\Omega\delta\to 0$ processes are solving the problem of a point source above a finite cube, not above a semi-infinite volume, and thus the two solutions are not, and should not be, identical.

Figure 15:
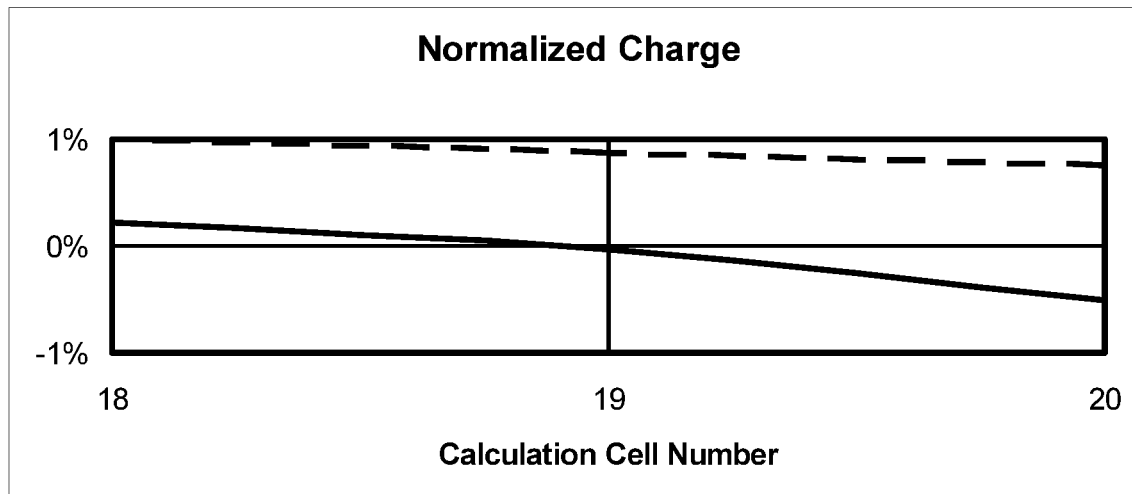
FIG. 15 is a plot comparing the steady state, free charge distribution of FIG. 11 (dashed line; analytic solution) with the steady state, free charge distribution of FIG. 12 (solid line; $\Omega\delta\rightarrow 0$ processes) around calculation cell 20.
Figure 16:
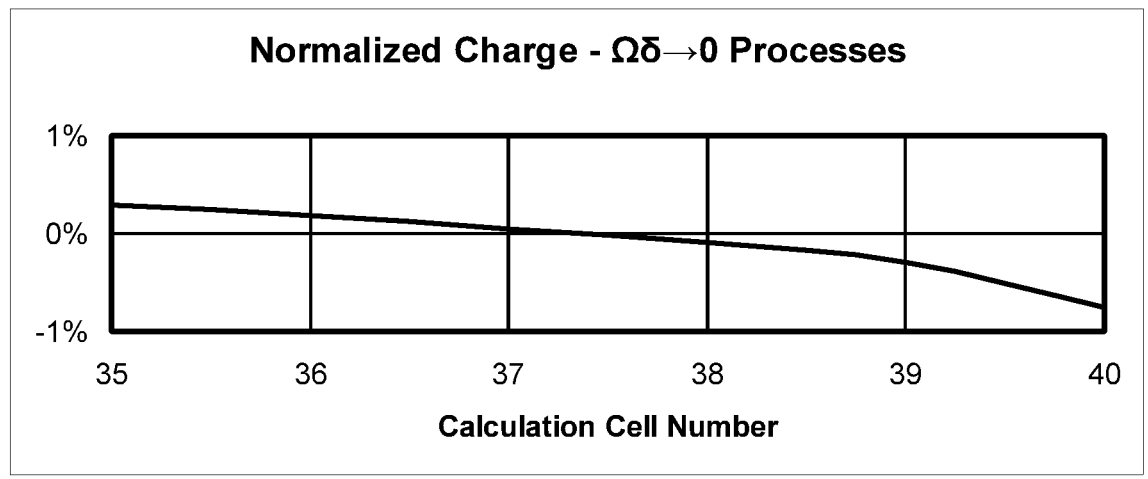
FIG. 16 is a plot of normalized, steady state, free charge in percent versus calculation cell number for a point source above a conductive cube. The charge distribution was obtained using an embodiment of the $\Omega\delta\rightarrow 0$ processes of the present disclosure with the number of calculation cells per edge of the conductive cube equal to 81. The plot shows the charge distribution around calculation cell 40.

The second difference between the $\Omega\delta\to 0$ processes and the analytic solution also arises because the charge distribution of the $\Omega\delta\to 0$ processes is for a finite cube, while the analytic solution is for a conductive body of semi-infinite extent. This difference is illustrated in FIG. 15 which is an expanded view of the normalized free charge distributions around calculation cell 19 for the analytic solution of FIG. 11 (dashed curve) and the $\Omega\delta\to 0$ processes of FIG. 12 (solid curve). As can be seen, the solution according to the $\Omega\delta\to 0$ processes changes sign as it approaches the edge of the cube (calculation cell 20), while the analytic solution does not. That is, for the finite cube, the induced charge distribution at the top surface of the cube has one sign near the edges of the top surface and the opposite sign in the body of the surface. FIG. 16 further illustrates this effect for a finer discretization, i.e., the number of calculation cells per edge in FIG. 16 was 81, instead of 41 as in FIG. 15.

This reversal in sign also occurs for the bottom and side surfaces of the finite cube (data not shown). That is, like the edges of the top surface, the charge distributions of the bottom and side surfaces of the cube are of the opposite sign to the charge distribution in the body of the top surface. In this way, no net free charge is induced in the cube by the external point source, i.e., the induced positive and negative free charges are in balance with one another.

A further simulation was performed for the $\sigma>0$, $\varepsilon_r=1$ case in which the time course of the development of quantities of free charge at the surface of the cube was calculated. Instead of Eqs. (41)-(44), Eq. (32) was used, which for this simulation, with $I^f_A(t_n)$ equal to zero for all $t_n$, became:

$$q^f_{A(\sigma_B=0)}(t_{n+1}) = (1 - \Delta t \sigma_A / 2\varepsilon_0) q^f_{A(\sigma_B=0)}(t_n) - (\Delta t \sigma_A / 4\pi\varepsilon_0) \\ (\Sigma_{i\neq A,B} q^f_{i(\sigma_B=0)}(t_n) \Omega_{a\leftarrow i} + q_0 \Omega_{a\leftarrow 0}), \quad (103)$$

where $q_0$ is the $q_0$ of Eqs. (100) and (101). As discussed in connection with Eq. (26), for this simulation with $\sigma_B=0$, the free charge in the B cells was given by:

$$q^f_{B(\sigma_B=0)} = 0, \quad (104)$$

for all of the B cells and all $t_n$.

$\sigma_A$ in Eq. (103) was given a value of 0.5 S/m which is representative of a biological medium and makes the relaxation time ($\tau$-sigma) of the conductive medium equal to $1.77\times 10^{-11}$ seconds ($\tau$-sigma=$\varepsilon_0/\sigma_A$). A $\Delta t$ of $1.77\times 10^{-12}$ seconds was found suitable for the simulation, i.e., $\Delta t = \tau$-sigma/10, although other time steps can be used if desired. The initial free charge distribution (t=$t_0$) was zero free charge in all of the flattened calculation cells making up the surface of the cube.

Figure 17:
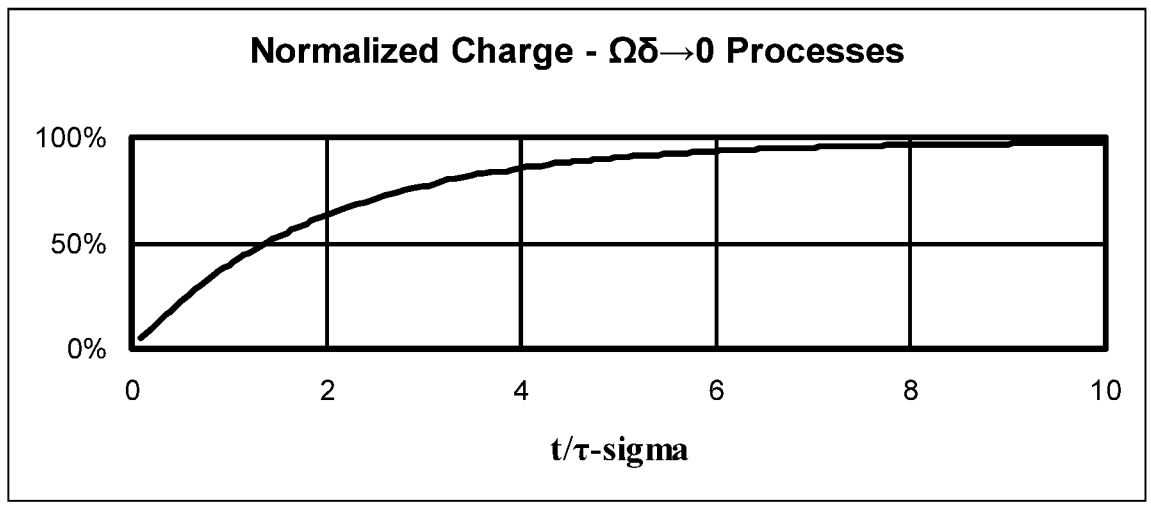
FIG. 17 is a plot of normalized free charge in percent versus time in units of $\tau$-sigma for a point source above a conductive cube. The time series was obtained using an embodiment of the $\Omega\delta\rightarrow 0$ processes of the present disclosure and is for calculation cell 0.

The results are shown in FIG. 17 where normalized quantities of free charge at the center of the top surface of the conductive cube is plotted versus time in units of $\tau$-sigma. As set forth in Klee 2014 (see Equation (27)), the analytic solution for the corresponding point for a semi-infinite conductor is given by:

$$\Sigma^f(t) = \Sigma^{f(ss)}_{max}(1 - e^{-t/\tau}), \quad (105)$$

where, for $\varepsilon_r=1$, $\tau$ in this equation equals $2\tau$-sigma (see Equation (22) of Klee 2014). For a conductivity of 0.5 S/m, the analytic $\tau$ is thus $3.54\times 10^{-11}$ seconds.

Figure 18:
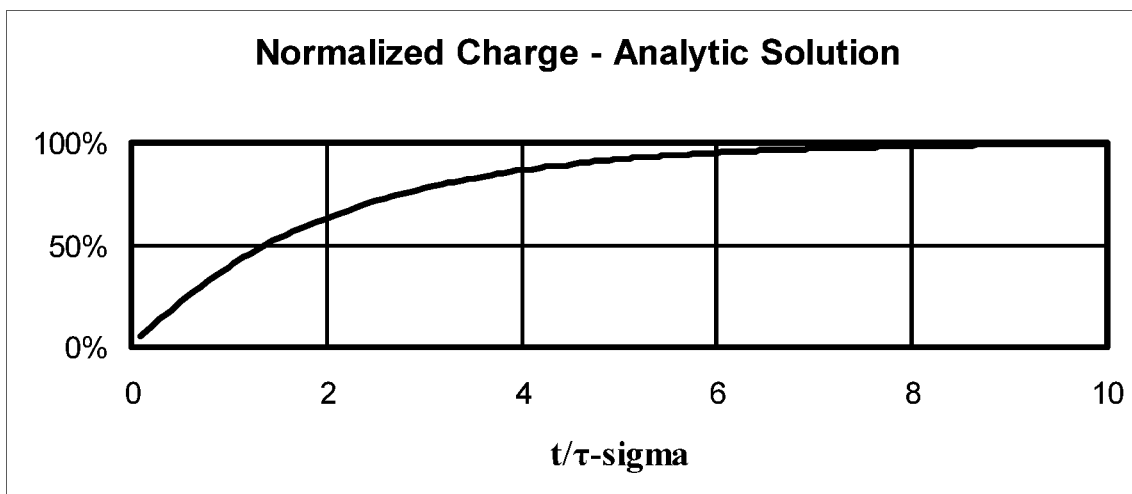
FIG. 18 is a plot of normalized free charge in percent versus time in units of $\tau$-sigma for the analytic solution for a point source above a semi-infinite conductive volume. The plotted values are for the center of calculation cell 0.
Figure 19:
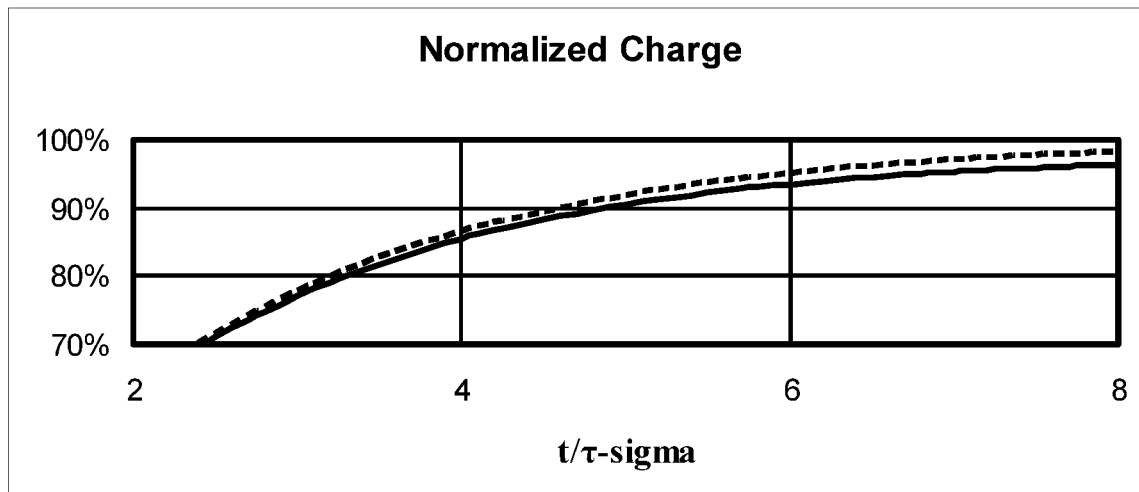
FIG. 19 is a plot comparing the time series of FIG. 18 (dashed line; analytic solution) with the times series of FIG. 17 (solid line; $\Omega\delta\rightarrow 0$ processes) for the time period between 2$\tau$-sigma and 8$\tau$-sigma.
Figure 20:
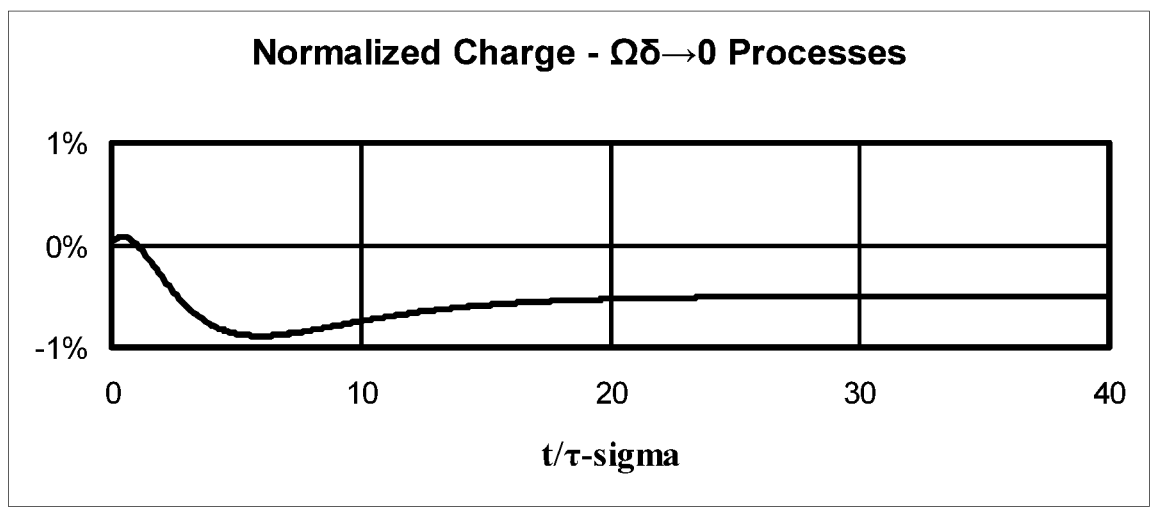
FIG. 20 is a plot of normalized free charge in percent versus time in units of $\tau$-sigma for a point source above a conductive cube. The time series was obtained using an embodiment of the $\Omega\delta\rightarrow 0$ processes of the present disclosure and is for calculation cell 20.

FIG. 18 is a plot of $100\cdot\Sigma^f(t)/\Sigma^{f(ss)}_{max}$ over the same time period as FIG. 17. As can be seen, the time courses are essentially identical. However, as with the spatial distributions, there are slight differences in the time courses due to the differences in the problems being solved. These differences are illustrated in FIGS. 19 and 20. Specifically, FIG. 19 is an expanded view of the center portions of FIGS. 17 and 18, where the solid curve is the solution for the finite cube using the $\Omega\delta\to 0$ processes, while the dashed curve is the analytic solution for the semi-infinite conductor. As can be seen, the solution for the semi-infinite conductor rises somewhat faster than that for the finite cube, thus achieving the larger magnitude compared to the finite cube for the analytic steady state solution for the center point shown in FIG. 13.

FIG. 20 shows the complex behavior of the charges at the edge of the cube, specifically, calculation cell 20. As can be seen, the normalized charge starts out positive, changes sign, reaches it maximum absolute value at about t=5·$\tau$-sigma, and finally reaches its asymptotic value (see FIG. 15) at ~20-30 $\tau$-sigma. This complex behavior results from feedback between portions of the cube that develop positive normalized charge (the body of the top surface of the cube) and portions that develop negative normalized charge (the edges of the top surface and all of the bottom and side surfaces). The spatial relationships among these portions and between the portions and $q_0$ differ, thus leading to interactions that vary with time as the feedback process moves the charges for all of the portions into their steady state positions and values.

Example 4

As discussed above in Example 3, this example is directed to the case where the point source is outside of a cube that is polarizable but not conductive (a dielectric cube), as opposed to a cube that is conductive but not polarizable (a conductive cube) as in Example 3. The geometry, discretization, and normalization were the same as in Example 3, but instead of solving Eqs. (41)-(44), Eqs. (55)-(58) were solved, again using a Jacobi iteration with the starting point for the iteration, in this case, being zero bound charge in all of the flattened calculation cells making up the surface of the cube. Like Eqs. (41)-(44), Eqs. (55)-(58) employ the $\Omega\delta\to 0$ processes.

From Klee 2014, specifically, Equation (28) evaluated at t=0, the analytic solution for a point source above a semi-infinite dielectric is given by:

$$\Sigma^b_{analytic} = [(\varepsilon_r - 1)/(\varepsilon_r + 1)] \Sigma^{f(ss)}_{analytic}, \quad (106)$$

which using Eq. (101) can be written:

$$\Sigma^b_{analytic} = [(\varepsilon_r-1)/(\varepsilon_r+1)]\Sigma f_{max}^{(ss)} d^3(x^2+y^2+d^2)^{-3/2}, \quad (107)$$

or in normalized form:

$$\Sigma^b_{analytic-normalized} = 100[(\varepsilon_r-1)/(\varepsilon_r+1)]d^3 (x^2+y^2+d^2)^{-3/2}. \quad (108)$$

Figure 21:
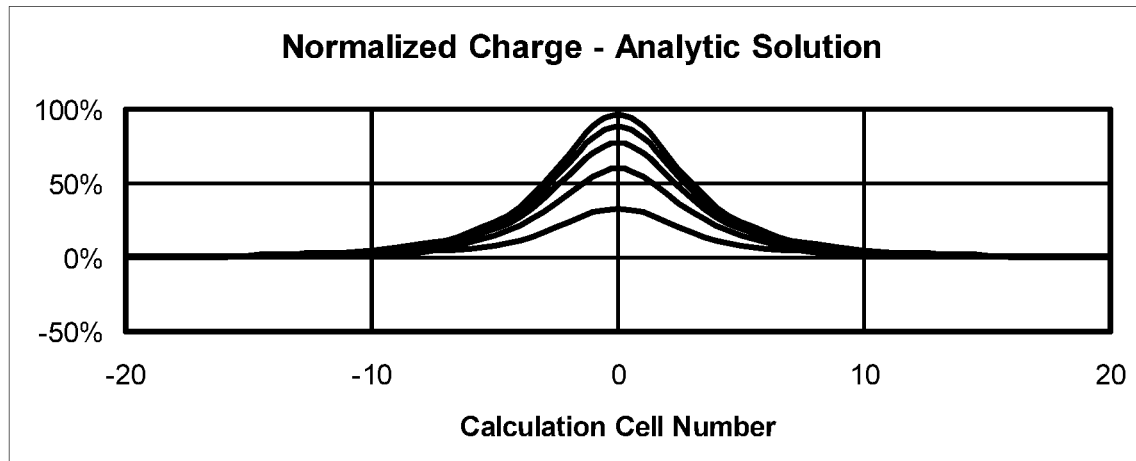
FIG. 21 is a plot of normalized bound charge in percent versus calculation cell number for the analytic solution for a point source above a semi-infinite dielectric volume. The five curves (bottom to top) are for $\varepsilon_r$ values of 2, 4, 8, 16, and 64.
Figure 22:
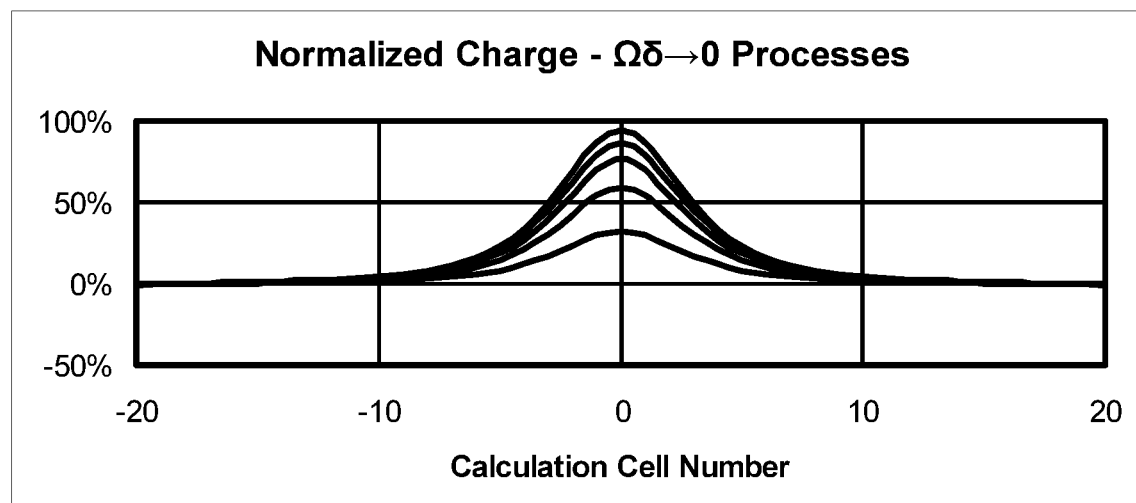
FIG. 22 is a plot of normalized bound charge in percent versus calculation cell number for a point source above a dielectric cube. The charge distribution was obtained using an embodiment of the $\Omega\delta\rightarrow 0$ processes of the present disclosure. The five curves (bottom to top) are for $\varepsilon_r$ values of 2, 4, 8, 16, and 64.

FIG. 21 shows Eq. (108) evaluated for $\varepsilon_r$ values of 2, 4, 8, 16, and 64 (bottom to top curves), while FIG. 22 shows the results obtained using Eqs. (55)-(58) with $g^m{}_K$ for all K's given by:

$$g^m{}_K = -[(\varepsilon_r^m-1)/(\varepsilon_r^m+1)][(\tfrac{1}{2}\pi)q_0], \quad (109)$$

where again the five curves (bottom to top) are for $\varepsilon_r$ values of 2, 4, 8, 16, and 64.

As can be seen in FIG. 22, the normalized bound charge distributions calculated using the $\Omega\delta\to 0$ processes are essentially identical to the analytic solutions of FIG. 21. The same differences illustrated in FIGS. 11-16 for the free charge distributions, i.e., smaller magnitudes for the $\Omega\delta\to 0$ processes and sign reversals at the edges of the top surface of the cube and for the bottom and sides of the cube, exist for the bound charge distributions (data not shown).

Comparing FIG. 22 with FIG. 12, we can see that as $\varepsilon_r^m$ becomes large, the bound charge distribution for a non-conductive, polarizable cube induced by a point source approaches the steady state, free charge distribution for a conductive, non-polarizable cube subjected to the same point source. This can be seen from Eqs. (33) and (52) which for the particulars of FIG. 22 and FIG. 12 can be written:

$$q^f_A{}^{(ss)} = -(\tfrac{1}{2}\pi)[\Sigma_{i\ne A} q^{f(ss)}_i \Omega_{a\leftarrow i} + q_0\Omega_{a\leftarrow 0}], \text{ and} \quad (110)$$

$$q^{b-m}_A = -(\tfrac{1}{2}\pi)[\Sigma_{i\ne A} q^{b-m}_i \Omega_{a\leftarrow i} + q_0\Omega_{a\leftarrow 0}][(\varepsilon_r^m-1)/(\varepsilon_r^m+1)]. \quad (111)$$

As $\varepsilon_g^m \to \infty$, the last factor of Eq. (111), i.e., the $(\varepsilon_r^m-1)/(\varepsilon_r^m+1)$ factor, approaches one, thus causing the bound charge distribution of that equation to approach the free charge distribution of Eq. (110).

Example 5

As discussed above in Example 3, this example is directed to the case where the point source is outside of a cube that is both conductive and polarizable, and thus the example illustrates the bound charge/free charge process, as well as the $\Omega\delta\to 0$ processes.

$\sigma_A$ was given a value of 0.5 S/m and $\varepsilon_r^K$ was given a value of 80, both of which are representative of a biological medium. The geometry, discretization, and normalization were the same as in Examples 3 and 4, and the $\Delta t$ was the same as in Example 3, but now the simulation alternated between bound charge and free charge calculations with Eqs. (71)-(74) being solved first for the quantities of bound charge at time $t_{n+1}$ followed by solving Eq. (79) for the quantities of free charge at $t_{n+1}$ using the newly-calculated quantities of bound charge at $t_{n+1}$ and the previously-calculated quantities of free charge at $t_n$. Specifically, for the particulars of this simulation, Eqs. (71)-(74) and (79) become:

$$Bq^b(t_{n+1}) = g(t_n), \quad (112)$$

where:

$$b_{KK} = 1, \quad (113)$$

$$b_{KL} = (\varepsilon_r^K - 1)/(\varepsilon_r^K + 1)(\tfrac{1}{2}\pi)\Omega_{K\leftarrow L}, \quad (114)$$

$$g_K(t_n) = -[(\varepsilon_r^K-1)/(\varepsilon_r^K+1)][q^f{}_K(t_n) + (\tfrac{1}{2}\pi)\Sigma_{i\ne K}q^f_i(t_n)\Omega_{K\leftarrow i} + (\tfrac{1}{2}\pi)q_0\Omega_{K\leftarrow 0}], \quad (115)$$

and $$q^f_{A(\sigma_B=0)}(t_{n+1}) = (1 - \Delta t\sigma_A/2\varepsilon_0)q^f_{A(\sigma_B=0)}(t_n) - (\Delta t\sigma_A/2\varepsilon_0) \quad (116)$$

$$q^b_{A(\sigma_B=0)}(t_{n+1})$$

$$-\Delta t\sigma_A/4\pi\varepsilon_0 \sum_{i\ne A,B} \left(q^f_{i(\sigma_B=0)}(t_n) + q^b_{i(\sigma_B=0)}\right)$$

$$(t_{n+1})\Omega_{a\leftarrow i} - \Delta t[\sigma_A/4\pi\varepsilon_0(q_0)\Omega_{a\leftarrow 0}].$$

Eqs. (112)-(115) were solved using a Jacobi iteration with the starting point for the first Jacobi iteration of the first time step ($t=t_1$) being zero bound charge in all of the flattened calculation cells making up the surface of the cube and thereafter being the quantities of bound charge in the cells calculated in the prior time step. The initial free charge distribution ($t=t_0$) was zero free charge in all of the flattened calculation cells making up the surface of the cube.

Bound charge iterations were stopped when the magnitude of the change in the quantity of bound charge per iteration for each of the calculation cells dropped below $1\times10^{-6}$ elementary charges for $q_0$ equal to 100 elementary charges. Convergence of the bound charge to this termination criterion was achieved in 23 steps for the $t_1$ calculation. Thereafter, because the final bound charge distribution for the $t_n$ time step was used as the starting point for Jacobi iteration for the $t_{n+1}$ time step and because the free charge distribution changed slowly with time for the chosen $\Delta t$ (i.e., $\Delta t = \tau$-sigma/10), that starting point was close to the final bound charge distribution and thus the number of iterations needed to satisfy the termination criterion drop rapidly, specifically, for the particulars of this simulation, to 9 iterations for time steps 2 through ~360, to 8 iterations for time steps ~360 to ~740, and so forth until just 2 iterations were needed for approximately the 3,400[th] time step and thereafter until the simulation was completed at 4,000 time steps.

Figure 23:
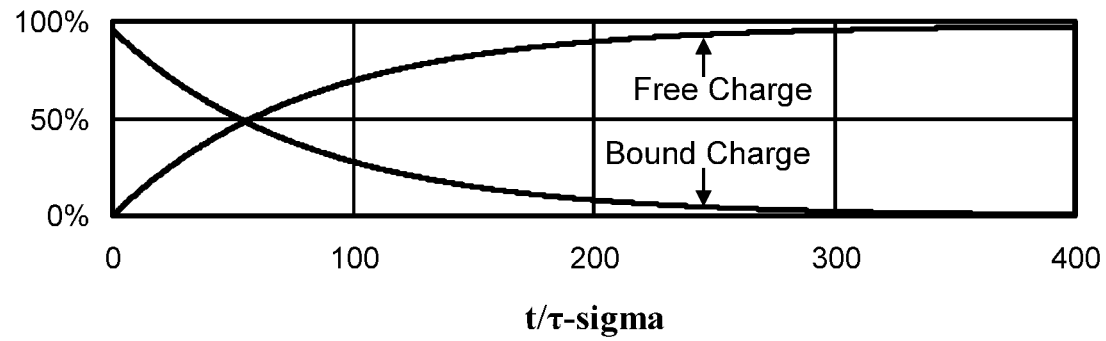
FIG. 23 is a plot of normalized free charge and normalized bound charge in percent versus time in units of $\tau$-sigma for a point source above a conductive/dielectric cube. The time series were obtained using an embodiment of the $\Omega\delta\rightarrow 0$ and bound charge/free charge processes of the present disclosure and are for calculation cell 0.
Figure 24:
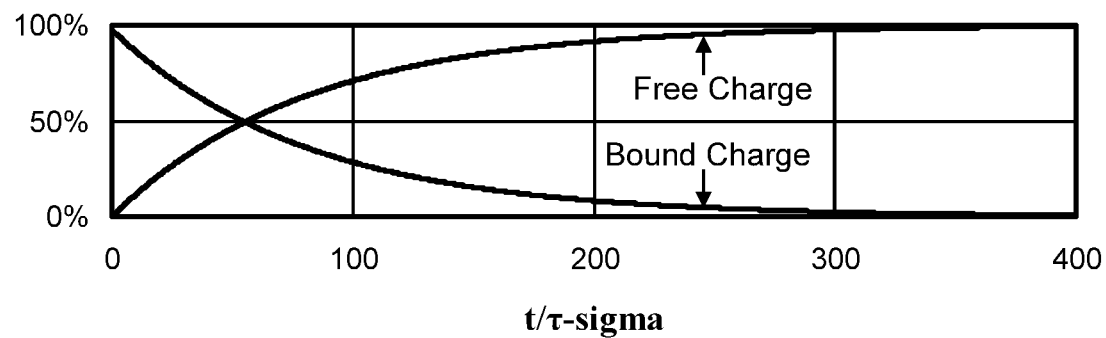
FIG. 24 is a plot of normalized free charge and normalized bound charge in percent versus time in units of $\tau$-sigma for the analytic solution for a point source above a semi-infinite conductive/dielectric volume. The plotted values are for the center of calculation cell 0.

FIG. 23 shows the results for this example. Specifically, in this figure, the normalized quantities of free charge and bound charge at the center of the top surface of the conductive/dielectric cube are plotted versus time in units of $\tau$-sigma. FIG. 24 shows the results for the analytic solution for the corresponding point for a semi-infinite conductor/dielectric (see Equations (27)-(28) and FIG. 5 of Klee 2014). Note the longer time course of these figures compared to that of FIGS. 17 and 18. This longer time course is the result of the relative dielectric constant being equal to 80, as opposed to 1 as in FIGS. 17 and 18.

As with the comparisons of Examples 3 and 4, a comparison of FIGS. 23 and 24 shows that the solution provided by the processes of the present disclosure is essentially identical to the analytic solution. In both cases, the free charge starts at zero and rises to a steady state value while the bound charge starts high and declines to zero. (It should be noted that at steady state, the bound charge can be greater than zero when the bound charge is located in a non-conductive medium.) Again, there are the slight differences, detailed above in Examples 3 and 4, between the two solutions as a result of the analytic solution being for a semi-infinite volume instead of a finite cube. For example, the normalized, steady state, quantity of free charge at the center of the top surface of the finite cube is smaller than the 100% value of the analytic solution. Similarly, the time courses are slightly different.

Interestingly, the time course differences between FIGS. 23 and 24 are smaller than those shown in FIGS. 19 and 20 for the conductive, non-polarizable case. These reduced differences result from the fact that for $\varepsilon_r^K=80$, the initial calculation of the bound charge distribution (the calculation for the $t_1$ time step) contains essentially all of the spatial differences between the solutions for the two problems, e.g., the existence of charges of opposite sign near the edges of the top surface and at the bottom and side surfaces of the finite cube. Thereafter, as time progresses, quantities of free charge essentially simply replace quantities of bound charge at the locations of the bound charge established by the initial calculation. For example, instead of seeing a biphasic time course for calculation cell 20 like that shown in FIG. 20 for a conductive cube, for a conductive/dielectric cube with a large dielectric constant, the quantity of free charge for calculation cell 20 simply increases monotonically as it replaces the quantity of bound charge at that location which already has a negative value compared to the value at the center of the top surface of the cube. This replacement of quantities of bound charge by quantities of free charge in accordance with the processes of the present disclosure causes the time course of those processes to match that of the analytical solution because a similar replacement occurs for the analytic solution (see, for example, FIG. 4 of Klee 2014).

Example 6

This example illustrates the use of the processes of the present disclosure as a tool to discover heretofore unknown mechanisms and phenomena of electrophysiological systems. In particular, using the $\Omega \to 0$ processes, the example shows that charges accumulate in concavities in electrophysiological systems. Such concavities are ubiquitous, the Nodes of Ranvier of myelinated nerves, the dendritic spines of cortical neurons, the junctional folds of neuromuscular junctions, and the sulci of the brain being just a few of the many examples that could be named.

Figure 25:
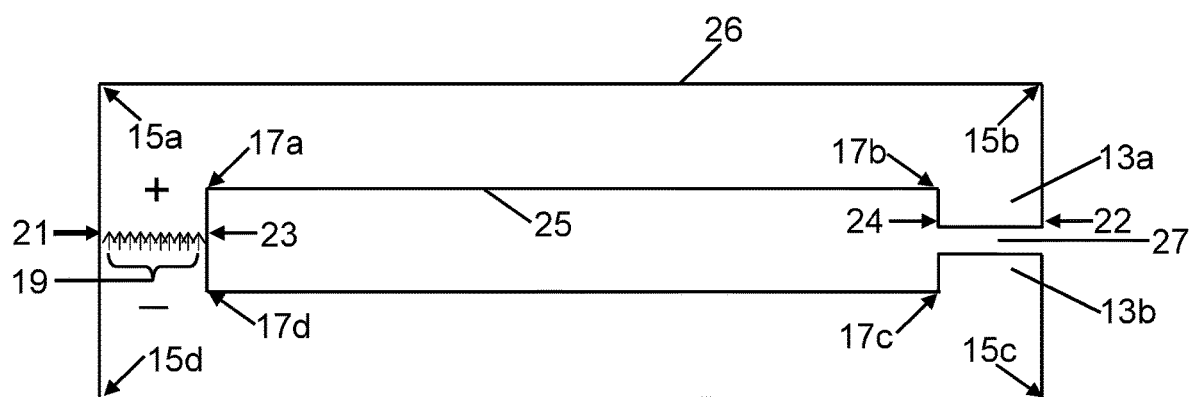
FIG. 25 is a midplane, cross-sectional, diagram of the system geometry used in Example 6. The system has two major concavities at 13a and 13b and four concavities at 15a-15d, as well as four convexities at 17a-17d.

FIG. 25 shows the geometry of the system used to explore this phenomenon. A total of just under 10,000 square-shaped, flattened, calculation cells were used in the modeling/simulation. The calculation cells were distributed to provide a racetrack-shaped conductor having two facing concavities 13a and 13b in the right vertical arm of the conductor, as well as four concave (as seen from the conductor) corners 15a, 15b, 15c, and 15d in the outer surface of the conductor and four convex (again, as seen from the conductor) corners 17a, 17b, 17c, and 17d in the inner surface.

In terms of calculation cells, the dimensions of the conductor's outer surface were 99 cells in length, 33 cells in height, and 11 cells in depth, while those of the inner surface were 77 cells in length, 11 cells in height, and 11 cells in depth. The perimeters around the conductor's inner and outer surfaces were thus 176 and 264 cells, respectively. The bottom surface of concavity 13a was 15 cells below the conductor's top surface and the top surface of concavity 13b was 15 cells above the conductor's bottom surface, thus leaving a gap of 3 cells between those surfaces. The bottom surface of the top concavity was defined by 121 (11×11) square-shaped, flattened, calculation cells, as was the top surface of the bottom concavity. For the purposes of this study, the relative dielectric constant of the conductor was taken to be 1.0 and all of the flattened, square-shaped, calculation cells were of the same size, namely, 1 micron×1 micron. The time step approach of Eq. (32) was used with a $\sigma_A$ value of 0.5 S/m and a $\Delta t$ value of $1.77 \times 10^{-12}$ seconds. The simulation was continued until steady state was achieved which was defined as the point where the change in the quantity of free charge per time step for each of the calculation cells dropped below $1 \times 10^{-6}$ elementary charges for an applied potential difference $\Delta \phi$ (see below) of 100 millivolts.

The applied source which generated the charge distributions was a 11×11 array of equal strength dipoles 19 located at the midplane of the left vertical arm of the conductor with the positive ends of the dipoles facing upward. The electric field produced by an individual dipole can be written in Cartesian coordinates as:

$$E_x=3Pzx/(4\pi\varepsilon_0 r^5), \tag{117}$$

$$E_y=3Pzy/(4\pi\varepsilon_0 r^5), \text{ and} \tag{118}$$

$$E_z=3Pz^2/(4\pi\varepsilon_0 r^5)-P/(4\pi\varepsilon_0 r^3). \tag{119}$$

where, without loss of generality, we have assumed that the dipole is located at the origin of the coordinate system and oriented in the +z direction. In these equations, x, y, and z are the coordinates of the field point, r is the distance from the dipole to the field point, and P is the strength of the dipole in, for example, coulomb-meters when distances are expressed in meters.

An applied potential difference $\Delta \phi$, e.g., a Nernst potential arising from an ionic concentration difference, can be converted into a P value by considering a continuous dipole layer (double layer) of constant dipole moment p per unit area. The potential difference across such a layer is given by:

$$\Delta\phi = p/\varepsilon_0, \tag{120}$$

which upon rearranging and multiplying by a surface area S associated with an individual dipole gives a P value of:

$$P=pS=\varepsilon_0\Delta\phi S. \tag{121}$$

Using this value for P in Eqs. (117)-(119), the redistributable free charge moving across a face of a calculation cell in a time period $\Delta t$ due to an applied potential difference expressed as individual dipoles is then the sum of the components of the dipole fields normal to the face of the calculation cell produced by the individual dipoles evaluated at, for example, the center of the face of the calculation cell times $\sigma_A \Delta t S_{cell}$, where $S_{cell}$ is the surface area of the face at which the calculation is performed. For the purposes of this example, the same $S_{cell}$ was used throughout the system and S for all of the individual dipoles was set equal to $S_{cell}$, it being understood that, if desired, $S_{cell}$ can vary from location to location and S can vary from individual dipole to individual dipole and need not be equal to $S_{cell}$.

The sign of the charge movement across a face of a calculation cell as a result of the normal field produced by an individual dipole depends on the orientation of the face's outward normal relative to the direction of the dipole. For the geometry of FIG. 26, only one of the components of the dipole field acts at each flattened calculation cell and the outward normal at the face is either parallel or anti-parallel to the direction of the component. For example, for the top surface of the conductor and face a of FIG. 2 as the reference face, the component that acts at the face is $E_z$ of Eq. (119), the outward normal is downward, the relative orientation is anti-parallel, and, for those locations where $E_z$ is positive, i.e., locations where the first term of Eq. (119) is greater than the second term such as the flattened calculation cells directly above the array of dipoles, charge is driven into the flattened calculation cells by the dipoles.

More generally, for a set of individual dipoles having strengths $P_i$ and unit normals $n_i$, a face having a unit outward normal n, and distances $r_i$ and unit vectors $n_{f \to d}$ from the center point of the face to the dipoles, the quantity of redistributable free charge $\Delta q^f$ entering the calculation cell through the face can be written:

$$\Delta q^f = -(\sigma_A \Delta t S_{cell}/4\pi\varepsilon_0)(\Sigma_i(P_i/r_i^3))(3(n_i \cdot n_{f \to d})(n \cdot n_{f \to d}) - n_i \cdot n), \quad (122)$$

where the dots between the unit vectors represent dot products. For the flattened calculation cells directly above the dipoles in FIG. 25, $\Delta q^f$ is positive since $n \cdot n_{f \to d}$ is positive and $n_i \cdot n_{f \to d}$ and $n_i \cdot n$ are negative, so that $(3(n_i \cdot n_{f \to d})(n \cdot n_{f \to d}) - n_i \cdot n)$ is negative, making the entire expression positive. As will be evident, when one or more dipole sources are used, Eq. (122) or an equivalent equation, becomes an additional term in Eq. (1) and thus in all of the subsequent equations based on Eq. (1).

Figure 26:
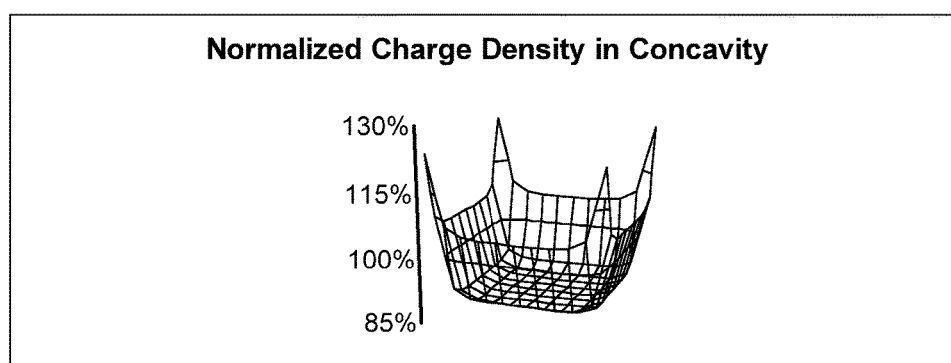
FIG. 26 is a topographical plot of normalized surface charge density for concavity 13a of FIG. 25.
Figure 27:
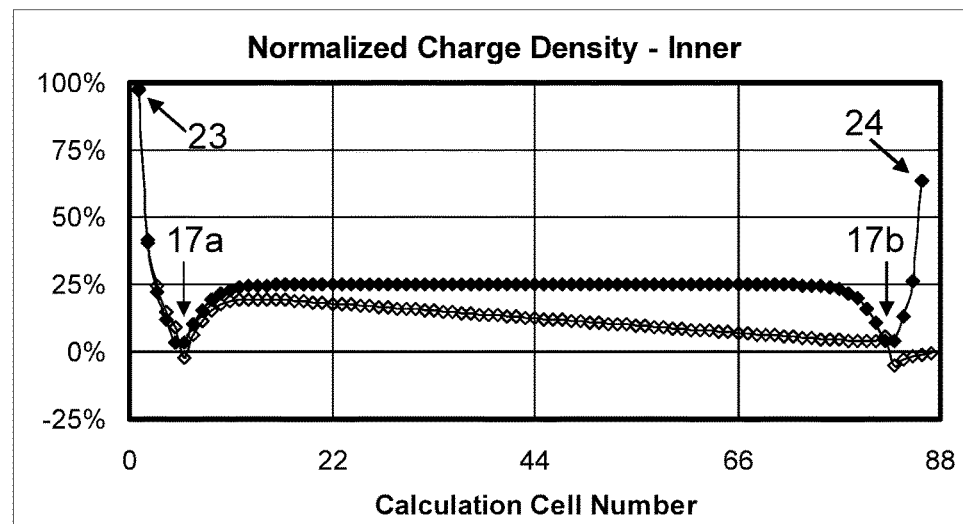
FIG. 27 is a plot of normalized surface charge density for the flattened calculation cells lying between locations 23 and 24 of path 25 of FIG. 25. The filled data points in this figure and in FIGS. 28 and 29 are for gap 27 present and the open data points are for the gap filled with the conductive material of the conductor.
Figure 28:
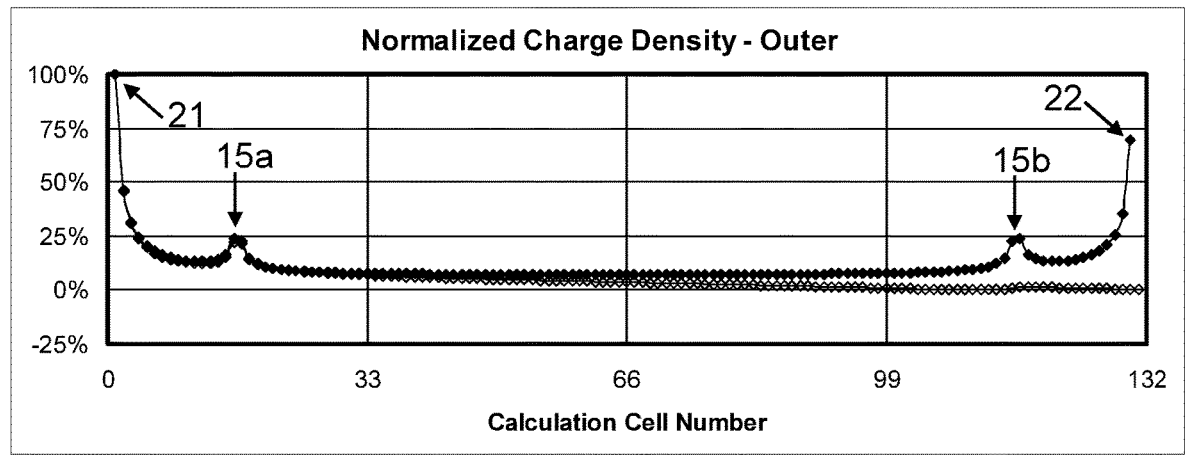
FIG. 28 is a plot of normalized surface charge density for the flattened calculation cells lying between locations 21 and 22 of path 26 of FIG. 25.
Figure 29:
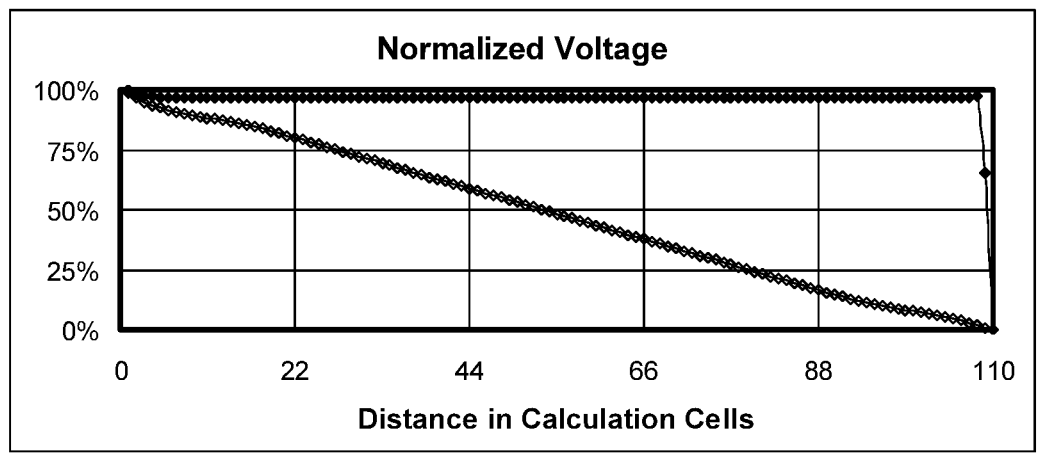
FIG. 29 is a plot of normalized voltage along a path midway between paths 25 and 26.

The results of the simulations for the system of FIG. 25 are shown in FIGS. 26-29. These figures show the surface charge distributions and, in the case of FIG. 29, the voltage distribution for the upper portion of the conductor of FIG. 25, the charge and voltage distributions for the lower portion being the negative of the distributions shown. The distribution of FIG. 26 is in a horizontal plane passing through the bottom surface of concavity 13a, and the distributions of FIGS. 27-29 are in the plane of FIG. 25.

The charge distributions have been normalized to the magnitude of the surface charge density on the inside of the conductor's outer surface directly adjacent to the layer of dipoles, i.e., the point identified by the reference number 21 in FIG. 25, which location, as discussed below, is insensitive to the presence or absence of concavities 13a and 13b, and which is an area of high surface charge density. The voltage distribution of FIG. 29 has been normalized to $\frac{1}{2}\Delta\phi$. The horizontal axis in FIG. 27 lies along path 25 of FIG. 25 between locations 23 and 24; the horizontal axis in FIG. 28 lies along path 26 of FIG. 25 between locations 21 and 22; and the horizontal axis of FIG. 29 lies along a path midway between paths 25 and 26 that begins at the dipole layer in the left arm of the conductor and continues to the midpoint of the right arm.

As illustrated by FIG. 26, concavities are powerful charge collectors. The magnitudes of the surface charge density along the bottoms of the concavities used in this example are more than 85% of the magnitude of the surface charge density directly adjacent to the dipoles and rises sharply at the junctions between the concavity's bottom and side walls. These effects are further illustrated in FIGS. 27 and 28 where the surface charge densities rise sharply for the portions of paths 25 and 26 within cavity 13a, reaching maxima for the flattened calculation cells at locations 22 and 24.

FIG. 28 shows that the concavities at 15a and 15b also produce increases in the surface charge density, while FIG. 27 shows that the convexities at 17a and 17b produce decreases in the surface charge density. The decrease in surface charge density at a convexity can be sufficient to change the sign of the density as illustrated in FIG. 27 for the system without concavities 13a and 13b (see, in particular, the portion of the open data point curve under reference number 17b in FIG. 27). A comparison of the curves for the filled and open data points of FIGS. 27 and 28 show that the surface charge densities in the region of the applied sources is insensitive to the presence (filled data points) or absence (open data points) of concavities 13a and 13b.

A comparison between FIGS. 26-28 and FIG. 29 illustrates the stark contrast in terms of complexity between charge distributions and voltage distributions. The charge distributions reflect and respond to the local geometry of the system, while the voltage distribution provides an average of those charge distributions which washes out the underlying complexity. The charge distributions thus provide more opportunities for affecting biological function than the voltage distribution.

As can be seen from the foregoing examples, the three improvements of the present disclosure, i.e., the $\Omega$ process, the $\delta \to 0$ process, and the alternating bound charge/free charge process, provide highly accurate charge distributions. The processes are therefore useful in modeling/simulating electrophysiological systems and users can employ them with confidence that the spatial and temporal charge distributions they provide are accurate representations of the biological problem being addressed.

VII. FEATURES

Based on the foregoing, the disclosure includes, but is not limited to, the following features. The features, as well as their various paragraphs and subparagraphs, can be used individually and in any and all combinations.

A. $\Omega$ Process

Feature 1: A computer-implemented process for computing and displaying a spatial distribution, a time series, or a spatial distribution and a time series of at least one electrical variable for at least a portion of an electrophysiological system, said method comprising:

(I) modeling said at least a portion of an electrophysiological system by a method that comprises:

(A) inputting data to a computer regarding structure and at least one electrical property of said at least a portion of an electrophysiological system;

(B) simulating, using the computer, at least one spatial charge distribution for said at least a portion of an electrophysiological system without first determining and differentiating an electrical potential distribution, wherein simulating comprises determining quantities of charge in a plurality of calculation cells, each of said plurality of calculation cells having at least two faces;

(II) using the computer to determine the spatial distribution, the time series, or the spatial distribution and the time series of the electrical variable from the at least one spatial charge distribution simulated in step (I); and (III) displaying the spatial distribution, the time series, or the spatial distribution and the time series of the electrical variable determined in step (II);

wherein for at least one (or a plurality, or a majority, or essentially all, or all) of said plurality of calculation cells, a quantity of charge for the calculation cell is determined in step (I)(B), at least in part, using a solid angle of a face of the calculation cell as seen from a quantity of charge in at least one other calculation cell (or from quantities of charge in a plurality of (or in a majority of, or in essentially all of, or in all of) the other calculation cells) of said plurality of calculation cells.

Feature 2: The computer-implemented process of Feature 1 wherein for at least one of said plurality of calculation cells, a quantity of charge for the calculation cell is determined in step (I)(B), at least in part, using a solid angle of a face of said calculation cell as seen from a quantity of charge in said calculation cell.

Feature 3: The computer-implemented process of Feature 1 wherein the at least one electrical variable is selected from the group consisting of electrical potentials, electric fields, currents, current densities, quantities of charge, charge densities, capacitance values, resistance values, and time constants.

Feature 4: The computer-implemented process of Feature 1 wherein in step (I)(B) at least one of the calculation cells of the plurality of calculation cells is a flattened calculation cell having only two faces with substantial areas as seen from quantities of charge in the other calculation cells of said plurality of calculation cells.

Feature 5: The computer-implemented process of Feature 4 wherein a quantity of charge for the flattened calculation cell is determined using ab initio solid angle calculations for only one face of the cell.

Feature 6: The computer-implemented process of Feature 1 wherein in step (I)(B) at least one of the calculation cells of the plurality of calculation cells is an interface calculation cell.

Feature 7: The computer-implemented process of Feature 1 wherein in step (I)(B) at least two of the calculation cells of the plurality of calculation cells is a pair of first and second interface calculation cells that oppose one another on opposite sides of an interface between a first volume having first electrical properties and a second volume having second electrical properties.

Feature 8: The computer-implemented process of Feature 7 wherein the first and second interface calculation cells are a pair of flattened calculation cells, each flattened calculation cell having only two faces with substantial areas as seen from quantities of charge in the other calculation cells of said plurality of calculation cells.

Feature 9: The computer-implemented process of Feature 8 wherein quantities of charge for the pair of flattened calculation cells is determined using ab initio solid angle calculations for only one face of one of the cells of the pair.

Feature 10: The computer-implemented process of Feature 1 wherein, in step (I)(B), at least one of the calculation cells of the plurality of calculation cells is an interior calculation cell.

(1) Free charge

Feature 11: The computer-implemented process of any of Features 1-10 wherein said at least one spatial charge distribution simulated in step (I)(B) comprises at least one redistributable free charge distribution.

Feature 12: The computer-implemented process of Feature 11 wherein said at least one redistributable free charge distribution is a steady state distribution.

(a) Interface Calculation Cells

Feature 13: The computer-implemented process of Feature 11 wherein, in step (I)(B), at least two of the calculation cells of the plurality of calculation cells is a pair of first and second interface calculation cells that oppose one another on opposite sides of an interface between a first volume having a first conductivity and a second volume having a second conductivity, the conductivity of the first interface calculation cell being the first conductivity and the conductivity of the second interface calculation cell being the second conductivity.

Feature 14: The computer-implemented process of Feature 13 wherein as inputted in step (I)(A), said first and second conductivities are different.

Feature 15: The computer-implemented process of Feature 14 wherein said first conductivity is greater than zero and the second conductivity is equal to zero.

Feature 16: The computer-implemented process of Feature 15 wherein, in step (I)(B), the first interface calculation cell contains a quantity of redistributable free charge.

Feature 17: The computer-implemented process of Feature 15 wherein, in step (I)(B), at least one quantity of imposed redistributable free charge is introduced into the first interface calculation cell.

Feature 18: The computer-implemented process of Feature 17 wherein the imposed redistributable free charge is applied free charge.

Feature 19: The computer-implemented process of Feature 17 wherein the imposed redistributable free charge is free charge associated with the direct action of a non-conservative field.

Feature 20: The computer-implemented process of Feature 15 wherein, in step (I)(B), the second interface calculation cell contains a quantity of non-redistributable free charge.

Feature 21: The computer-implemented process of Feature 15 wherein as inputted in step (I)(A), said first and second conductivities are each greater than zero, with the first conductivity being greater than the second conductivity.

Feature 22: The computer-implemented process of Feature 21 wherein, in step (I)(B), the first and second interface calculation cells each contain a quantity of redistributable free charge.

Feature 23: The computer-implemented process of Feature 21 wherein, in step (I)(B), only the first interface calculation cell contains a quantity of redistributable free charge.

Feature 24: The computer-implemented process of Feature 21 wherein in step (I)(B), at least one quantity of imposed redistributable free charge is introduced into at least one of the first and second interface calculation cells.

Feature 25: The computer-implemented process of Feature 24 wherein the imposed redistributable free charge is applied free charge.

Feature 26: The computer-implemented process of Feature 24 wherein the imposed redistributable free charge is free charge associated with the direct action of a non-conservative field.

(b) Interior Calculation Cells

Feature 27: The computer-implemented process of Feature 11 wherein, in step (I)(B), at least one calculation cell of the plurality of calculation cells is an interior calculation cell.

Feature 28: The computer-implemented process of Feature 27 wherein, as inputted in step (I)(A), the interior calculation cell has a conductivity greater than zero.

Feature 29: The computer-implemented process of Feature 28 wherein, in step (I)(B), the interior calculation cell contains a quantity of redistributable free charge.

Feature 30: The computer-implemented process of Feature 28 wherein, in step (I)(B), at least one quantity of imposed redistributable free charge is introduced into the interior calculation cell.

Feature 31: The computer-implemented process of Feature 30 wherein the imposed redistributable free charge is applied free charge.

Feature 32: The computer-implemented process of Feature 27 wherein, as inputted in step (I)(B), the interior calculation cell has a conductivity equal to zero.

Feature 33: The computer-implemented process of Feature 32 wherein, in step (I)(B), the interior calculation cell contains a quantity of non-redistributable free charge.

(2) Bound Charges

Feature 34: The computer-implemented process of any of Features 1-10 wherein said at least one spatial charge distribution simulated in step (I)(B) comprises at least one bound charge distribution.

(a) Interface Calculation Cells

Feature 35: The computer-implemented process of Feature 34 wherein, in step (I)(B), at least two of the calculation cells of the plurality of calculation cells is a pair of first and second interface calculation cells that oppose one another on opposite sides of an interface between a first volume having a first relative dielectric constant and a second volume having a second relative dielectric constant, the relative dielectric constant of the first interface calculation cell being the first relative dielectric constant and the relative dielectric constant of the second interface calculation cell being the second relative dielectric constant.

Feature 36: The computer-implemented process of Feature 35 wherein as inputted in step (I)(A), said first and second relative dielectric constants are different.

Feature 37: The computer-implemented process of Feature 36 wherein said first relative dielectric constant is greater than one and the second relative dielectric constant is equal to one.

Feature 38: The computer-implemented process of Feature 37 wherein, in step (I)(B), the first interface calculation cell contains a quantity of bound charge.

Feature 39: The computer-implemented process of Feature 36 wherein said first and second relative dielectric constants are each greater than one.

Feature 40: The computer-implemented process of Feature 39 wherein, in step (I)(B), the first and second interface calculation cells each contain a quantity of bound charge.

(b) Interior Calculation Cells

Feature 41: The computer-implemented process of Feature 34 wherein, in step (I)(B), at least one calculation cell of the plurality of calculation cells is an interior calculation cell.

Feature 42: The computer-implemented process of Feature 41 wherein, as inputted in step (I)(A), the at least one interior calculation cell has a relative dielectric constant greater than one.

Feature 43: The computer-implemented process of Feature 42 wherein, in step (I)(B), the interior calculation cell contains a quantity of free charge and a quantity of bound charge.

(3) Free and Bound Charges

Feature 44: The computer-implemented process of any of Features 1-10 wherein said at least one spatial charge distribution simulated in step (I)(B) comprises at least one free charge distribution and at least one bound charge distribution.

Feature 45: The computer-implemented process of Feature 44 wherein said at least one free charge distribution comprises at least one redistributable free charge distribution.

Feature 46: The computer-implemented process of Feature 45 wherein said at least one redistributable free charge distribution is a steady state distribution.

Feature 47: The computer-implemented process of Feature 44 wherein, in step (I)(B), the free charge distribution and the bound charge distribution are determined at a plurality of time steps, the free charge distribution being fixed when the bound charge distribution is determined and the bound charge distribution being fixed when the free charge distribution is determined.

Feature 48: The computer-implemented process of Feature 47 wherein at a time step, the bound charge distribution is determined before the free charge distribution.

Feature 49: The computer-implemented process of Feature 48 wherein at a time step, the bound charge distribution is determined based on a free charge distribution of a previous time step.

Feature 50: The computer-implemented process of Feature 48 wherein at a time step, the free charge distribution is determined based on a bound charge distribution for the same time step.

(a) Interface Calculation Cells

Feature 51: The computer-implemented process of Feature 44 wherein, in step (I)(B), at least two of the calculation cells of the plurality of calculation cells is a pair of first and second interface calculation cells that oppose one another on opposite sides of an interface between a first volume having a first conductivity and a first relative dielectric constant and a second volume having a second conductivity and a second relative dielectric constant, the conductivity and relative dielectric constant of the first interface calculation cell being the first conductivity and the first relative dielectric constant, respectively, and the conductivity and relative dielectric constant of the second interface calculation cell being the second conductivity and the second relative dielectric constant, respectively.

Feature 52: The computer-implemented process of Feature 51 wherein, as inputted in step (I)(A), said first and second conductivities are different and said first and second relative dielectric constants are the same, or said first and second conductivities are the same and said first and second relative dielectric constants are different, or said first and second conductivities are different and said first and second relative dielectric constants are different.

Feature 53: The computer-implemented process of Feature 52 wherein in step (I)(B), at least one of the interface calculation cells contains a quantity of redistributable free charge and at least one of the interface calculation cells contains a quantity of bound charge.

Feature 54: The computer-implemented process of Feature 52 wherein in step (I)(B), at least one of the interface calculation cells contains both a quantity of redistributable free charge and a quantity of bound charge.

Feature 55: The computer-implemented process of Feature 52 wherein in step (I)(B), at least one quantity of imposed redistributable free charge is introduced into at least one interface calculation cell.

Feature 56: The computer-implemented process of Feature 55 wherein the imposed redistributable free charge is applied free charge.

Feature 57: The computer-implemented process of Feature 55 wherein the imposed redistributable free charge is free charge associated with the direct action of a non-conservative field.

Feature 58: The computer-implemented process of Feature 52 wherein, in step (I)(B), at least one of the interface calculation cells contains a quantity of non-redistributable free charge.

(b) Interior Calculation Cells

Feature 59: The computer-implemented process of Feature 44 wherein, in step (I)(B), at least one of the calculation cells of the plurality of calculation cells is an interior calculation cell.

Feature 60: The computer-implemented process of Feature 59 wherein, as inputted in step (I)(A), the interior calculation cell has a conductivity greater than zero and a relative dielectric constant of one, or a conductivity equal to zero and a relative dielectric constant greater than one, or a conductivity greater than zero and a relative dielectric constant greater than one.

Feature 61: The computer-implemented process of Feature 60 wherein in step (I)(B), the interior calculation cell contains a quantity of free charge and a quantity of bound charge.

Feature 62: The computer-implemented process of Feature 60 wherein in step (I)(B), at least one quantity of imposed redistributable free charge is introduced into the interior calculation cell.

Feature 63: The computer-implemented process of Feature 62 wherein the imposed redistributable free charge is applied free charge.

Feature 64: The computer-implemented process of Feature 60 wherein, in step (I)(B), the interior calculation cell contains a quantity of non-redistributable free charge.

Feature 65: The computer-implemented process of Feature 60 wherein, in step (I)(B), the interior calculation cell contains a quantity of reduced free charge.

B. $\delta \rightarrow 0$ Process

Feature 66: A computer-implemented process for computing and displaying a spatial distribution, a time series, or a spatial distribution and a time series of at least one electrical variable for at least a portion of an electrophysiological system, said method comprising:

(I) modeling said at least a portion of an electrophysiological system by a method that comprises:

(A) inputting data to a computer regarding structure and at least one electrical property of said at least a portion of an electrophysiological system;

(B) simulating, using the computer, at least one spatial charge distribution for said at least a portion of an electrophysiological system without first determining and differentiating an electrical potential distribution, wherein simulating comprises determining quantities of charge in a plurality of calculation cells, each of said plurality of calculation cells having at least two faces;

(II) using the computer to determine the spatial distribution, the time series, or the spatial distribution and the time series of the electrical variable from the at least one spatial charge distribution simulated in step (I); and (III) displaying the spatial distribution, the time series, or the spatial distribution and the time series of the electrical variable determined in step (II);

wherein in step (I)(B) at least one (or a plurality, or a majority, or essentially all, or all) of the calculation cells of the plurality of calculation cells is a flattened calculation cell having only two faces with substantial areas as seen from quantities of charge in the other calculation cells of said plurality of calculation cells.

Feature 67: The computer-implemented process of Feature 66 wherein, in step (I)(B), a quantity of charge for the flattened calculation cell is determined using ab initio solid angle calculations for only one face of the cell.

Feature 68: The computer-implemented process of Feature 66 wherein, in step (I)(B), at least two of the calculation cells of the plurality of calculation cells is a pair of flattened first and second interface calculation cells that oppose one another on opposite sides of an interface between a first volume having first electrical properties and a second volume having second electrical properties, each flattened calculation cell having only two faces with substantial areas as seen from quantities of charge in the other calculation cells of said plurality of calculation cells.

Feature 69: The computer-implemented process of Feature 68 wherein, in step (I)(B), quantities of charge for the pair of flattened calculation cells is determined using ab initio solid angle calculations for only one face of one of the cells of the pair.

Feature 70: The computer-implemented process of Feature 66 wherein the at least one electrical variable is selected from the group consisting of electrical potentials, electric fields, currents, current densities, quantities of charge, charge densities, capacitance values, resistance values, and time constants.

C. Bound Charge/Free Charge Process

Feature 71: A computer-implemented process for computing and displaying a spatial distribution, a time series, or a spatial distribution and a time series of at least one electrical variable for at least a portion of an electrophysiological system, said method comprising:

(I) modeling said at least a portion of an electrophysiological system by a method that comprises:

(A) inputting data to a computer regarding structure and at least one electrical property of said at least a portion of an electrophysiological system;

(B) simulating, using the computer, at least one spatial charge distribution for said at least a portion of an electrophysiological system without first determining and differentiating an electrical potential distribution, wherein simulating comprises determining quantities of charge in a plurality of calculation cells, each of said plurality of calculation cells having at least two faces;

(II) using the computer to determine the spatial distribution, the time series, or the spatial distribution and the time series of the electrical variable from the at least one spatial charge distribution simulated in step (I); and (III) displaying the spatial distribution, the time series, or the spatial distribution and the time series of the electrical variable determined in step (II);

wherein said at least one spatial charge distribution simulated in step (I)(B) comprises at least one free charge distribution and at least one bound charge distribution.

Feature 72: The computer-implemented process of Feature 71 wherein, in step (I)(B), the free charge distribution and the bound charge distribution are determined at a plurality of time steps, the free charge distribution being fixed when the bound charge distribution is determined and the bound charge distribution being fixed when the free charge distribution is determined.

Feature 73: The computer-implemented process of Feature 72 wherein at a time step, the bound charge distribution is determined before the free charge distribution.

Feature 74: The computer-implemented process of Feature 73 wherein at a time step, the bound charge distribution is determined based on a free charge distribution of a previous time step.

Feature 75: The computer-implemented process of Feature 73 wherein at a time step, the free charge distribution is determined based on a bound charge distribution for the same time step.

Feature 76: The computer-implemented process of Feature 71 wherein the at least one electrical variable is selected from the group consisting of electrical potentials, electric fields, currents, current densities, quantities of charge, charge densities, capacitance values, resistance values, and time constants.

D. Interface/Interior Calculation Cells

Feature 77: A computer-implemented process for computing and displaying a spatial distribution, a time series, or a spatial distribution and a time series of at least one electrical variable for at least a portion of an electrophysiological system, said method comprising:

(I) modeling said at least a portion of an electrophysiological system by a method that comprises:

(A) inputting data to a computer regarding structure and at least one electrical property of said at least a portion of an electrophysiological system;

(B) simulating, using the computer, at least one spatial charge distribution for said at least a portion of an electrophysiological system without first determining and differentiating an electrical potential distribution, wherein simulating comprises determining quantities of charge in a plurality of calculation cells, each of said plurality of calculation cells having at least two faces;

(II) using the computer to determine the spatial distribution, the time series, or the spatial distribution and the time series of the electrical variable from the at least one spatial charge distribution simulated in step (I); and (III) displaying the spatial distribution, the time series, or the spatial distribution and the time series of the electrical variable determined in step (II);

wherein in step (I)(B), said plurality of calculation cells comprises at least one interior calculation cell and at least one interface calculation cell.

Feature 78: The computer-implemented process of Feature 77 wherein the at least one electrical variable is selected from the group consisting of electrical potentials, electric fields, currents, current densities, quantities of charge, charge densities, capacitance values, resistance values, and time constants.

E. Non-Transitory Computer Readable Medium

Feature 79: A non-transitory computer readable medium with instructions stored therein, that when executed by a processor, perform the steps:

(I) modeling at least a portion of an electrophysiological system by a method that comprises:

(A) inputting data regarding structure and at least one electrical property of said at least a portion of an electrophysiological system;

(B) simulating at least one spatial charge distribution for said at least a portion of an electrophysiological system without first determining and differentiating an electrical potential distribution, wherein simulating comprises determining quantities of charge in a plurality of calculation cells, each of said plurality of calculation cells having at least two faces;

(II) determining a spatial distribution, a time series, or a spatial distribution and a time series of an electrical variable from the at least one spatial charge distribution simulated in step (I); and (III) displaying the spatial distribution, the time series, or the spatial distribution and the time series of the electrical variable determined in step (II);

wherein for at least one (or a plurality, or a majority, or essentially all, or all) of said plurality of calculation cells, a quantity of charge for the calculation cell is determined in step (I)(B), at least in part, using a solid angle of a face of the calculation cell as seen from a quantity of charge in at least one other calculation cell (or from quantities of charge in a plurality of (or in a majority of, or in essentially all of, or in all of) the other calculation cells) of said plurality of calculation cells.

Feature 80: A non-transitory computer readable medium with instructions stored therein, that when executed by a processor, perform the steps:

(I) modeling at least a portion of an electrophysiological system by a method that comprises:

(A) inputting data regarding structure and at least one electrical property of said at least a portion of an electrophysiological system;

(B) simulating at least one spatial charge distribution for said at least a portion of an electrophysiological system without first determining and differentiating an electrical potential distribution, wherein simulating comprises determining quantities of charge in a plurality of calculation cells, each of said plurality of calculation cells having at least two faces;

(II) determining a spatial distribution, a time series, or a spatial distribution and a time series of an electrical variable from the at least one spatial charge distribution simulated in step (I); and (III) displaying the spatial distribution, the time series, or the spatial distribution and the time series of the electrical variable determined in step (II);

wherein in step (I)(B) at least one (or a plurality, or a majority, or essentially all, or all) of the calculation cells of the plurality of calculation cells is a flattened calculation cell having only two faces with substantial areas as seen from quantities of charge in the other calculation cells of said plurality of calculation cells.

Feature 81: A non-transitory computer readable medium with instructions stored therein, that when executed by a processor, perform the steps:

(I) modeling at least a portion of an electrophysiological system by a method that comprises:

(A) inputting data regarding structure and at least one electrical property of said at least a portion of an electrophysiological system;

(B) simulating at least one spatial charge distribution for said at least a portion of an electrophysiological system without first determining and differentiating an electrical potential distribution, wherein simulating comprises determining quantities of charge in a plurality of calculation cells, each of said plurality of calculation cells having at least two faces;

(II) determining a spatial distribution, a time series, or a spatial distribution and a time series of an electrical variable from the at least one spatial charge distribution simulated in step (I); and (III) displaying the spatial distribution, the time series, or the spatial distribution and the time series of the electrical variable determined in step (II);

wherein said at least one spatial charge distribution simulated in step (I)(B) comprises at least one free charge distribution and at least one bound charge distribution.

Feature 82: A non-transitory computer readable medium with instructions stored therein, that when executed by a processor, perform the steps:

(I) modeling at least a portion of an electrophysiological system by a method that comprises:

(A) inputting data regarding structure and at least one electrical property of said at least a portion of an electrophysiological system;

(B) simulating at least one spatial charge distribution for said at least a portion of an electrophysiological system without first determining and differentiating an electrical potential distribution, wherein simulating comprises determining quantities of charge in a plurality of calculation cells, each of said plurality of calculation cells having at least two faces;

(II) determining a spatial distribution, a time series, or a spatial distribution and a time series of an electrical variable from the at least one spatial charge distribution simulated in step (I); and (III) displaying the spatial distribution, the time series, or the spatial distribution and the time series of the electrical variable determined in step (II);

wherein in step (I)(B), said plurality of calculation cells comprises at least one interior calculation cell and at least one interface calculation cell.

Feature 83: A computer system comprising a non-transitory computer readable medium according to Feature 79, 80, 81, and/or 82 and a processor for executing the instructions stored therein.

Experimental measurements provide the electrical, chemical, structural, and dimensional properties of the electrophysiological systems referred to in these features. The various computations referred to in the features transform the data provided by those experimental measurements into forms, e.g., spatial charge distributions, which are displayed and used to interpret the underlying physiological phenomena which generated the experimental data. The transformed data is also used in the design of further experiments.

A variety of modifications that do not depart from the scope and spirit of the invention will be evident to persons of ordinary skill in the art from the foregoing disclosure. The following claims are intended to cover the specific embodiments set forth herein as well as such modifications, variations, and equivalents.

TABLE 1

| Superscript or Subscript | Meaning |
|---|---|
| Superscript f | Redistributable free charges of interface or interior calculation cells, except in Eqs. (1) and (2) where the superscript represents all types of free charge wherever located, i.e., quantities of redistributable and non-redistributable free charge of interface or interior calculation cells. |
| Superscript s | Non-redistributable free charges of interface or interior calculation cells. |
| Superscript b | Bound charges of interface or interior calculation cells. |
| Subscript A | Interface calculation cell which can contain quantities of redistributable free interface charge when $\sigma_A > 0$ or quantities of non-redistributable free interface charge when $\sigma_A = 0$, and, in either case, quantities of bound interface charge. In certain embodiments, $\sigma_A$ is assumed to be greater than $\sigma_B$. |
| Subscript B | Interface calculation cell which can contain quantities of redistributable free interface charge when $\sigma_B > 0$ or quantities of non-redistributable free interface charge when $\sigma_B = 0$, and, in either case, quantities of bound interface charge. |
| Subscript int | Interior calculation cell which can contain quantities of redistributable free interior charge when $\sigma_{int} > 0$ or quantities of non-redistributable free interior charge when $\sigma_{int} = 0$, and, in either case, quantities of bound interior charge. |

TABLE 2

| Calculation Cell | Solid Angle Solution (%) | '617/'466 Solution (%) |
|---|---|---|
| 20 | 2.6558E−00 | 2.4945E−00 |
| 19 | 2.1008E−10 | 2.7116E−01 |
| 18 | 4.2320E−11 | 4.8530E−02 |
| 17 | 8.4494E−12 | 2.2102E−02 |
| 16 | −1.8472E−12 | 1.5926E−02 |
| 15 | −1.6281E−12 | 1.2095E−02 |
| 14 | −7.2402E−13 | 8.4108E−03 |
| 13 | −2.2371E−13 | 4.2677E−03 |
| 12 | −4.1325E−14 | −8.2560E−04 |
| 11 | 2.4218E−12 | −7.4777E−03 |
| 10 | 5.9644E−12 | −1.6545E−02 |
| 9 | 1.0056E−11 | −2.9298E−02 |

TABLE 2-continued

| Calculation Cell | Solid Angle Solution (%) | '617/'466 Solution (%) |
|---|---|---|
| 8 | 1.0042E−11 | −4.7681E−02 |
| 7 | 3.9690E−12 | −7.4687E−02 |
| 6 | −1.2341E−11 | −1.1485E−01 |
| 5 | −6.6227E−11 | −1.7463E−01 |
| 4 | −1.4931E−10 | −2.6177E−01 |
| 3 | −1.3713E−10 | −3.8139E−01 |
| 2 | 2.6236E−10 | −5.2517E−01 |
| 1 | 1.1033E−09 | −6.5578E−01 |
| 0 | 1.6176E−09 | −7.1092E−01 |
| −1 | 1.1033E−09 | −6.5578E−01 |
| −2 | 2.6236E−10 | −5.2517E−01 |
| −3 | −1.3713E−10 | −3.8139E−01 |
| −4 | −1.4931E−10 | −2.6177E−01 |
| −5 | −6.6226E−11 | −1.7463E−01 |
| −6 | −1.2341E−11 | −1.1485E−01 |
| −7 | 3.9671E−12 | −7.4687E−02 |
| −8 | 1.0042E−11 | −4.7681E−02 |
| −9 | 1.0055E−11 | −2.9298E−02 |
| −10 | 5.9632E−12 | −1.6545E−02 |
| −11 | 2.4218E−12 | −7.4777E−03 |
| −12 | −4.1856E−14 | −8.2560E−04 |
| −13 | −2.2271E−13 | 4.2677E−03 |
| −14 | −7.2449E−13 | 8.4108E−03 |
| −15 | −1.6282E−12 | 1.2095E−02 |
| −16 | −1.8475E−12 | 1.5926E−02 |
| −17 | 8.4494E−12 | 2.2102E−02 |
| −18 | 4.2320E−11 | 4.8530E−02 |
| −19 | 2.1009E−10 | 2.7116E−01 |
| −20 | 2.6558E−00 | 2.4945E−00 |

What is claimed is:

1. A computer-implemented process for computing and displaying a spatial distribution, a time series, or a spatial distribution and a time series of at least one electrical variable for at least a portion of an electrophysiological system, said method comprising:
   (I) modeling said at least a portion of an electrophysiological system by a method that comprises:
      (A) inputting data to a computer regarding structure and at least one electrical property of said at least a portion of an electrophysiological system;
      (B) simulating, using the computer, at least one spatial charge distribution for said at least a portion of an electrophysiological system without first determining and differentiating an electrical potential distribution, wherein simulating comprises determining quantities of charge in a plurality of calculation cells, each of said plurality of calculation cells having at least two faces;
   (II) using the computer to determine the spatial distribution, the time series, or the spatial distribution and the time series of the electrical variable from the at least one spatial charge distribution simulated in step (I); and
   (III) displaying the spatial distribution, the time series, or the spatial distribution and the time series of the electrical variable determined in step (II);
   wherein for at least one of said plurality of calculation cells, a quantity of charge for the calculation cell is determined in step (I)(B), at least in part, using a solid angle of a face of the calculation cell as seen from a quantity of charge in at least one other calculation cell of said plurality of calculation cells.

2. The computer-implemented process of claim 1 wherein the at least one electrical variable is selected from the group consisting of electrical potentials, electric fields, currents, current densities, quantities of charge, charge densities, capacitance values, resistance values, and time constants.

3. The computer-implemented process of claim 1 wherein in step (I)(B) at least two of the calculation cells of the plurality of calculation cells is a pair of first and second interface calculation cells that oppose one another on opposite sides of an interface between a first volume having first electrical properties and a second volume having second electrical properties.

4. The computer-implemented process of claim 1 wherein, in step (I)(B), at least one of the calculation cells of the plurality of calculation cells is an interior calculation cell.

5. The computer-implemented process of claim 1 wherein said at least one spatial charge distribution simulated in step (I)(B) comprises at least one redistributable free charge distribution.

6. The computer-implemented process of claim 1 wherein said at least one spatial charge distribution simulated in step (I)(B) comprises at least one bound charge distribution.

7. The computer-implemented process of claim 1 wherein:
(a) said at least one spatial charge distribution simulated in step (I)(B) comprises at least one free charge distribution and at least one bound charge distribution; and
(b) the free charge distribution and the bound charge distribution are determined at a plurality of time steps, the free charge distribution being fixed when the bound charge distribution is determined and the bound charge distribution being fixed when the free charge distribution is determined.

8. The computer-implemented process of claim 7 wherein at a time step, the bound charge distribution is determined before the free charge distribution.

9. A computer-implemented process for computing and displaying a spatial distribution, a time series, or a spatial distribution and a time series of at least one electrical variable for at least a portion of an electrophysiological system, said method comprising:
(I) modeling said at least a portion of an electrophysiological system by a method that comprises:
(A) inputting data to a computer regarding structure and at least one electrical property of said at least a portion of an electrophysiological system;
(B) simulating, using the computer, at least one spatial charge distribution for said at least a portion of an electrophysiological system without first determining and differentiating an electrical potential distribution, wherein simulating comprises determining quantities of charge in a plurality of calculation cells, each of said plurality of calculation cells having at least two faces;
(II) using the computer to determine the spatial distribution, the time series, or the spatial distribution and the time series of the electrical variable from the at least one spatial charge distribution simulated in step (I); and
(III) displaying the spatial distribution, the time series, or the spatial distribution and the time series of the electrical variable determined in step (II);
wherein said at least one spatial charge distribution simulated in step (I)(B) comprises at least one free charge distribution and at least one bound charge distribution.

10. The computer-implemented process of claim 9 wherein the at least one electrical variable is selected from the group consisting of electrical potentials, electric fields, currents, current densities, quantities of charge, charge densities, capacitance values, resistance values, and time constants.

11. The computer-implemented process of claim 9 wherein, in step (I)(B), the free charge distribution and the bound charge distribution are determined at a plurality of time steps, wherein:
(a) the free charge distribution is fixed when the bound charge distribution is determined and the bound charge distribution is fixed when the free charge distribution is determined; and
(b) at a time step, the bound charge distribution is determined before the free charge distribution.

12. The computer-implemented process of claim 11 wherein at a time step, the bound charge distribution is determined based on a free charge distribution of a previous time step.

13. The computer-implemented process of claim 11 wherein at a time step, the free charge distribution is determined based on a bound charge distribution for the same time step.

14. A computer-implemented process for computing and displaying a spatial distribution, a time series, or a spatial distribution and a time series of at least one electrical variable for at least a portion of an electrophysiological system, said method comprising:
(I) modeling said at least a portion of an electrophysiological system by a method that comprises:
(A) inputting data to a computer regarding structure and at least one electrical property of said at least a portion of an electrophysiological system;
(B) simulating, using the computer, at least one spatial charge distribution for said at least a portion of an electrophysiological system without first determining and differentiating an electrical potential distribution, wherein simulating comprises determining quantities of charge in a plurality of calculation cells, each of said plurality of calculation cells having at least two faces;
(II) using the computer to determine the spatial distribution, the time series, or the spatial distribution and the time series of the electrical variable from the at least one spatial charge distribution simulated in step (I); and
(III) displaying the spatial distribution, the time series, or the spatial distribution and the time series of the electrical variable determined in step (II);
wherein said at least one spatial charge distribution simulated in step (I)(B) is simulated without calculating charges at locations that are within the body of at least one conductive medium of said at least a portion of an electrophysiological system, other than those locations, if any, of said at least one conductive medium where charge is applied at the beginning, during the course of, or both at the beginning and during the course of the simulation.

15. The computer-implemented process of claim 14 wherein the body of the at least one conductive medium is free of applied charge at the beginning of the simulation and does not receive applied charge during the course of the simulation.

16. The computer-implemented process of claim 14 wherein the body of the at least one conductive medium is isotropic.

17. The computer-implemented process of claim 14 wherein the at least one electrical variable is selected from the group consisting of electrical potentials, electric fields, currents, current densities, quantities of charge, charge densities, capacitance values, resistance values, and time constants.

* * * * *